(12) United States Patent
Johnson et al.

(10) Patent No.: US 12,173,071 B2
(45) Date of Patent: Dec. 24, 2024

(54) METHODS AND COMPOSITIONS COMPRISING B7H3 CHIMERIC ANTIGEN RECEPTORS

(71) Applicant: Seattle Children's Hospital, Seattle, WA (US)

(72) Inventors: Adam Johnson, Seattle, WA (US); Michael C. Jensen, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 635 days.

(21) Appl. No.: 17/271,813

(22) PCT Filed: Aug. 29, 2019

(86) PCT No.: PCT/US2019/048814
§ 371 (c)(1),
(2) Date: Feb. 26, 2021

(87) PCT Pub. No.: WO2020/047257
PCT Pub. Date: Mar. 5, 2020

(65) Prior Publication Data
US 2021/0324083 A1    Oct. 21, 2021

Related U.S. Application Data

(60) Provisional application No. 62/725,599, filed on Aug. 31, 2018.

(51) Int. Cl.
| | |
|---|---|
| *C07K 16/28* | (2006.01) |
| *A61K 39/395* | (2006.01) |
| *A61P 35/00* | (2006.01) |
| *C07K 14/705* | (2006.01) |
| *C07K 14/71* | (2006.01) |
| *C07K 14/725* | (2006.01) |

(52) U.S. Cl.
CPC ...... *C07K 16/2827* (2013.01); *C07K 14/7051* (2013.01); *C07K 14/70521* (2013.01); *C07K 14/70578* (2013.01); *C07K 14/71* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 6,040,177 | A | 3/2000 | Riddell |
| 8,802,374 | B2 | 8/2014 | Jensen |
| 10,736,918 | B2* | 8/2020 | Jensen .................. A61P 1/18 |
| 10,780,118 | B2* | 9/2020 | Jensen .................. A61K 35/17 |
| 10,869,889 | B2* | 12/2020 | Jensen .................. A61P 31/12 |
| 2012/0294796 | A1* | 11/2012 | Johnson ............. A61K 47/6849 536/23.53 |
| 2013/0149236 | A1 | 6/2013 | Johnson |
| 2015/0306141 | A1* | 10/2015 | Jensen .................... A61P 15/00 435/325 |
| 2016/0053017 | A1* | 2/2016 | Orentas ............ G01N 33/57492 435/254.11 |
| 2016/0151491 | A1* | 6/2016 | Rabinovich ............ A61K 35/17 435/328 |
| 2016/0250258 | A1* | 9/2016 | Delaney ................. A61P 13/12 424/184.1 |
| 2017/0296676 | A1* | 10/2017 | Stephan ............. A61K 39/0011 |
| 2018/0200298 | A1 | 7/2018 | Jensen |
| 2018/0355318 | A1* | 12/2018 | Delaney ............. C07K 14/7051 |
| 2019/0111080 | A1* | 4/2019 | Shah .................... C07K 14/705 |
| 2019/0112380 | A1* | 4/2019 | Chaudhary ........... A61K 45/06 |
| 2021/0052649 | A1* | 2/2021 | Jensen ............... C07K 14/7151 |
| 2021/0171602 | A1* | 6/2021 | Mackall ................. A61P 35/00 |

FOREIGN PATENT DOCUMENTS

| | | |
|---|---|---|
| WO | WO 11/109400 | 9/2011 |
| WO | WO 14/031687 | 2/2014 |
| WO | WO 14/160627 | 10/2014 |
| WO | WO 15/157384 | 10/2015 |
| WO | WO 2015/157391 | 10/2015 |
| WO | WO 2017/044699 A1 | 3/2017 |
| WO | WO 2017/189959 A1 | 11/2017 |

OTHER PUBLICATIONS

Ajina et al. (2018) Strategies to Address Chimeric Antigen Receptor Tonic Signaling. Mol Cancer Ther; 17(9): 1795-815.*
Almasbak et al. (2015) Inclusion of an IgG1-Fc spacer abrogates efficacy of CD19 CAR T cells in a xenograft mouse model. Gene Therapy 22: 391-403.*
Chang et al. (2018) Rewiring T-cell responses to soluble factors with chimeric antigen receptors. Nature Chemical Biology 14(3): 317-324.*
Hudecek et al. (2013) Receptor Affinity and Extracellular Domain Modifications Affect Tumor Recognition by ROR1-Specific Chimeric Antigen Receptor T Cells. Clin Cancer Res; 19(12): 3153-3164.*
Jonnalagadda et al. (2015) Chimeric Antigen Receptors with Mutated IgG4 Fc Spacer Avoid Fc Receptor Binding and Improve T Cell Persistence and Antitumor Efficacy. Molecular Therapy vol. 23 No. 4, 757-768.*
Liu et al. (2016) Inclusion of Strep-tag II in design of antigen receptors for T-cell immunotherapy. Nature biotechnology 34, No. 4: 430-434.*
Qin et al. (2017) Incorporation of a hinge domain improves the expansion of chimeric antigen receptor T cells. Journal of Hematology & Oncology 10(68): 1-11.*

(Continued)

*Primary Examiner* — Ilia I Ouspenski
(74) *Attorney, Agent, or Firm* — Knobbe, Martens, Olson & Bear LLP

(57) ABSTRACT

Embodiments of the methods and compositions provided herein relate to chimeric antigen receptors (CARs) that specifically bind to B7H3. Some embodiments relate to cell-based immunotherapy targeting tumors, such as tumors comprising B7H3+ cells.

24 Claims, 62 Drawing Sheets

Specification includes a Sequence Listing.

(56) References Cited

OTHER PUBLICATIONS

Chen et al., 2014, The coexpression and clinical significance of costimulatory molecules B7-H1, B7-H3, and B7-H4 in human pancreatic cancer, OncoTargets Ther. 7:1465-1472.

Hu et al., 2015, Expression of costimulatory molecule B7-H3 and its prognostic implications in human acute leukemia, Hematology, 20(4):187-195.

Hudecek et al., 2013, Receptor affinity and extracellular domain modifications affect tumor recognition by ROR1-specific chimeric antigen receptor T cells, Clin Cancer Res. 19:3153-3164.

Ingebrigtsen et al., 2014, B7-H3 expression in colorectal cancer: associations with clinicopathological parameters and patient outcome, BMC Cancer. 14:602.

Karlin et al., Jun. 1993, Applications and statistics for multiple high-scoring segments in molecular sequences, Proc. Natl. Acad. Sci. USA, 90:5873-5877.

Kunkele et al., 2015, Functional tuning of CARs reveals signaling threshold above which CD8+ Ctl antitumor potency is attenuated due to cell Fas-FasL-dependent AICD, Cancer Immunol Res; 3(4):368-379.

Loo et al., Jul. 15, 2012, Development of an Fc-enhanced anti-B7-H3 monoclonal antibody with potent antitumor activity, Clin Cancer Res: 18(14):3834-3845.

Schaffer et al., 2001, Improving the accuracy of PSI-BLAST protein database searched with composition-based statistics and other refinements, Nucleic Acids Res., 29(14):2994-3005.

Sun et al., 2014, 87-H3 expression in breast cancer and upregulation of VEGF through gene silence, OncoTargets and Therapy, 7:1979-1986.

Wang et al., 2013, B7-H3 associated with tumor progression and epigenetic regulatory activity in cutaneous melanoma, J Invest Dermatol, 133:2050-2058.

Zang et al., Aug. 2010, Tumor associated endothelial expression of B7-H3 predicts survival in ovarian carcinomas, Mod Pathol. 23(8):1104-1112.

Zang et al., Dec. 4, 2007, B7-H3 and B7x are highly expressed in human prostate cancer and associated with disease spread and poor outcome, Proc Natl Acad Sci USA, 104(49):19458-19463.

Zhou et al., Feb. 2013, B7-H3, a potential therapeutic target, is expressed in diffuse intrinsic pontine glioma, J Neurooncol. 111(3):257-264.

Chow, Kwong-Hon (Kevin) et al.,—Abstract "327 B7-H3 Chimeric Antigen Receptor Modified T Cells Show Potent Anti-Tumor Activity in a Preclinical Model of Glioblastoma" Neurosurgery, Aug. 2017, p. 272, vol. 64, Issue CN Suppl 1.

Nehama, Dean et al., "B7-H3-redirected chimeric antigen receptor T cells target glioblastoma and neurospheres" EBioMedicine, 2019, pp. 33-43, vol. 47.

Park, Yuk Pheel et al., "CD70 as a target for chimeric antigen receptor T cells in head and neck squamous cell carcinoma" Oral Oncol., Mar. 2018, pp. 145-150, vol. 78.

Tang, Xin et al., "B7-H3 as a Novel CAR-T Therapeutic Target for Glioblastoma" Molecular Therapy: Oncolytics, Sep. 2019, pp. 279-287, vol. 14.

International Search Report for PCT/US2019/048814 dated Nov. 25, 2019.

Chow et al., Sep. 2017, B7-H3 chimeric antigen receptor modified T cells show potent anti-tumor activity in a preclinical model of glioblastoma, Neurosurgery, 64(1):272 (abstract).

Du et al., May 2018, Effective antitumor responses in the absence of toxicity in pancreatic ductal adenocarcinoma models by tarting B7-H3 via chimeric antigen receptor T cells, Molecular Therapy, 26(5,Suppl 1):439 (abstract).

Hudecek et al., Feb. 2015, The nonsignaling extracellular spacer domain of chimeric antigen receptors is decisive for in vivo antitumor activity, Cancer Immunol Res., 3(2):125-135.

Kadapakkam et al., Jun. 2018, B7-H3 car t cells mediate in vitro and in vivo activity against neuroblastoma xenografts, Pediatric Blood and Cancer, 65(Suppl 1):S269-S270 (abstract).

\* cited by examiner

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Synthetic; VH CDR1 polypeptide

<400> SEQUENCE: 1

Phe Gly Met His
1
```

```
<210> SEQ ID NO 2
<211> LENGTH: 16
<212> TYPE: PRT
<213> ORGANISM: Artificial Sequence
<220> FEATURE:
<223> OTHER INFORMATION: Synthetic; VH CDR2 polypeptide

<400> SEQUENCE: 2

Tyr Ile Ser Ser Asp Ser Ser Ala Ile Tyr Tyr Ala Asp Thr Val Lys
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic; VH CDR3 polypeptide

<400> SEQUENCE: 3

Gly Arg Glu Asn Ile Tyr Tyr Gly Ser Arg Leu Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic; VL CDR1 polypeptide

<400> SEQUENCE: 4

Lys Ala Ser Gln Asn Val Asp Thr Asn Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic; VL CDR2 polypeptide

<400> SEQUENCE: 5

Ser Ala Ser Tyr Arg Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic; VL CDR3 polypeptide

<400> SEQUENCE: 6

Gln Gln Tyr Asn Asn Tyr Pro Phe Thr
1               5

<210> SEQ ID NO 7
<211> LENGTH: 12
<212> TYPE: DNA
<213> ORGANISM: Artificial Sequence
<220> FEATURE:
<223> OTHER INFORMATION: Synthetic; VH CDR1 nucleic acid

<400> SEQUENCE: 7
tttggaatgc ac                                                           12

<210> SEQ ID NO 8
<211> LENGTH: 48
```

```
<212> TYPE: DNA
<213> ORGANISM: Artificial Sequence
<220> FEATURE:
<223> OTHER INFORMATION: Synthetic; VH CDR2 nucleic acid

<400> SEQUENCE: 8
tacattagta gtgacagtag tgccatctac tatgcagaca cagtgaag            48

<210> SEQ ID NO 9
<211> LENGTH: 39
<212> TYPE: DNA
<213> ORGANISM: Artificial Sequence
<220> FEATURE:
<223> OTHER INFORMATION: Synthetic; VH CDR3 nucleic acid

<400> SEQUENCE: 9
gggagggaaa acatttacta cggtagtagg cttgactac                      39

<210> SEQ ID NO 10
<211> LENGTH: 33
<212> TYPE: DNA
<213> ORGANISM: Artificial Sequence
<220> FEATURE:
<223> OTHER INFORMATION: Synthetic; VL CDR1 nucleic acid

<400> SEQUENCE: 10
aaggccagtc agaatgtgga tactaatgta gcc                            33

<210> SEQ ID NO 11
<211> LENGTH: 21
<212> TYPE: DNA
<213> ORGANISM: Artificial Sequence
<220> FEATURE:
<223> OTHER INFORMATION: Synthetic; VL CDR2 nucleic acid

<400> SEQUENCE: 11
tcggcatcct accggtacag t                                         21

<210> SEQ ID NO 12
<211> LENGTH: 27
<212> TYPE: DNA
<213> ORGANISM: Artificial Sequence
<220> FEATURE:
<223> OTHER INFORMATION: Synthetic; VL CDR3 nucleic acid

<400> SEQUENCE: 12
cagcaatata caactatcc attcacg                                    27

<210> SEQ ID NO 13
<211> LENGTH: 122
<212> TYPE: PRT
<213> ORGANISM: Artificial Sequence
<220> FEATURE:
<223> OTHER INFORMATION: Synthetic; VH region polypeptide

<400> SEQUENCE: 13

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60
```

```
Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
            115                 120
```

```
<210> SEQ ID NO 14
<211> LENGTH: 366
<212> TYPE: DNA
<213> ORGANISM: Artificial Sequence
<220> FEATURE:
<223> OTHER INFORMATION: Synthetic; VH region nucleic acid

<400> SEQUENCE: 14
gatgtgcagc tggtggagtc tgggggaggc ttagtgcagc ctggagggtc ccggaaactc      60
tcctgtgcag cctctggatt cactttcagt agctttggaa tgcactgggt tcgtcaggct    120
ccagagaagg ggctggagtg ggtcgcatac attagtagtg acagtagtgc catctactat    180
gcagacacag tgaagggccg attcaccatc tccagagaca atcccaagaa caccctgttc    240
ctgcaaatga ccagtctaag gtctgaggac acggccatgt attactgtgg aagagggagg    300
gaaaacattt actacggtag taggcttgac tactggggcc aaggcaccac tctcacagtc    360
tcctca                                                                366
```

```
<210> SEQ ID NO 15
<211> LENGTH: 107
<212> TYPE: PRT
<213> ORGANISM: Artificial Sequence
<220> FEATURE:
<223> OTHER INFORMATION: Synthetic; VL region polypeptide

<400> SEQUENCE: 15

Asp Ile Ala Met Thr Gln Ser Gln Lys Phe Met Ser Thr Ser Val Gly
  1               5                  10                  15

Asp Arg Val Ser Val Thr Cys Lys Ala Ser Gln Asn Val Asp Thr Asn
             20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
         50                  55                  60

Ser Gly Ser Gly Thr Asp Phe Thr Leu Thr Ile Asn Asn Val Gln Ser
 65                  70                  75                  80

Glu Asp Leu Ala Glu Tyr Phe Cys Gln Gln Tyr Asn Asn Tyr Pro Phe
                 85                  90                  95

Thr Phe Gly Ser Gly Thr Lys Leu Glu Ile Lys
            100                 105
```

```
<210> SEQ ID NO 16
<211> LENGTH: 321
<212> TYPE: DNA
<213> ORGANISM: Artificial Sequence
<220> FEATURE:
<223> OTHER INFORMATION: Synthetic; VL region nucleic acid

<400> SEQUENCE: 16
gacattgcga tgacccagtc tcaaaaattc atgtccacat cagtaggaga cagggtcagc      60
```

```
gtcacctgca aggccagtca gaatgtggat actaatgtag cctggtatca acagaaacca    120
gggcaatctc ctaaagcact gatttactcg gcatcctacc ggtacagtgg agtccctgat    180
cgcttcacag gcagtggatc tgggacagat ttcactctca ccatcaacaa tgtgcagtct    240
gaagacttgg cagagtattt ctgtcagcaa tataacaact atccattcac gttcggctcg    300
gggacaaagt tggaaataaa a                                              321
```

<210> SEQ ID NO 17
<211> LENGTH: 5
<212> TYPE: PRT
<213> ORGANISM: Artificial Sequence
<220> FEATURE:
<223> OTHER INFORMATION: Synthetic; spacer region
<220> FEATURE:
<221> NAME/KEY: MISC_FEATURE
<222> LOCATION: (1)..(1)
<223> OTHER INFORMATION: X = Cys, Gly, or Arg
<220> FEATURE:
<221> NAME/KEY: MISC_FEATURE
<222> LOCATION: (4)..(4)
<223> OTHER INFORMATION: X = Cys, or Thr

<400> SEQUENCE: 17

```
Xaa Pro Pro Xaa Pro
1               5
```

<210> SEQ ID NO 18
<211> LENGTH: 12
<212> TYPE: PRT
<213> ORGANISM: Artificial Sequence
<220> FEATURE:
<223> OTHER INFORMATION: Synthetic; Small (S) spacer

<400> SEQUENCE: 18

```
Glu Ser Lys Tyr Gly Pro Pro Cys Pro Pro Cys Pro
1               5                   10
```

<210> SEQ ID NO 19
<211> LENGTH: 119
<212> TYPE: PRT
<213> ORGANISM: Artificial Sequence
<220> FEATURE:
<223> OTHER INFORMATION: Synthetic; Medium (M) spacer

<400> SEQUENCE: 19

```
Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115
```

<210> SEQ ID NO 20
<211> LENGTH: 229
<212> TYPE: PRT
<213> ORGANISM: Artificial Sequence
<220> FEATURE:
<223> OTHER INFORMATION: Synthetic; Long (L) spacer

<400> SEQUENCE: 20

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 21
<211> LENGTH: 15
<212> TYPE: PRT
<213> ORGANISM: Artificial Sequence
<220> FEATURE:
<223> OTHER INFORMATION: Synthetic; Human IgG1 hinge

<400> SEQUENCE: 21

Glu Pro Lys Ser Cys Asp Lys Thr His Thr Cys Pro Pro Cys Pro
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic; Human IgG2 hinge

<400> SEQUENCE: 22

Glu Arg Lys Cys Cys Val Glu Cys Pro Pro Cys Pro
1               5                   10

```
<210> SEQ ID NO 23
<211> LENGTH: 16
<212> TYPE: PRT
<213> ORGANISM: Artificial Sequence
<220> FEATURE:
<223> OTHER INFORMATION: Synthetic; Human IgG3 hinge

<400> SEQUENCE: 23

Glu Leu Lys Thr Pro Leu Gly Asp Thr His Thr Cys Pro Arg Cys Pro
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic; Human IgG4 hinge

<400> SEQUENCE: 24

Glu Ser Lys Tyr Gly Pro Pro Cys Pro Ser Cys Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic; Modified human IgG4 hinge

<400> SEQUENCE: 25

Glu Ser Lys Tyr Gly Pro Pro Cys Pro Pro Cys Pro
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic; Modified human IgG4 hinge

<400> SEQUENCE: 26

Tyr Gly Pro Pro Cys Pro Pro Cys Pro
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic; Modified human IgG4 hinge

<400> SEQUENCE: 27

Lys Tyr Gly Pro Pro Cys Pro Pro Cys Pro
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic; Modified human IgG4 hinge

<400> SEQUENCE: 28

Glu Val Val Lys Tyr Gly Pro Pro Cys Pro Pro Cys Pro
1               5                   10
```

<210> SEQ ID NO 29
<211> LENGTH: 84
<212> TYPE: DNA
<213> ORGANISM: Artificial Sequence
<220> FEATURE:
<223> OTHER INFORMATION: Synthetic; CD28tm nucleotide sequence

<400> SEQUENCE: 29

```
atgttctggg tgctggtggt ggtcggaggc gtgctggcct gctacagcct gctggtcacc      60
gtggccttca tcatcttttg ggtg                                             84
```

<210> SEQ ID NO 30
<211> LENGTH: 28
<212> TYPE: PRT
<213> ORGANISM: Artificial Sequence
<220> FEATURE:
<223> OTHER INFORMATION: Synthetic; CD28tm amino acid sequence

<400> SEQUENCE: 30

```
Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

<210> SEQ ID NO 31
<211> LENGTH: 336
<212> TYPE: DNA
<213> ORGANISM: Artificial Sequence
<220> FEATURE:
<223> OTHER INFORMATION: Synthetic; CD3-zeta signaling domain nucleotide
      sequence

<400> SEQUENCE: 31

```
cgggtgaagt tcagcagaag cgccgacgcc cctgcctacc agcagggcca gaatcagctg      60
tacaacgagc tgaacctggg cagaagggaa gagtacgacg tcctggataa gcggagaggc     120
cgggaccctg agatgggcgg caagcctcgg cggaagaacc cccaggaagg cctgtataac     180
gaactgcaga agacaagat ggccgaggcc tacagcgaga tcggcatgaa gggcgagcgg     240
aggcggggca agggccacga cggcctgtat cagggcctgt ccaccgccac caaggatacc     300
tacgacgccc tgcacatgca ggccctgccc ccaagg                               336
```

<210> SEQ ID NO 32
<211> LENGTH: 126
<212> TYPE: DNA
<213> ORGANISM: Artificial Sequence
<220> FEATURE:
<223> OTHER INFORMATION: Synthetic; 4-1BB signaling domain nucleotide
      sequence

<400> SEQUENCE: 32

```
aaacggggca aagaaaact cctgtatata ttcaaacaac catttatgag accagtacaa      60
actactcaag aggaagatgg ctgtagctgc cgatttccag aagaagaaga aggaggatgt     120
gaactg                                                               126
```

<210> SEQ ID NO 33
<211> LENGTH: 72
<212> TYPE: DNA
<213> ORGANISM: Artificial Sequence
<220> FEATURE:
<223> OTHER INFORMATION: Synthetic; T2A nucleotide sequence

<400> SEQUENCE: 33

```
ctcgagggcg gcggagaggg cagaggaagt cttctaacat gcggtgacgt ggaggagaat    60
cccggcccta gg                                                        72
```

<210> SEQ ID NO 34
<211> LENGTH: 1071
<212> TYPE: DNA
<213> ORGANISM: Artificial Sequence
<220> FEATURE:
<223> OTHER INFORMATION: Synthetic; EGFRt nucleotide sequence

<400> SEQUENCE: 34

```
atgcttctcc tggtgacaag ccttctgctc tgtgagttac cacacccagc attcctcctg    60
atcccacgca aagtgtgtaa cggaataggt attggtgaat taaagactc actctccata    120 aatgctacga atattaaaca cttcaaaaac tgcacctcca tcagtggcga tctccacatc    180
ctgccggtgg catttagggg tgactccttc acacatactc ctcctctgga tccacaggaa    240
ctggatattc tgaaaaccgt aaaggaaatc acagggtttt tgctgattca ggcttggcct    300
gaaaacagga cggacctcca tgcctttgag aacctagaaa tcatacgcgg caggaccaag    360
caacatggtc agttttctct tgcagtcgtc agcctgaaca taacatcctt gggattacgc    420
tccctcaagg agataagtga tggagatgtg ataatttcag gaaacaaaaa tttgtgctat    480
gcaaatacaa taaactggaa aaaactgttt gggacctccg tcagaaaac caaaattata    540 agcaacagag gtgaaaacag ctgcaaggcc acaggccagg tctgccatgc cttgtgctcc    600
cccgagggct gctggggccc ggagcccagg gactgcgtct cttgccggaa tgtcagccga    660
ggcagggaat gcgtggacaa gtgcaacctt ctggagggtg agccaaggga gtttgtggag    720
aactctgagt gcatacagtg ccacccagag tgcctgcctc aggccatgaa catcacctgc    780
acaggacggg gaccagacaa ctgtatccag tgtgcccact acattgacgg cccccactgc    840
gtcaagacct gcccggcagg agtcatggga gaaaacaaca ccctggtctg aagtacgca    900 gacgccggcc atgtgtgcca cctgtgccat ccaaactgca cctacggatg cactgggcca    960
ggtcttgaag gctgtccaac gaatgggcct aagatcccgt ccatcgccac tgggatggtg   1020
ggggccctcc tcttgctgct ggtggtggcc ctggggatcg gcctcttcat g            1071
```

METHODS AND COMPOSITIONS COMPRISING B7H3 CHIMERIC ANTIGEN RECEPTORS

PRIORITY AND CROSS REFERENCE TO RELATED APPLICATIONS

This application is a U.S. National Phase Application of PCT International Application Number PCT/US2019/048814, filed on Aug. 29, 2019, designating the United States of America and published in the English language, which is an International Application of and claims the benefit of priority to U.S. Provisional Application No. 62/725,599, filed on Aug. 31, 2018. The disclosures of the above-referenced applications are hereby expressly incorporated by reference in their entireties.

SEQUENCE LISTING IN ELECTRONIC FORMAT

The present application is being filed along with an Electronic Sequence Listing as an ASCII text file via EFS-Web. The Electronic Sequence Listing is provided as a file entitled SeqList-SCRI-170NP, created and last saved on Feb. 25, 2021, which is 16 KB in size. The information in the Electronic Sequence Listing is incorporated herein by reference in its entirety.

FIELD

Embodiments of the methods and compositions provided herein relate to chimeric antigen receptors (CARs) that specifically bind to B7H3. Some embodiments relate to cell-based immunotherapy targeting tumors, such as tumors comprising B7H3+ cells.

BACKGROUND

B7 Homolog 3 (B7H3), also known as CD276, is a type I transmembrane protein encoded by chromosome 15 in humans. The extracellular domain is composed of two identical pairs of an immunoglobulin variable domain and an immunoglobulin constant domain in humans (4IgB7-H3 isoform) due to exon duplication. The intracellular tail of B7H3 is short and has no known signaling motif. B7H3 is universally expressed among species. A soluble form, cleaved from the surface by a matrix metallopeptidase MMP or produced through alternative splicing of the intron, is also detectable in human sera.

B7H3 is induced on antigen presenting cells and plays an important role in the inhibition of T cell function. Importantly, B7H3 is highly overexpressed on a wide range of human solid cancers and often correlates with both negative prognosis and poor clinical outcome in patients. For example, numerous studies have described B7H3 overexpression in human malignancies, including melanoma, leukemia, breast, prostate, ovarian, pancreatic, colorectal, and other cancers. See e.g., Wang J, et al., J Invest Dermatol. 133:2050-8; Hu Y, et al., Hematology. 20:187-95; Sun J, et al., OncoTargets Ther. 7:1979-86; Zang X, et al., Proc Natl Acad Sci USA. 104:19458-63; Zang X et al, Mod Pathol. 23:1104-12; Chen Y, et al., OncoTargets Ther. 7:1465-72; and Ingebrigtsen V A et al., BMC Cancer. 14:602. As detected by immunochemistry, over 60% and up to 93% of patient tumor tissues display aberrant expression of B7H3 in the vast majority of cancer types, while limited expression is seen on normal healthy tissues. In most cases, a high expression of B7H3 is correlated with bad prognosis and poor clinical outcome. Accordingly, there is a need for improved therapies that target B7H3.

SUMMARY

Some embodiments of the methods and compositions provided herein include an isolated polynucleotide encoding a chimeric antigen receptor (CAR) comprising: a single-chain variable fragment (scFv), which specifically binds to B7H3; a transmembrane domain; a spacer between the scFv and the transmembrane domain; and an intracellular signaling domain.

In some embodiments, the scFv comprises: a heavy chain variable region (VH) CDR3 having at least 95% identity with the amino acid sequence of SEQ ID NO:03, and a light chain variable region (VL) CDR3 having at least 95% identity with the amino acid sequence of SEQ ID NO:06.

In some embodiments, the scFv comprises: a VH CDR1 having at least 95% identity with the amino acid sequence of SEQ ID NO:01, a VH CDR2 having at least 95% identity with the amino acid sequence of SEQ ID NO:02, a VL CDR1 having at least 95% identity with the amino acid sequence of SEQ ID NO:04, and a VL CDR2 having at least 95% identity with the amino acid sequence of SEQ ID NO:05.

In some embodiments, the scFv comprises a VH region having at least 95% identity with the amino acid sequence of SEQ ID NO:13.

In some embodiments, the scFv comprises a VL region having at least 95% identity with the amino acid sequence of SEQ ID NO:15.

In some embodiments, the spacer comprises an amino acid sequence of X1PPX2P.

In some embodiments, the spacer comprises a portion of a hinge region of a human antibody or modified variant thereof.

In some embodiments, the spacer comprises, consists of, or consists essentially of, an IgG4 hinge spacer having at least 95% identity with the amino acid sequence of SEQ ID NO:18.

In some embodiments, the spacer comprises, consists of, or consists essentially of, an IgG4 hinge-CH3 spacer having at least 95% identity with the amino acid sequence of SEQ ID NO:19.

In some embodiments, the spacer comprises, consists of, or consists essentially of, an IgG4 hinge-CH2-CH3 spacer having at least 95% identity with the amino acid sequence of SEQ ID NO:20.

In some embodiments, the spacer comprises, consists of, or consists essentially of, an IgG4 hinge-CH2 (L235D, N297Q)-CH3 spacer.

In some embodiments, the transmembrane domain comprises a CD28 transmembrane domain (CD28tm) having at least 95% identity with the amino acid sequence of SEQ ID NO:30.

In some embodiments, the intracellular signaling domain comprises primary and a costimulatory signaling domains optionally comprising all or a portion of a CD3 zeta in combination with a co-stimulatory domain selected from the group consisting of signaling domains of CD27, CD28, 4-1BB, OX-40, CD30, CD40, PD-1, ICOS, LFA-1, CD2, CD7, NKG2C, MyD88, and B7-H3 and combinations thereof.

In some embodiments, the intracellular signaling domain comprises a signaling portion of a CD3 zeta encoded by a nucleic acid having at least 95% identity with the nucleotide sequence of SEQ ID NO:31.

In some embodiments, the intracellular signaling domain comprises a signaling portion of a 4-1BB encoded by a nucleic acid having at least 95% identity with the nucleotide sequence of SEQ ID NO:32.

Some embodiments also include a nucleic acid encoding an identifier marker.

In some embodiments, the identifier marker is a truncated receptor. In some embodiments, the truncated receptor is selected from the group consisting of a truncated EGFR (EGFRt), a truncated HER2 (HER2t), and a truncated CD19 (CD19t).

Some embodiments also include a ribosomal skip sequence. In some embodiments, the ribosomal skip sequence comprises P2A or T2A.

Some embodiments also include a selectable marker suitable to select for a cell comprising the isolated polynucleotide. In some embodiments, the selectable marker comprises a dihydrofolate reductase transgene. In some embodiments, the dihydrofolate reductase transgene is a dihydrofolate reductase double mutant (DHFRdm). In some embodiments, the dihydrofolate reductase double mutant comprises amino acid mutations of L22F and F31S.

Some embodiments also include a nucleotide sequence encoding the VH CDR3 having at least 95% identity with SEQ ID NO:09, and a nucleotide sequence encoding the VL CDR3 having at least 95% identity with SEQ ID NO:12.

Some embodiments also include a nucleotide sequence encoding the VH CDR1 having at least 95% identity with SEQ ID NO:07, a nucleotide sequence encoding the VH CDR2 having at least 95% identity with SEQ ID NO:08, the VL CDR1 having at least 95% identity with SEQ ID NO:10, a nucleotide sequence encoding the VL CDR2 having at least 95% identity with SEQ ID NO:11.

Some embodiments also include a nucleotide sequence encoding the VH variable region amino acid sequence having at least 95% identity with SEQ ID NO:14.

Some embodiments also include a nucleotide sequence encoding the VL variable region amino acid sequence having at least 95% identity with SEQ ID NO:16.

Some embodiments of the methods and compositions provided herein include a protein encoded by the polynucleotide of any one of the foregoing embodiments related to isolated polynucleotides.

Some embodiments of the methods and compositions provided herein include a vector comprising the isolated polynucleotide of any one of the foregoing embodiments related to isolated polynucleotides.

In some embodiments, the vector is a viral vector.

In some embodiments, the vector is a lentiviral or adenoviral vector.

Some embodiments of the methods and compositions provided herein include a cell comprising the isolated polynucleotide of the foregoing embodiments related to isolated polynucleotides.

Some embodiments of the methods and compositions provided herein include a cell comprising the vector of any one of the foregoing embodiments related to vectors.

Some embodiments of the methods and compositions provided herein include a cell comprising a protein encoded by the isolated polynucleotide of any one of the foregoing embodiments related to isolated polynucleotides.

In some embodiments, the cell is selected from the group consisting of a CD8+ T cell, and a CD4+ T cell.

In some embodiments, the cell is a CD8+ T cytotoxic lymphocyte selected from the group consisting of a naïve CD8+ T cell, a central memory CD8+ T cell, an effector memory CD8+ T cell, and a bulk CD8+ T cell. In some embodiments, the CD8+ cytotoxic T lymphocyte cell is a central memory T cell and, wherein the central memory T cell is positive for CD45RO+, CD62L+, and CD8+.

In some embodiments, the cell is a CD4+ T helper lymphocyte cell selected from the group consisting of a naïve CD4+ T cell, a central memory CD4+ T cell, an effector memory CD4+ T cell, and a bulk CD4+ T cell. In some embodiments, the CD4+ helper lymphocyte cell is a naïve CD4+ T cell comprising CD45RA+, CD62L+ and CD4+, and lacks CD45RO.

In some embodiments, the cell is a precursor T cell.

In some embodiments, the cell is a hematopoietic stem cell.

Some embodiments of the methods and compositions provided herein include a pharmaceutical composition comprising the cell of any one of the foregoing embodiments related to cells, and a pharmaceutically acceptable excipient.

Some embodiments of the methods and compositions provided herein include a method of preparing the cell of any one of the foregoing embodiments related to cells comprising: introducing the isolated nucleic acid of any one of the foregoing embodiments related to an isolated nucleic acid into a lymphocyte; culturing the lymphocyte comprising the isolated nucleic acid in the presence of an agent selected from the group consisting of an anti-CD3 antibody, an anti-CD28 antibody, and a cytokine; and selectively enriching for the lymphocyte comprising the isolated nucleic acid.

In some embodiments, selectively enriching comprises contacting the lymphocyte comprising the isolated nucleic acid with a selection reagent. In some embodiments, the selection reagent comprises methotrexate.

In some embodiments, the lymphocyte has a CD45RA−, CD45RO+, and CD62L+ phenotype.

In some embodiments, the lymphocyte is a CD8+ lymphocyte or a CD4+ lymphocyte.

In some embodiments, the cytokine is selected from the group consisting of IL-15, 11-7, IL-2, and 11-21.

Some embodiments also include isolating a selectively enriched lymphocyte.

Some embodiments also include contacting the selectively enriched lymphocyte with an antibody against an identifier marker expressed by the lymphocyte.

In some embodiments, the identifier marker comprises a truncated receptor. In some embodiments, the truncated receptor is selected from the group consisting of a truncated EGFR (EGFRt), a truncated HER2 (HER2t), and a truncated CD19 (CD19t).

Some embodiments of the methods and compositions provided herein include a method of treating or ameliorating a subject having a tumor comprising a B7H3+ cell, the method comprising administering an effective amount of the cell of any one of the foregoing embodiments related to cells, to the subject.

In some embodiments, the cell is prepared from a cell of the subject.

In some embodiments, the administration is intravenous.

In some embodiments, the administration is locoregional at the site of the tumor in the subject.

In some embodiments, the tumor comprises a cancer selected from the group consisting of melanoma, leukemia, breast, prostate, ovarian, pancreatic, colorectal, endometrial, oral squamous cell carcinoma, cervical, non-small lung, bladder, clear cell renal cell carcinoma, and glioma.

In some embodiments, the tumor comprises a glioma. In some embodiments, the tumor comprises a glioma selected from the group consisting of oligodendroglioma, anaplastic astrocytoma, glioblastoma multiforme (GBM), ependymoma, and Diffuse intrinsic pontine glioma (DIPG). In some embodiments, the tumor comprises a glioblastoma multiforme (GBM).

Some embodiments also include administering an additional therapeutic regimen.

In some embodiments, the additional therapeutic regimen comprises radiation therapy.

In some embodiments, the additional therapeutic regimen comprises a chemotherapeutic compound. In some embodiments, the chemotherapeutic compound is selected from the group consisting of 2' deoxyazacitidine, 4-epi-doxorubicin, 5-aza-cytidine, 5-fluorouracil, 6-mercaptopurine, 6-thioguanine, Ara-C, BMS-214662, bortezomib, capecitabine, CHIR-258, cisplatin, cladribine, clofarabine, dacarbazine, decitabine, doxorubicin, etoposide, floxuridine, fludarabine, forodesine, FR01228, gemcitabine, hydroxyurea, KW-2449, lestautinib, lonafarnib, melphlan, midostaurin, mitomycin C, nelarabine, pentostatin, roscovitine, sapacitabine, semexanib, sodium valproate, sorafenib, sunitinib, tandutinib, teniposide, thiarabine, tipifarnib, trichostatin A, troxacitabine, vanadate, verapamil, vidaza, zosuquidar and trihydrochloride.

In some embodiments, administration of the cell and the administration of the additional therapeutic regimen are sequential.

In some embodiments, administration of the cell and the administration of the additional therapeutic regimen are concurrent.

In some embodiments, the subject is mammalian. In some embodiments, the subject is human.

Some embodiments of the methods and compositions provided herein include a cell for use in a medicament, the cell comprising a protein encoded by the isolated polynucleotide of any one of the foregoing embodiments related to isolated polynucleotides.

Some embodiments of the methods and compositions provided herein include a cell for use in treating a tumor comprising a B7H3+ cell in a subject.

In some embodiments, the tumor comprises a cancer selected from the group consisting of melanoma, leukemia, breast, prostate, ovarian, pancreatic, colorectal, endometrial, oral squamous cell carcinoma, cervical, non-small lung, bladder, clear cell renal cell carcinoma, and glioma. In some embodiments, the tumor comprises a glioma. In some embodiments, the tumor comprises a glioma selected from the group consisting of oligodendroglioma, anaplastic astrocytoma, glioblastoma multiforme (GBM), ependymoma, and intrinsic pontine glioma (DIPG). In some embodiments, the tumor comprises glioblastoma multiforme (GBM).

In some embodiments, the cell is selected from the group consisting of a CD8+ T cell, and a CD4+ T cell.

In some embodiments, the cell is a CD8+ T cytotoxic lymphocyte selected from the group consisting of a naïve CD8+ T cell, a central memory CD8+ T cell, an effector memory CD8+ T cell, and a bulk CD8+ T cell. In some embodiments, the CD8+ cytotoxic T lymphocyte cell is a central memory T cell and, wherein the central memory T cell is positive for CD45RO+, CD62L+, and CD8+.

In some embodiments, the cell is a CD4+ T helper lymphocyte cell selected from the group consisting of a naïve CD4+ T cell, a central memory CD4+ T cell, an effector memory CD4+ T cell, and a bulk CD4+ T cell. In some embodiments, the CD4+ helper lymphocyte cell is a naïve CD4+ T cell comprising CD45RA+, CD62L+ and CD4+, and lacks CD45RO.

In some embodiments, the cell is a precursor T cell.

In some embodiments, the cell is a hematopoietic stem cell.

Some embodiments of the methods and compositions provided herein include an isolated polynucleotide encoding a heavy chain variable region (VH) CDR3 having at least 95% sequence identity with the amino acid sequence of SEQ ID NO:03, and/or a light chain variable region (VL) CDR3 having at least 95% sequence identity with the amino acid sequence of SEQ ID NO:06.

Some embodiments of the methods and compositions provided herein include an isolated polynucleotide encoding a VH CDR1 having at least 95% sequence identity with the amino acid sequence of SEQ ID NO:01, a VH CDR2 having at least 95% sequence identity with the amino acid sequence of SEQ ID NO:02, a VL CDR1 having at least 95% sequence identity with the amino acid sequence of SEQ ID NO:04, and/or a VL CDR2 having at least 95% sequence identity with the amino acid sequence of SEQ ID NO:05.

Some embodiments of the methods and compositions provided herein include an isolated polynucleotide encoding a VH region having at least 95% sequence identity with the amino acid sequence of SEQ ID NO:13.

Some embodiments of the methods and compositions provided herein include an isolated polynucleotide encoding a VL region having at least 95% sequence identity with the amino acid sequence of SEQ ID NO:15.

Some embodiments of the methods and compositions provided herein include an isolated polypeptide or a composition comprising an isolated polypeptide, wherein said polypeptide comprises at least 95% sequence identity with the amino acid sequence of SEQ ID NO:01, SEQ ID NO:02, SEQ ID NO:03, SEQ ID NO:04, SEQ ID NO:05, SEQ ID NO:06, SEQ ID NO:13 or SEQ ID NO:15.

Some embodiments of the methods and compositions provided herein include a cell comprising the isolated polynucleotide of any one of the foregoing embodiments related to isolated polynucleotides or the polypeptide of any one of the foregoing embodiments related to polypeptides.

DEFINITIONS

Figure 1A:
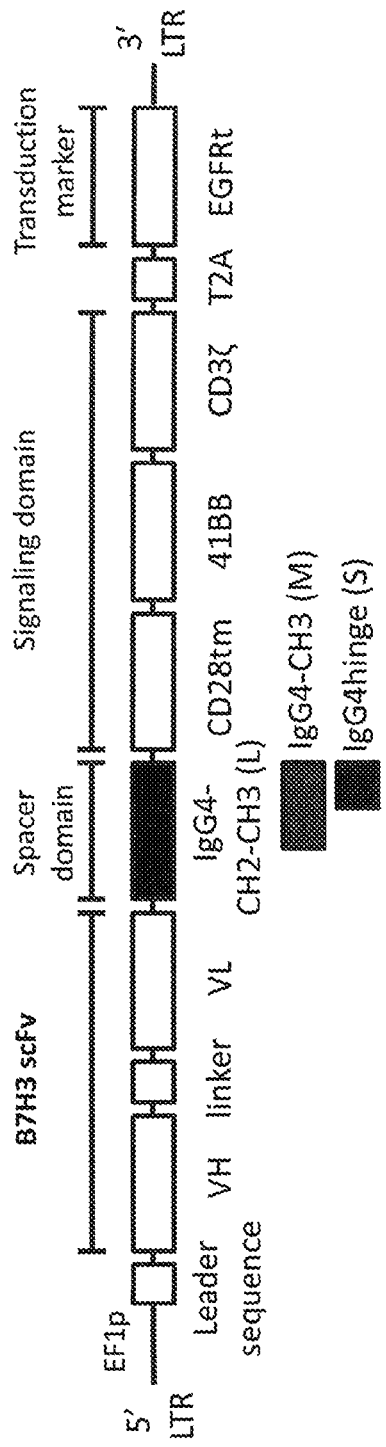
FIG. 1A is a schematic of polynucleotides encoding various B7H3 CARs.

As used herein, "nucleic acid" or "nucleic acid molecule" have their plain and ordinary meaning when read in light of the specification, and may include but is not limited to, for example, polynucleotides, such as deoxyribonucleic acid (DNA) or ribonucleic acid (RNA), oligonucleotides, fragments generated by the polymerase chain reaction (PCR), and/or fragments generated by any of ligation, scission, endonuclease action, and/or exonuclease action. Nucleic acid molecules can be composed of monomers that are naturally-occurring nucleotides (such as DNA or RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and/or azido groups, or sugars can be functionalized as ethers or esters. Moreover, the entire sugar moiety can be replaced with sterically and electronically similar structures, such as aza-sugars and/or carbocyclic sugar analogs. Examples of modifications in a base moiety include alkylated purines and/or pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid sequence encoding a protein is provided. In some alternatives, the nucleic acid is RNA or DNA.

As used herein, "antibody" has its plain and ordinary meaning when read in light of the specification, and may include but is not limited to, for example, a large Y-shape protein produced by plasma cells that is used by the immune system to identify and neutralize foreign objects such as bacteria and viruses. In some contexts, the term antibody refers to antigen binding fragments of an antibody. The antibody protein can comprise four polypeptide chains; two identical heavy chains and two identical light chains connected by disulfide bonds. Each chain is composed of structural domains called immunoglobulin domains. These domains can contain 70-110 amino acids and are classified into different categories according to their size and function. A chimeric antigen receptor can comprise a ligand binding domain, which includes an antibody fragment, preferably an antigen binding fragment. In some embodiments, a nucleic acid encoding a chimeric antigen receptor (CAR) is provided, the nucleic acid comprising: a) a first polynucleotide encoding a ligand binding domain, wherein the ligand binding domain binds to and/or interacts with a human B7H3 protein, b) a second polynucleotide encoding a polypeptide spacer of a length sufficient to allow the ligand binding domain to interact with the human B7H3 protein, c) a third polynucleotide encoding a transmembrane domain and d) a fourth polynucleotide encoding an intracellular signaling domain. In some alternatives, the ligand binding domain is an antibody fragment. Examples of an antibody or binding fragment thereof, which can be conjugated with target moieties, include monoclonal antibodies, bispecific antibodies, Fab, Fab2, Fab3, scFv, Bis-scFv, minibody, triabody, diabody, tetrabody, VhH domain, V-NAR domain, IgNAR or camel Ig. Additional examples of an antibody are IgG (e.g., IgG1, IgG2, IgG3, or IgG4), IgM, IgE, IgD, or IgA. Examples of antibodies include human antibodies, humanized antibodies, or chimeric antibodies.

As used herein, "single chain variable fragment" or scFv has its plain and ordinary meaning when read in light of the specification, and may include but is not limited to, for example, a fusion protein that comprises the variable regions of the heavy chain ($V_H$) and the light chains ($V_L$) of an immunoglobulin, which are connected to one another with a short linker peptide. In some embodiments, the linker can comprise glycine for flexibility and hydrophilic amino acids, for example serine or threonine for solubility. The linker can connect the N-terminus of the $V_H$ with the C-terminus of the VL or it can connect the C-terminus of the $V_H$ with the N-terminus of the $V_L$. In some embodiments, the ligand binding domain present on a CAR is a single chain variable fragment (scFv). In some embodiments, the scFv domain present on a CAR is specific for a B7H3 protein.

As used herein, "vector", "expression vector" or "construct" has its plain and ordinary meaning when read in light of the specification, and may include but is not limited to, for example, a nucleic acid used to introduce heterologous nucleic acids into a cell that has regulatory elements to provide expression of the heterologous nucleic acids in the cell. Vectors include but are not limited to plasmid, minicircles, yeast, and/or viral genomes. In some alternatives, the vectors are plasmid, minicircles, or viral genomes. In some alternatives, the vector is a viral vector. In some embodiments, the viral vector is a lentivirus. In some alternatives, the vector is a lentiviral vector. In some embodiments, the vector is a foamy viral vector, adenoviral vectors, retroviral vectors or lentiviral vectors.

As used herein, "chimeric antigen receptor" or "CAR" or "chimeric T cell receptor" have their plain and ordinary meaning when read in light of the specification, and may include but is not limited to, for example, a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). CARS are engineered receptors that can graft an arbitrary specificity onto an immune receptor cell. The term chimeric antigen receptors or "CARs" are also considered by some investigators to include the antibody or antibody fragment, the spacer, signaling domain, and transmembrane region. However, due to the surprising effects of modifying the different components or domains of the CAR described herein, such as the ligand binding region (for example, antibody fragment, scFv, or portion thereof), spacer, transmembrane domain, and/or signaling domain), the components of the CAR are frequently distinguished throughout this disclosure in terms of independent elements. In some alternatives, the spacer for the chimeric antigen receptor is selected (e.g., for a particular length of amino acids in the spacer) to achieve desired binding characteristics for the CAR. CARs having varying lengths of spacers, e.g., presented on cells are then screened for the ability to bind or interact with a target moiety to which the CAR is directed.

As used herein, T cells or T lymphocytes in some embodiments may include T cells from any mammalian, preferably primate, species, including monkeys, dogs, or humans. In some embodiments the T cells are allogeneic (from the same species but different donor) as the recipient subject who receives or is to receive the cells, such as in the form of a therapeutic composition; in some embodiments the T cells are autologous (the donor and the recipient are the same); in some embodiments the T cells are syngeneic (the donor and the recipients are different but are identical twins).

As used herein, mature T cells express the surface protein CD4 and are referred to as CD4+ T cells. CD4+ T cells are generally treated as having a pre-defined role as helper T cells within the immune system. For example, when an antigen-presenting cell expresses an antigen on MHC class II, a CD4+ cell will aid those cells through a combination of cell to cell interactions (e.g. CD40 and/or CD40L) and through cytokines. Nevertheless, there are rare exceptions; for example, sub-groups of regulatory T cells, natural killer cells, and cytotoxic T cells express CD4. All of the latter CD4+ expressing T cell groups are not considered T helper cells.

As used herein, "central memory" T cell (or "$T_{CM}$") has its plain and ordinary meaning when read in light of the specification, and may include but is not limited to, for example, an antigen experienced CTL that expresses CD62L or CCR-7 and/or CD45RO on the surface thereof, and does not express or has decreased expression of CD45RA as compared to naïve cells. In some embodiments, central memory cells are positive for expression of CD62L, CCR7, CD28, CD127, CD45RO, and/or CD95, and have decreased expression of CD54RA as compared to naïve cells.

As used herein, "effector" "$T_E$" T cells has its plain and ordinary meaning when read in light of the specification, and may include but is not limited to, for example, an antigen experienced cytotoxic T lymphocyte cells that do not express or have decreased expression of CD62L, CCR7, CD28, and/or are positive for granzyme B and/or perforin, as compared to central memory or naïve T cells.

As used herein, "T cell precursors" has its plain and ordinary meaning when read in light of the specification, and may include but is not limited to, for example, lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development, they become double-positive thymocytes (CD4$^+$CD8$^+$), and finally mature to single-positive (CD4$^+$CD8$^-$ or CD4$^-$CD8$^+$) thymocytes that are then released from the thymus to peripheral tissues.

As used herein, "pharmaceutical excipient," or pharmaceutical vehicle has its plain and ordinary meaning when read in light of the specification, and may include but is not limited to, for example, a carrier or inert medium used as a solvent in which the medicinally active agent or T cells for therapy is formulated and or administered. Vehicles can include polymeric micelles, liposomes, lipoprotein-based carriers, nano-particle carriers, dendrimers, and/or other vehicles for T cells that are known to one skilled in the art. An ideal vehicle or excipient can be non-toxic, biocompatible, non-immunogenic, biodegradable, and can avoid recognition by the host's defense mechanisms.

DETAILED DESCRIPTION

Some embodiments of the methods and compositions provided herein relate to chimeric antigen receptors (CARs)

that specifically bind to human B7 Homolog 3 (B7H3). Some embodiments relate to polynucleotides encoding CARs that specifically bind to B7H3, and cells expressing such CARs, and treating subjects having a B7H3+ tumor with such cells.

Some embodiments provided herein relate to B7H3 CARs and polynucleotides encoding such CARS. Some embodiments of the B7H3 CARs provided herein have particularly remarkable in vitro and in vivo activities. For example, certain embodiments of B7H3 CARs expressed in T cells have been demonstrated to have significantly increased activity to stimulate release of cytokines in vitro, to have significantly increased activity to inhibit growth of tumor cells in vivo, and to significantly increase the survival of a subject. Certain embodiments of B7H3 CARs expressed in T cells have also been demonstrated to have significant activity against several different types of central nervous system tumor cells in vitro, and to have significant activity in an in vivo xenograft model with human glioblastoma cells.

In some embodiments, a polynucleotide encoding a B7H3 CAR can be transduced into a T cell to generate a B7H3 CAR T cell. The transduced cell can express the B7H3 CAR and can target cells expressing the B7H3 antigen. In some embodiments, a T cell can be removed from a subject. The cell can be manipulated ex vivo to express a B7H3 CAR and re-introduced into the subject. The reintroduced cell can target tumor cells in the subject which express the B7H3 antigen. Some embodiments of the B7H3 CARS provided herein include a modified IgG4-hinge region which may enhance CAR stability and activity. In some embodiments, B7H3 CARS include a CD28 transmembrane region, and effector function through intracellular costimulatory molecule combinations. In some embodiments, a polynucleotide encoding a B7H3 CAR can encode a second polypeptide, such as an identifier marker, such as a truncated EGFR (EGFRt). Such identifier markers can be useful to isolate a cell co-expressing the identifier marker, and to measure the levels of cells expressing the identifier marker in a subject that has been treated with such cells. As described herein, B7H3 CARs have been successfully expressed in CD4 and CD8 T cells and confer potent and specific antitumor activity using a panel of in vitro and in vivo assays.

The use an scFv as a targeting moiety increases the complexity of CAR design as it relates to target and T-cell recognition. Whereas the classical interaction between a TCR and its cognate HLA molecule is spatially defined, CARs and their ability to identify targets depends on multiple parameters such as epitope location, target structure, and CAR extracellular spacer length and elasticity. The precise mechanisms that underlie the influence of variable extracellular spacer lengths on CAR engagement are still unknown. Aspects of this disclosure describe the incorporation of variable IgG4 heavy chain spacer lengths into B7H3 CARs to discover certain B7H3 CARs have significant and unexpected in vitro and in vivo activities.

Chimeric Antigen Receptors (CARs)

Some embodiments of the methods and compositions provided herein include B7H3 CARs and isolated polynucleotides encoding such B7H3 CARs. As used herein, "B7H3 CAR" relates to a CAR which targets a B7H3 antigen. In some embodiments a CAR can include a synthetically designed protein comprising an antigen binding domain that specifically binds a target, a spacer domain which links the antigen binding domain to a transmembrane domain, and an intracellular signaling domain. In some embodiments, the antigen binding domain can include an antibody, an antigen-binding fragment of an antibody, or a fusion protein derived from such an antibody, such as a single-chain variable fragment (scFv). A scFv can include a single chain Fv antibody in which the variable domains of the heavy chain and of the light chain of a traditional two chain antibody have been joined to form a single polypeptide chain. In some embodiments, the intracellular signaling domain can include a signaling domain and a co-stimulatory domain.

Some embodiments of the CARs provided herein include an antigen binding domain that specifically binds to a B7H3 antigen. In some embodiments, the antigen binding domain of a CAR can be derived from an antibody that specifically binds to B7H3. Examples of such antibodies are disclosed in Int. Pat. App. Pub. No WO 2011109400; U.S. Pat. Pub. 2013/0149236; and Loo D., et al., (2012) Clin Cancer Res; 18(14); 3834-45 which are each expressly incorporated by reference in their entirety. An antibody can include a heavy chain variable region ($V_H$) which can include a complementary determining region (CDR), such as a complementary determining region 1 (CDR1), a complementary determining region 2 (CDR2), and a complementary determining region 3 (CDR3). An antibody can include also include a light chain variable region ($V_L$) which can include a complementary determining region, such as an complementary determining region 1 (CDR1), a complementary determining region 2 (CDR2), and a complementary determining region 3 (CDR3).

In some embodiments, the antigen binding domain of a CAR which specifically binds to B7H3 can include at least a $V_H$ CDR3 derived from an antibody which specifically binds to B7H3, and/or a $V_H$ CDR1 derived from an antibody which specifically binds to B7H3, and/or a $V_H$ CDR2 derived from an antibody which specifically binds to B7H3. In some embodiments, the antigen binding domain of a CAR which specifically binds to B7H3 can include at least a $V_H$ region derived from an antibody which specifically binds to B7H3. In some embodiments, the antigen binding domain of a CAR which specifically binds to B7H3 can include at least a $V_L$ CDR3 derived from an antibody which specifically binds to B7H3, and/or a $V_L$ CDR1 derived from an antibody, which specifically binds to B7H3, and/or a $V_L$ CDR2 derived from an antibody which specifically binds to B7H3. In some embodiments, the antigen binding domain of a CAR which specifically binds to B7H3 can include at least a $V_L$ region derived from an antibody which specifically binds to B7H3.

In some embodiments, the antigen binding domain of a CAR which specifically binds to B7H3 includes a scFv derived from an antibody which specifically binds to B7H3. In some embodiments, the scFv includes a $V_H$ CDR3, and/or a $V_H$ CDR1, and/or a $V_H$ CDR2, derived from an antibody which specifically binds to B7H3. In some embodiments, the scFv includes a $V_H$ region derived from an antibody which specifically binds to B7H3. In some embodiments, the scFv includes a $V_L$ CDR3, and/or a $V_L$ CDR1, and/or a $V_L$ CDR2, derived from an antibody which specifically binds to B7H3. In some embodiments, the scFv includes a $V_L$ region derived from an antibody which specifically binds to B7H3. In some embodiments, the scFv includes both a $V_H$ region and $V_L$ region, each derived from an antibody which specifically binds to B7H3, or CDR elements of such a $V_H$ region and $V_L$ region. The $V_H$ region and $V_L$ region can be joined to each other through a linker. The $V_H$ region and $V_L$ region can be joined in either a $V_H$-$V_L$, or a $V_H$-$V_L$ orientation with respect to one another.

TABLE 1 lists example amino acid sequences and nucleotide sequences useful with embodiments of the methods and compositions provided herein.

TABLE 1

| Description | Sequence |
|---|---|
| SEQ ID NO: 01<br>V$_H$ CDR1 polypeptide | FGMH |
| SEQ ID NO: 02<br>V$_H$ CDR2 polypeptide | YISSDSSAIYYADTVK |
| SEQ ID NO: 03<br>V$_H$ CDR3 polypeptide | GRENIYYGSRLDY |
| SEQ ID NO: 04<br>V$_L$ CDR1 polypeptide | KASQNVDTNVA |
| SEQ ID NO: 05<br>V$_L$ CDR2 polypeptide | SASYRYS |
| SEQ ID NO: 06<br>V$_L$ CDR3 polypeptide | QQYNNYPFT |
| SEQ ID NO: 07<br>V$_H$ CDR1 nucleic acid | tttggaatgcac |
| SEQ ID NO: 08<br>V$_H$ CDR2 nucleic acid | tacattagta gtgacagtag tgccatctac tatgcagaca cagtgaag |
| SEQ ID NO: 09<br>V$_H$ CDR3 nucleic acid | gggagggaaa acatttacta cggtagtagg cttgactac |
| SEQ ID NO: 10<br>V$_L$ CDR1 nucleic acid | aaggccagtc agaatgtgga tactaatgta gcc |
| SEQ ID NO: 11<br>V$_L$ CDR2 nucleic acid | tcggcatcct accggtacag t |
| SEQ ID NO: 12<br>V$_L$ CDR3 nucleic acid | cagcaatata acaactatcc attcacg |
| SEQ ID NO: 13<br>V$_H$ region polypeptide | DVQLVESGGG LVQPGGSRKL SCAASGFTFS<br>SFGMHWVRQA PEKGLEWVAY ISSDSSAIYY<br>ADTVKGRFTI SRDNPKNTLF LQMTSLRSED<br>TAMYYCGRGR ENIYYGSRLD YVVGQGTTLTV SS |
| SEQ ID NO: 14<br>V$_H$ region nucleic acid | gatgtgcagc tggtggagtc tgggggaggc ttagtgcagc ctggagggtc<br>ccggaaactc tcctgtgcag cctctggatt cactttcagt agctttggaa tgcactgggt<br>tcgtcaggct ccagagaagg ggctggagtg gtcgcatac attagtagtg<br>acagtagtgc catctactat gcagacacag tgaagggccg attcaccatc<br>tccagagaca tcccaagaa caccctgttc ctgcaaatga ccagtctaag<br>gtctgaggac acggccatgt attactgtgg aagagggagg gaaaacattt<br>actacggtag taggcttgac tactggggcc aaggcaccac tctcacagtc tcctca |
| SEQ ID NO: 15<br>V$_L$ region polypeptide | DIAMTQSQKF MSTSVGDRVS VTCKASQNVD<br>TNVAWYQQKP GQSPKALIYS ASYRYSGVPD<br>RFTGSGSGTD FTLTINNVQS EDLAEYFCQQ<br>YNNYPFTFGS GTKLEIK |
| SEQ ID NO: 16<br>V$_L$ region nucleic acid | gacattgcga tgacccagtc tcaaaaattc atgtccacat cagtaggaga<br>cagggtcagc gtcacctgca aggccagtca gaatgtggat actaatgtag<br>cctggtatca acagaaacca gggcaatctc ctaaagcact gatttactcg<br>gcatcctacc ggtacagtgg agtccctgat cgcttcacag gcagtggatc<br>tgggacagat ttcactctca ccatcaacaa tgtgcagtct gaagacttgg cagagtattt<br>ctgtcagcaa tataacaact atccattcac gttcggctcg ggacaaagt<br>tggaaataaa a |

In some embodiments, a CAR which specifically binds to B7H3 can include a V$_H$ CDR1 which comprises or consists of an amino acid sequence having at least 90%, 91%, 92%, 93%, 94%, 95%, 96%, 97%, 98%, 99% or 100% identity with SEQ ID NO:01. In some embodiments, a V$_H$ CDR1 can be encoded by a nucleotide sequence having at least 90%, 91%, 92%, 93%, 94%, 95%, 96%, 97%, 98%, 99% or 100% identity with SEQ ID NO:07.

In some embodiments, a CAR which specifically binds to B7H3 can include a V$_H$ CDR2 which comprises or consists of an amino acid sequence having at least 90%, 91%, 92%, 93%, 94%, 95%, 96%, 97%, 98%, 99% or 100% identity with SEQ ID NO:02. In some embodiments, a V$_H$ CDR2 can be encoded by a nucleotide sequence having at least 90%, 91%, 92%, 93%, 94%, 95%, 96%, 97%, 98%, 99% or 100% identity with SEQ ID NO:08.

In some embodiments, a CAR which specifically binds to B7H3 can include a V$_H$ CDR3 which comprises or consists of an amino acid sequence having at least 90%, 91%, 92%, 93%, 94%, 95%, 96%, 97%, 98%, 99% or 100% identity with SEQ ID NO:03. In some embodiments, a V$_H$ CDR3 can be encoded by a nucleotide sequence having at least 90%, 91%, 92%, 93%, 94%, 95%, 96%, 97%, 98%, 99% or 100% identity with SEQ ID NO:09.

In some embodiments, a CAR which specifically binds to B7H3 can include a $V_H$ region which comprises or consists of an amino acid sequence having at least 90%, 91%, 92%, 93%, 94%, 95%, 96%, 97%, 98%, 99% or 100% identity with SEQ ID NO:13. In some embodiments, a $V_H$ region can be encoded by a nucleotide sequence having at least 90%, 91%, 92%, 93%, 94%, 95%, 96%, 97%, 98%, 99% or 100% identity with SEQ ID NO:14.

In some embodiments, a CAR which specifically binds to B7H3 can include a $V_L$ CDR1 which comprises or consists of an amino acid sequence having at least 90%, 91%, 92%, 93%, 94%, 95%, 96%, 97%, 98%, 99% or 100% identity with SEQ ID NO:04. In some embodiments, a $V_L$ CDR1 can be encoded by a nucleotide sequence having at least 90%, 91%, 92%, 93%, 94%, 95%, 96%, 97%, 98%, 99% or 100% identity with SEQ ID NO:10.

In some embodiments, a CAR which specifically binds to B7H3 can include a $V_L$ CDR2 which comprises or consists of an amino acid sequence having at least 90%, 91%, 92%, 93%, 94%, 95%, 96%, 97%, 98%, 99% or 100% identity with SEQ ID NO:05. In some embodiments, a $V_L$ CDR2 can be encoded by a nucleotide sequence having at least 90%, 91%, 92%, 93%, 94%, 95%, 96%, 97%, 98%, 99% or 100% identity with SEQ ID NO:11.

In some embodiments, a CAR which specifically binds to B7H3 can include a $V_L$ CDR3 which comprises or consists of an amino acid sequence having at least 90%, 91%, 92%, 93%, 94%, 95%, 96%, 97%, 98%, 99% or 100% identity with SEQ ID NO:06. In some embodiments, a $V_L$ CDR3 can be encoded by a nucleotide sequence having at least 90%, 91%, 92%, 93%, 94%, 95%, 96%, 97%, 98%, 99% or 100% identity with SEQ ID NO:12.

In some embodiments, a CAR which specifically binds to B7H3 can include a $V_L$ region which comprises or consists of an amino acid sequence having at least 90%, 91%, 92%, 93%, 94%, 95%, 96%, 97%, 98%, 99% or 100% identity with SEQ ID NO:15. In some embodiments, a $V_L$ region can be encoded by a nucleotide sequence having at least 90%, 91%, 92%, 93%, 94%, 95%, 96%, 97%, 98%, 99% or 100% identity with SEQ ID NO:16.

In some embodiments, a percent identity between two sequences, such as two amino acid sequences or two nucleotide sequences can be determined, for example, by aligning the sequences for optimal comparison purposes, such as gaps can be introduced in the sequence of a first sequence. The amino acids or nucleotides at corresponding positions are then compared, and the percent identity between the two sequences is a function of the number of identical positions shared by the sequences, for example, % identity=# of identical positions/total # of positions ×100. The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. In some embodiments of the methods and compositions provided herein, a nucleic acid sequence of a polynucleotide encoding a CAR or component thereof, can consist of, consist essentially of, or comprise a nucleotide sequence having at least 90%, 91%, 92%, 93%, 94%, 95%, 96%, 97%, 98%, 99% or 100% identity with a nucleotide sequence provided herein. In some embodiments of the methods and compositions provided herein, an amino acid sequence of a CAR polypeptide or component thereof can consist of, consist essentially of, or comprise an amino acid sequence having at least 90%, 91%, 92%, 93%, 94%, 95%, 96%, 97%, 98%, 99% or 100% identity with an amino acid sequence provided herein.

In some embodiments, an amino acid sequence can include a conservative amino acid substitution. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered conservative substitutions even if the residues are in different groups, such as replacement of phenylalanine with the smaller isoleucine. In some embodiments, a conservative amino acid substitution can include the use of amino acid analogs or variants. TABLE 2 lists example families of conservative amino acid substitutions.

TABLE 2

| Family | Amino Acids |
| --- | --- |
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

In some embodiments, a B7H3 CAR can include a spacer domain which links the antigen binding domain to a transmembrane domain. In some embodiments, a spacer domain of appropriate length can convey mobility the antigen binding domain to allow for optimal binding to a target antigen. Example spacer domains useful with some embodiments of the methods and compositions provided herein are described in Int. Pat. App. Pub. No. WO 2014031687; U.S. Pat. Pub. 20180200298; and Kunkele A., et al. (2015) Cancer Immunol Res; 3(4); 368-79 which are each incorporated by reference in its entirety.

In some embodiments, a spacer domain can be derived from at least a portion of a hinge region of an IgG1, IgG2, IgG3, or IgG4. In some embodiments, a spacer domain can be derived from a CH2 region and/or CH3 region of an IgG1, IgG2, IgG3, or IgG4. In some embodiments, a spacer domain can include upper hinge amino acids found between the variable heavy chain and the core, and the core hinge amino acids including a polyproline region. In some embodiments, the upper hinge region has or has about 3, 4, 5, 6, 7, 8, 9, or 10 amino acids. In some embodiments, the spacer region comprises an amino acid sequence of $X_1PPX_2P$ (SEQ ID NO:17). In some embodiments, $X_1$ is a cysteine, glycine, or arginine and $X_2$ is a cysteine or a threonine. In some embodiments, a spacer domain can include a modified hinge region of an IgG. For example, a modified hinge region can have at least 90%, 92%, 95%, or 100% sequence identity or a sequence identity within a range defined by any two of the aforementioned percentages, with a hinge region of an IgG.

In some embodiments, a spacer region can have a length of at least or at least about 10 to 229 amino acids, at least or at least about 10 to 200 amino acids, at least or at least about 10 to 175 amino acids, at least or at least about 10 to 150 amino acids, at least or at least about 10 to 125 amino acids, at least or at least about 10 to 100 amino acids, at least or at least about 10 to 75 amino acids, at least or at least about 10 to 50 amino acids, at least or at least about 10 to 40 amino acids, at least or at least about 10 to 30 amino acids, at least or at least about 10 to 20 amino acids, or at least or at least about 10 to 15 amino acids, and including any integer between the endpoints of any of the listed ranges. In some embodiments, a spacer region has 12 amino acids or less (but not zero) or about 12 amino acids or less (but not zero), comprise, consists of, or consist essentially of a human IgG4 hinge-CH2 (L235D, N297Q)-CH3 spacer. TABLE 3 lists example amino acid sequences of spacer domains useful with embodiments of the methods and compositions provided herein. In some embodiments, a spacer region can comprise an amino acid sequence having at least 90%, 91%, 92%, 93%, 94%, 95%, 96%, 97%, 98%, 99% or 100% identity with any one of the amino acid sequences listed in TABLE 3.

TABLE 3

| Description | Sequence |
|---|---|
| SEQ ID NO: 18<br>Small (S) spacer | ESKYGPPCPPCP |
| SEQ ID NO: 19<br>Medium (M) spacer | ESKYGPPCPPCPGQPREPQVYTLPPSQEEMTKNQVSLTCL<br>VKGFYPSDIAVEWESNGQPENNYKTTPPVLDSDGSFFLYS<br>RLTVDKSRWQEGNVFSCSVMHEALHNHYTQKSLSLSLG<br>K |
| SEQ ID NO: 20<br>Long (L) spacer | ESKYGPPCPPCPAPEFLGGPSVFLFPPKPKDTLMISRTPEV<br>TCVVVDVSQEDPEVQFNWYVDGVEVHNAKTKPREEQFN<br>STYRVVSVLTVLHQDWLNGKEYKCKVSNKGLPSSIEKTIS<br>KAKGQPREPQVYTLPPSQEEMTKNQVSLTCLVKGFYPSDI<br>AVEWESNGQPENNYKTTPPVLDSDGSFFLYSRLTVDKSR<br>WQEGNVFSCSVMHEALHNHYTQKSLSLSLGK |
| SEQ ID NO: 21<br>Human IgG1 hinge | EPKSCDKTHTCPPCP |
| SEQ ID NO: 22<br>Human IgG2 hinge | ERKCCVECPPCP |
| SEQ ID NO: 23<br>Human IgG3 hinge | ELKTPLGDTHTCPRCP |
| SEQ ID NO: 24<br>Human IgG4 hinge | ESKYGPPCPSCP |
| SEQ ID NO: 25<br>Modified human IgG4 hinge | ESKYGPPCPPCP |
| SEQ ID NO: 26<br>Modified human IgG4 hinge | YGPPCPPCP |
| SEQ ID NO: 27<br>Modified human IgG4 hinge | KYGPPCPPCP |
| SEQ ID NO: 28<br>Modified human IgG4 hinge | EVVKYGPPCPPCP |

119 amino acids or less (but not zero) or about 119 amino acids or less (but not zero), or 229 amino acids or less (but not zero) or about 229 amino acids or less (but not zero).

In some embodiments, a spacer region can comprise, consists of, or consist essentially of, a human IgG4 hinge spacer. In some embodiments, a spacer region can comprise, consists of, or consist essentially of, a polypeptide having an amino acid sequence of SEQ ID NO:18. In some embodiments, a spacer region can comprise, consists of, or consist essentially of, a human IgG4 hinge-CH3 spacer. In some embodiments, a spacer region can comprise, consists of, or consist essentially of, a polypeptide having an amino acid sequence of SEQ ID NO:19. In some embodiments, a spacer region can comprise, consists of, or consist essentially of a human IgG4 hinge-CH3-CH4 spacer. In some embodiments, a spacer region can comprise, consists of, or consist essentially of, a polypeptide having an amino acid sequence of SEQ ID NO:20. In some embodiments, a spacer region can In some embodiments, a B7H3 CAR can include a transmembrane domain. A transmembrane domain can provide anchoring of a CAR in a cell membrane. In some embodiments, the transmembrane domain can be derived from a membrane-bound or transmembrane protein. In some embodiments, the transmembrane domain can have a length of or of about 10, 11, 12, 13, 14, 15, 16, 17, 18, 19, 20, 21, 22, 23, 24, 25, 26, 27, or 28 amino acids. In some embodiments, a transmembrane domain can include a transmembrane region of an alpha, beta or zeta chain of a T-cell receptor, such as CD28, CD3, CD45, CD4, CD8, CD9, CD16, CD22, CD33, CD37, CD64, CD80, CD86, CD134, CD137 or CD154. In some embodiments, the transmembrane domain can be derived from a CD28 transmembrane domain (CD28tm). TABLE 4 lists example an amino acid and nucleotide sequence of a CD28tm domain useful with embodiments of the methods and compositions provided herein. In some embodiments, a transmembrane domain can be encoded by a nucleotide sequence having at least 90%, 91%, 92%, 93%, 94%, 95%, 96%, 97%, 98%, 99% or 100% identity with SEQ ID NO:29.

TABLE 4

| Description | Sequence |
|---|---|
| SEQ ID NO: 29<br>CD28tm nucleotide sequence | atgttctgggtgctggtggtggtcggaggcgtgctggcctgctacagcctgctgg<br>tcaccgtggccttcatcatctttgggtg |
| SEQ ID NO: 30<br>CD28tm amino acid sequence | MFWVLVVVGGVLACYSLLVTVAFIIFWV |

In some embodiments, a B7H3 CAR can include an intracellular signaling domain linked to a transmembrane domain. The intracellular signaling domain can activate a function of a cell when the antigen binding domain binds to a target antigen. In some embodiments, the intracellular signaling domain can activate a function of a cell expressing a CAR, such as a T cell expressing the CAR. In some embodiments, the intracellular signaling domain contains one or more intracellular signaling domains. In some embodiments, the intracellular signaling domain can include a domain derived from at least a portion of an intracellular signaling domain that provides for activation of at least one function of the transduced cell, such as a T cell. T cell activation can be mediated by at least two classes of intracellular signaling proteins: those that initiate antigen-dependent primary activation and provide a T cell receptor like signal, such as primary cytoplasmic signaling proteins; and those that act in an antigen-independent manner to provide a secondary or co-stimulatory signal, such as secondary cytoplasmic signaling proteins. In some embodiments an intracellular signaling domain can include a functional domain of a primary cytoplasmic signaling protein. In some embodiments an intracellular signaling domain can include a functional domain of a primary cytoplasmic signaling protein, and at least one functional domain of one or more secondary cytoplasmic signaling proteins.

In some embodiments, the signaling domains, such as primary signaling domains or costimulatory domains, include an intracellular or cytoplasmic domain of a protein or a receptor protein that interacts with components within the interior of the cells and is capable of relaying or participating in the relaying of a signal. Such interactions in some embodiments can occur through the intracellular domain communicating via specific protein-protein or protein-ligand interactions with an effector molecule or an effector protein, which in turn can send the signal along a signal chain to its destination. In some embodiments, the signaling domain includes a co-stimulatory domain. In some aspects, the costimulatory domain includes a signaling moiety that provides to T-cells a signal which, in addition to the primary signal provided by for instance the CD3 zeta chain of the TCR/CD3 complex, enhances response such as a T-cell effector response, such as, for example, an immune response, activation, proliferation, differentiation, cytokine secretion, cytolytic activity, perforin and/or granzyme activity and the like. In some embodiments, the intracellular signaling domain and/or the co-stimulatory domain can include all or a portion of CD27, CD28, 41BB, OX40, CD30, CD40, ICOS, lymphocyte function-associated antigen-1 (LFA-1), CD2, CD7, LIGHT, NKG2C, or B7H3, and/or a ligand that specifically binds with CD83.

Primary cytoplasmic signaling proteins that act in a stimulatory manner may contain signaling motifs which are known as intracellular receptor tyrosine-based activation motifs (ITAMs). Examples of ITAMs containing primary cytoplasmic signaling domains include those derived from CD3 zeta, FcR gamma, CD3 gamma, CD3 delta, CD3 epsilon, CD5, CD22, CD79a, CD79b, or CD66d.

In some embodiments, the intracellular signaling domain can include all or a portion of the signaling domain of CD3-zeta or variant thereof and all or a portion of the signaling domain of 4-1BB or variant thereof. TABLE 5 lists example nucleotide sequences encoding a signaling domain of CD3-zeta, and a signaling domain of 4-1BB. In some embodiments, an intracellular signaling domain can comprise an amino acid sequence encoded by a nucleic acid having at least 90%, 91%, 92%, 93%, 94%, 95%, 96%, 97%, 98%, 99% or 100% identity with any one of the amino acid sequences listed in TABLE 5.

TABLE 5

| Description | Sequence |
|---|---|
| SEQ ID NO: 31<br>CD3-zeta signaling domain<br>nucleotide sequence | cgggtgaagttcagcagaagcgccgacgcccctgcctaccagcagggccaga<br>atcagctgtacaacgagctgaacctgggcagaagggaagagtacgacgtcctg<br>gataagcggagaggccgggaccctgagatgggcggcaagcctcggcggaag<br>aaccccaggaaggcctgtataacgaactgcagaaagacaagatggccgagg<br>cctacagcgagatcggcatgaagggcgagcggaggcggggcaagggccacg<br>acggcctgtatcagggcctgtccaccgccaccaaggatacctacgacgccctgc<br>acatgcaggccctgcccccaagg |
| SEQ ID NO: 32<br>4-1BB signaling domain<br>nucleotide sequence | aaacggggcagaaagaaactcctgtatatattcaaacaaccatttatgagaccagt<br>acaaactactcaagaggaagatggctgtagctgccgatttccagaagaagaaga<br>aggaggatgtgaactg |
| SEQ ID NO: 33<br>T2A nucleotide sequence | ctcgagggcggcggagagggcagaggaagtcttctaacatgcggtgacgtgg<br>aggagaatcccggccctagg |
| SEQ ID NO: 34<br>EGFRt nucleotide sequence | atgcttctcctggtgacaagccttctgctctgtgagttaccacacccagcattcctc<br>ctgatcccacgcaaagtgtgtaacggaataggtattggtgaatttaaagactcact<br>ctccataaatgctacgaatattaaacacttcaaaaactgcacctccatcagtggcg |

TABLE 5-continued

| Description | Sequence |
|---|---|
| | atctccacatcctgccggtggcatttaggggtgactccttcacacatactcctcctc<br>tggatccacaggaactggatattctgaaaaccgtaaaggaaatcacagggtttttg<br>ctgattcaggcttggcctgaaaacaggacggacctccatgcctttgagaacctag<br>aaatcatacgcggcaggaccaagcaacatggtcagttttctcttgcagtcgtcagc<br>ctgaacataacatccttgggattacgctccctcaaggagataagtgatggagatgt<br>gataatttcaggaaacaaaaatttgtgctatgcaaatacaataaactggaaaaaact<br>gtttgggacctccggtcagaaaaccaaaattataagcaacagaggtgaaaacag<br>ctgcaaggccacaggccaggtctgccatgccttgtgctcccccgagggctgctg<br>gggcccggagcccagggactgcgtctcttgccggaatgtcagccgaggcagg<br>gaatgcgtggacaagtgcaaccttctggagggtgagccaagggagtttgtggag<br>aactctgagtgcatacagtgccacccagagtgcctgcctcaggccatgaacatca<br>cctgcacaggacggggaccagacaactgtatccagtgtgcccactacattgacg<br>gcccccactgcgtcaagacctgcccggcaggagtcatgggagaaaacaacac<br>cctggtctggaagtacgcagacgccggccatgtgtgccacctgtgccatccaaa<br>ctgcacctacggatgcactgggccaggtcttgaaggctgtccaacgaatgggcc<br>taagatcccgtccatcgccactgggatggtgggggccctcctcttgctgctggtg<br>gtggccctggggatcggcctcttcatg |

In some embodiments, a polynucleotide encoding a B7H3 CAR can be multicistronic, and encode more than one polypeptide. In some embodiments, a polynucleotide encoding a CAR can include an element to permit translation of multiples genes from a single polynucleotide. In some embodiments, the element can include an internal ribosome entry site (IRES), or a ribosome skip sequence. A ribosome skip sequence can include a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. In some alternatives, the ribosome skip sequence is a P2A, T2A, E2A or F2A sequence. In some alternatives, the ribosome skip sequence is a T2A sequence. TABLE 5 lists an example T2A nucleotide sequence useful with embodiments of the methods and compositions provided herein.

In some embodiments, a polynucleotide encoding a CAR can have an IRES or a ribosome skip sequence between a nucleotide sequence encoding the CAR, and a nucleotide sequence encoding a second polypeptide. In some embodiments, the CAR and second polypeptide can be co-expressed in a cell. In some embodiments, the second polypeptide can encode an identifier marker and/or selectable marker, such as a protein that can be used to identify, isolate and/or enrich for a cell expressing the identifier marker and/or selectable marker. Examples of such markers include truncated receptors which can be used to identify an expressing cells, yet have minimal activity. An example truncated receptor includes truncated epidermal growth factor receptor (EGFRt), which is described in U.S. Pat. No. 8,802,374, which is incorporated by reference in its entirety. TABLE 5 lists an example nucleotide sequence encoding an EGFRt useful with embodiments of the methods and compositions provided herein. More examples of truncated receptors include truncated HER2 (HER2t), and a truncated CD19 (CD19t). Examples of selectable markers include a dihydrofolate reductase transgene. In some embodiments, the dihydrofolate reductase can be a dihydrofolate reductase double mutant (DHFRdm). In some such embodiments, the dihydrofolate reductase double mutant comprises amino acid mutations of L22F and F31S. More examples of selectable markers include hygromycin-B phosphotransferase gene (hph) which confers resistance to hygromycin B, the amino glycoside phosphotransferase gene (neo or aph) from Tn5 which codes for resistance to the antibiotic G418, and the adenosine deaminase gene (ADA). In some embodiments, an identifier marker, such as EGFRt, can be used to isolate a population of cells. In some embodiments, antibodies against an identifier marker can capture cells expressing the identifier marker, such as EGFRt. The antibodies can include a first binding partner, such as biotin or streptavidin. The antibodies can be captured with a second binding partner, such as biotin or streptavidin, attached to a substrate, such as a bead, such as a magnetic bead. In some embodiments, an identifier marker, such as EGFRt, can be used to measure the levels of CAR T cells in a subject that has been administered the CAR T cells.

Some embodiments of the methods and compositions provided herein can include a vector containing an isolated polynucleotide encoding a CAR which specifically binds to B7H3. In some embodiments, the vector is a viral vector. In some embodiments, the vector is a lentiviral or adenoviral vector.

Methods of Preparing CAR T Cells

Some embodiments of the methods and compositions provided herein can include a cell comprising a polynucleotide encoding a B7H3 CAR and methods for making these compositions. Some such embodiments include, for example, introducing an isolated polynucleotide encoding a B7H3 CAR into a lymphocyte, culturing the lymphocyte comprising the isolated polynucleotide in the presence of an agent that promotes expansion of a cell population comprising the isolated polynucleotide, such as an agent selected from the group consisting of an anti-CD3 antibody, an anti-CD28 antibody, and a cytokine; and selectively enriching for the lymphocyte comprising the isolated polynucleotide. In some embodiments, selectively enriching comprises contacting the lymphocyte comprising the isolated nucleic acid with a selection reagent. In some embodiments, the selection reagent comprises methotrexate. In some embodiments, the lymphocyte has a CD45RA−, CD45RO+, and CD62L+ phenotype. In some embodiments, the lymphocyte is a CD8+ lymphocyte or a CD4+ lymphocyte. In some embodiments, the cytokine is selected from the group consisting of IL-15, Il-7, IL-2, and Il-21. Some embodiments also include isolating a selectively enriched lymphocyte. In some embodiments, contacting the selectively enriched lymphocyte with an antibody against an identifier marker expressed by the lymphocyte. In some embodiments, the identifier marker comprises a truncated receptor. In some embodiments, the truncated receptor is selected from the group consisting of a truncated EGFR (EGFRt), a truncated HER2 (HER2t), and a truncated CD19 (CD19t). Example methods are described in U.S. Pat. Pub. 20180200298, which is incorporated by reference in its entirety.

Some embodiments of the methods and compositions provided herein can include selection and sorting of T lymphocyte populations and modification of T lymphocyte populations. In some embodiments for the selection and sorting of T lymphocyte populations, T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques, such as those described in U.S. Pat. No. 6,040,177, which is incorporated by reference in its entirety. In some embodiments, the T cells are autologous T cells obtained from the patient.

In some embodiments, a desired T cell population or subpopulation may be expanded by adding an initial T lymphocyte population to a culture medium in vitro, and then adding to the culture medium feeder cells, such as non-dividing peripheral blood mononuclear cells (PBMC). The non-dividing feeder cells can comprise gamma-irradiated PBMC feeder cells. In some embodiments, the PBMC are irradiated with gamma rays. In some embodiments, an expansion method can include adding non-dividing EBV-transformed lymphoblastoid cells (LCL) as feeder cells. LCL can be irradiated with gamma rays. In some embodiments, an expansion method can include adding anti-CD3 and/or anti CD28 antibody to the culture medium. In some embodiments, an expansion method can include adding IL-2 and/or IL-15 to the culture medium (e.g., wherein the concentration of IL-2 is at least about 10 units/ml). In some embodiments, the expanded T lymphocytes can include CD8+ cytotoxic T lymphocytes (CTL) and CD4+ helper T lymphocytes that may be specific for an antigen present on a human tumor or a pathogen. After initial isolation of T lymphocytes both cytotoxic and helper T lymphocytes can be sorted into naive, memory, and effector T cell subpopulations either before or after expansion.

CD8+ cells can be obtained by using standard methods. In some embodiments, CD8+ cells are further sorted into naive, central memory, and effector memory cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and/or CD127 and/or are negative or low for granzyme B. In some embodiments, central memory T cells are CD45RO+, CD62L+, and/or CD8+ T cells. In some embodiments, effector $T_E$ are negative for CD62L, CCR7, CD28, and/or CD127, and/or positive for granzyme B and perforin. In some embodiments, naive CD8+ T lymphocytes are characterized by the expression of phenotypic markers of naive T cells including CD62L, CCR7, CD28, CD3, CD127, and/or CD45RA.

In some embodiments, the presence of a particular cell surface marker on the surface of a cell population can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some embodiments, a decrease in expression of one or markers refers to loss of 1 log 10 in the mean fluorescence intensity and/or decrease of percentage of cells that exhibit the marker of at least or at least about 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least or at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, or CD4+ T cells. In some embodiments, central memory CD4+ cells are CD62L+ or CD45RO+. In some embodiments, effector CD4+ cells are CD62L− or CD45RO−.

In some embodiments, populations of CD4+ and CD8+ that are antigen specific can be obtained by stimulating naive or antigen specific T lymphocytes with antigen. For example, antigen-specific T cell lines or clones can be generated to Cytomegalovirus antigens by isolating T cells from infected subjects and stimulating the cells in vitro with the same antigen. Naive T cells may also be used. Any number of antigens from tumor cells may be utilized as targets to elicit T cell responses. In some embodiments, the adoptive cellular immunotherapy compositions are useful in the treatment or amelioration of a disease or disorder including a solid tumor, hematologic malignancy, breast cancer or melanoma.

In some embodiments, isolated T lymphocyte population can be modified with a polynucleotide encoding a CAR provided herein. In some embodiments, the T cells are obtained from the subject to be treated. In other embodiments, the lymphocytes are obtained from allogeneic human donors, preferably healthy human donors.

In some embodiments, a recombinant infectious virus particle containing a polynucleotide encoding a CAR can be used for gene delivery to a T cell. Examples of viral vectors useful with embodiments of the methods and compositions provided herein include viral vectors derived from simian virus 40 (SV40), adenoviruses, adeno-associated virus (AAV), lentiviral vectors, and/or retroviruses. Example techniques to transduce a cell, such as a T cell include calcium phosphate transfection, protoplast fusion, electroporation, and infection with a viral vector, such as a recombinant adenovirus, adeno-associated virus and retrovirus vector. Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

In some embodiments, a vector containing a polynucleotide encoding a CAR can include a positive marker that enables the selection of cells in vitro. Examples genes include hygromycin-B phosphotransferase gene (hph), which confers resistance to hygromycin B, the amino glycoside phosphotransferase gene (neo or aph) from Tn5 which codes for resistance to the antibiotic G418, the dihydrofolate reductase (DHFR) gene, and the adenosine deaminase gene (ADA).

In some embodiments, CD4+ and CD8+ cells each can separately be modified with an expression vector encoding a CAR to form defined populations. In some embodiments, these cells are then further sorted into subpopulations of naive, central memory and effector cells as described above by sorting for cell surface antigens unique to each of those cell populations. In addition, CD4+ or CD8+ cell populations may be selected by their cytokine profile or proliferative activities. For example, CD4+ T lymphocytes that have enhanced production of cytokines such as IL-2, IL-4, IL-10, TNFα, and/or IFNγ as compared to sham transduced cells or transduced CD8+ cells when stimulated with antigen can be selected. In some embodiments, naive or central memory CD4+ T cells that have enhanced production of IL-2 and/or TNFα are selected. Likewise, CD8+ cells that have enhanced IFNγ production are selected as compared to sham transduced CD8+ cells.

In some embodiments, CD4+ and CD8+ cells that proliferate in response to antigen or tumor targets are selected. For example, CD4+ cells that proliferate vigorously when stimulated with antigen or tumor targets as compared to sham transduced cells, or CD8+ transduced cells are selected. In some embodiments, CD4+ and/or CD8+ cells are selected that are cytotoxic for antigen bearing cells. In embodiments, CD4+ are expected to be weakly cytotoxic as compared to CD8+ cells. In some embodiments, transduced chimeric receptor expressing T cells are selected that can persist in vivo using an animal model established for the particular type of cancer. In embodiments, transduced chimeric receptor CD8+ central memory cells with a short spacer region have been shown to persist in vivo after introduction into the animal for about 3 days or more, 10 days or more, 20 days or more, 30 days or more, 40 days or more, or 50 days or more.

In some embodiments, CD4+ and CD8+ cells can be further separated into subpopulations, such as naive, central memory, and effector memory cell populations. In some embodiments, naive CD4+ cells are CD45RO−, CD45RA+, CD62L+, and/or CD4+ positive T cells. In some embodiments, central memory CD4+ cells are CD62L positive and/or CD45RO positive. In some embodiments, effector CD4+ cells are CD62L negative and/or CD45RO positive. Each of these populations may be independently modified with a CAR, as set forth herein.

In some embodiments, memory T cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory T cells (TCM) include CD62L, CCR7, CD28, CD3, and/or CD127 and are negative or low for granzyme B. In some embodiments, central memory T cells are CD45RO+, CD62L+, and/or CD8+ T cells. In some embodiments, effector T cells ($T_E$) are negative for CD62L, CCR7, CD28, and/or CD127, and positive for granzyme B and/or perforin. In some embodiments, naive CD8+ T lymphocytes are characterized by CD8+, CD62L+, CD45RO+, CCR7+, CD28+CD127+, and/or CD45RO+. Each of these populations may be independently modified with a CAR.

In some embodiments, after transduction and/or selection for CAR bearing cells, the cell populations can be expanded in vitro until a sufficient number of cells are obtained to provide for at least one infusion into a human subject, typically around $10^4$ cells/kg to $10^9$ cells/kg. In some embodiments, the transduced cells can be cultured in the presence of antigen bearing cells, anti CD3, anti CD28, IL 2, IL-7, IL 15, and/or IL-21 and combinations thereof. In some embodiments, subpopulations of CD4+ and CD8+ cells can be combined with one another. In some embodiments, modified naive or central memory CD4+ cells can be combined with modified central memory CD8+ T cells to provide a synergistic cytotoxic effect on antigen bearing cells, such as tumor cells.

Methods of Treatment or Amelioration of a Disease

Some embodiments of the methods and compositions provided herein include treating or ameliorating a cancer in a subject having a tumor comprising a B7H3+ cell by performing immunotherapy. Some such embodiments can include administering an effective amount of a cell, such as a T cell, expressing a CAR, which targets a B7H3 antigen to a subject in need thereof. An effective amount of a cell can refer to an effective number of cells in a certain cell population.

As used herein, "subject" can include a human or a non-human mammal, e.g., a dog, a cat, a mouse, a rat, a cow, a sheep, a pig, a goat, a non-human primate or a bird, e.g., a chicken, as well as any other vertebrate or invertebrate. As used herein, "treat," "treatment," or "treating," can include administering a pharmaceutical composition to a subject for therapeutic purposes, and can include reducing the symptoms or consequences of a disorder, such as preventing the occurrence of metastases from a primary tumor, reducing the number of tumor cells of a metastatic tumor or inhibiting the growth of tumor cells of a metastatic tumor; and can include curing a disorder, such as eliminating the symptoms of a disorder, such as the elimination of tumor cells of a metastatic tumor in a subject. As used herein, "ameliorate", or "ameliorating" can include a therapeutic effect which relieves, to some extent, one or more of the symptoms of a disorder. As used herein, "prevent," "preventing" and "prevention" can include inhibiting the occurrence of a disorder, such as inhibiting the metastasis of a primary tumor, and can include preventing a primary an action that occurs before a subject begins to suffer from the regrowth of the cancer and/or which inhibits or reduces the severity of the cancer. As used herein, an "effective amount" can include an amount, such as a dose, of a therapeutic compound sufficient to treat a disorder.

In some embodiments, a tumor comprising a B7H3+ cell includes a cancer such as melanoma, leukemia, breast, prostate, ovarian, pancreatic, colorectal, endometrial, oral squamous cell carcinoma, cervical, non-small lung, bladder, clear cell renal cell carcinoma, and/or glioma. In some embodiments, the tumor comprises a glioma, such as oligodendroglioma, anaplastic astrocytoma, glioblastoma multiforme (GBM), ependymoma, and/or intrinsic pontine glioma (DIPG). In some embodiments, the tumor comprises GBM. See e.g., Zhou Z., et al., (2013), J Neurooncol. 111:257-64, which is incorporated by reference in its entirety.

In some embodiments, a CAR-modified T cell provided herein can persist in vivo for at least 3 days, or at least 10 days. In some embodiments, a CAR-modified T cells provided herein can proliferate in vivo through at least 2, or at least 3 generations as determined by CFSE dye dilution. Proliferation and persistence of the CAR-modified T cells can be determined by using an animal model of the disease or disorder and administering the cells and determining persistence and/or proliferative capacity of the transferred cells. In other embodiments, proliferation and activation can be tested in vitro by going through multiple cycles of activation with antigen bearing cells.

In some embodiments, the presence of CAR-modified cells in a subject can be determined by obtaining a sample from the subject, and detecting the presence of an identifier marker, such as an EGFRt identifier marker in the sample.

In some embodiments, performing cellular immunotherapy can include administering to the subject a genetically modified helper T lymphocyte cell preparation, wherein the modified helper T lymphocyte cell preparation comprises CD4+ T cells that have a CAR, such as a CAR, which specifically binds to B7H3. In some embodiments, performing cellular immunotherapy can include administering to the subject a genetically modified cytotoxic T lymphocyte cell preparation, wherein the modified cytotoxic T lymphocyte cell preparation comprises CD8+ cells that have a CAR, such as a CAR, which specifically binds to B7H3. In some embodiments, the CD4+ T helper lymphocyte cell is selected prior to introduction of the CAR from naive CD4+ T cells, central memory CD4+ T cells, effector memory CD4+ T cells or bulk CD4+ T cells. In some embodiments, CD4+ helper lymphocyte cell is a naive CD4+ T cell, wherein the naive CD4+ T cell comprises a CD45RO−, CD45RA+, and/or CD62L+ CD4+ T cell. In some embodiments, the CD8+ T cytotoxic lymphocyte cell is selected prior to introduction of the CAR from naive CD8+ T cells, central memory CD8+ T cells, effector memory CD8+ T cells or bulk CD8+ T cells. In some embodiments, the CD8+ cytotoxic T lymphocyte cell is a central memory T cell wherein the central memory T cell comprises a CD45RO+, CD62L+, and/or CD8+ T cell. In some embodiments, the CD8+ cytotoxic T lymphocyte cell is a central memory T cell and the CD4+ helper T lymphocyte cell is a naive CD4+ T cell.

Cells prepared as described herein can be utilized in methods and compositions for adoptive immunotherapy in accordance with known techniques, or variations thereof that will be apparent to those skilled in the art.

In some embodiments, the cells are formulated by first harvesting them from their culture medium, and then washing and concentrating the cells in a medium and container system suitable for administration, such as a pharmaceutically acceptable carrier, in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

In some embodiments, a therapeutically effective amount of cells in the composition is at least 2 cell subsets, such as, 1 CD8+ central memory T cell subset and 1 CD4+ helper T cell subset. In some embodiments, a therapeutically effective amount of cells in the composition is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen, such as B7H3, are desired, then the population will contain greater than 70%, generally greater than 80%, 85% and/or 90-95% of such cells. For uses provided herein, the cells are generally in a volume of a liter or less (but not zero), can be 500 ml or less (but not zero), even 250 ml or 100 ml or less (but not zero). Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^9$, $10^{10}$, $10^{11}$ or $10^{12}$ cells.

In some embodiments, a pharmaceutical composition comprising a cell provided herein comprising a CAR can be administered intravenously, intraperitoneally, intratumorly, into the bone marrow, into the lymph node, and/or into cerebrospinal fluid. In some embodiments, a cell provided herein comprising a CAR can be delivered to the site of the tumor. In some embodiments, a pharmaceutical composition comprising a cell provided herein comprising a CAR can be combined with a compound that targets the cells to the tumor or the immune system compartments and avoid sites such as the lung.

Combination Therapies

Some embodiments of the methods and compositions provided herein include treating or ameliorating a disease or disorder in a subject, such as a cancer having a B7H3+ cell, by immunotherapy in combination with an additional therapeutic regimen. As used herein, administering in combination can include administering two or more agents to a subject, such as immunotherapy and an additional therapeutic regimen, such that the two or more agents may be found in the subject's bloodstream at the same time, regardless of when or how they are actually administered. For example, a subject can be administered a first agent, such as a cell expressing a CAR, and can be administered an additional therapeutic agent. In some embodiments, the agents are administered simultaneously. In some such embodiments, administration in combination is accomplished by combining the agents in a single dosage form. When combining the agents in a single dosage form, they may be physically mixed. In some embodiments, the agents are administered sequentially. In some embodiments, the agents are administered through the same route, such as intravenously. In some embodiments, the agents are administered through different routes, such as one being administered orally and another being administered intravenously.

In some embodiments, an additional therapeutic regimen can include radiation therapy. In some embodiments, an additional therapeutic regimen can include administering a chemotherapeutic agent. In some embodiments, the chemotherapeutic agent is a cell cycle inhibitor. As used herein, "cell cycle inhibitor" can include a chemotherapeutic agent that inhibits or prevents the division and/or replication of cells. In some embodiments, a cell cycle inhibitor can include a chemotherapeutic agent such as Doxorubicin, Melphlan, Roscovitine, Mitomycin C, Hydroxyurea, 5-Fluorouracil, Cisplatin, Ara-C, Etoposide, Gemcitabine, Bortezomib, Sunitinib, Sorafenib, Sodium Valproate, a HDAC Inhibitor, or Dacarbazine. More examples of additional chemotherapeutic agents include HDAC inhibitors such as FR01228, Trichostatin A, SAHA and/or PDX101. In some embodiments, the cell cycle inhibitor is a DNA synthesis inhibitor. As used herein, "DNA synthesis inhibitor" can include a chemotherapeutic agent that inhibits or prevents the synthesis of DNA by a cancer cell. Examples of DNA synthesis inhibitors include AraC (cytarabine), 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine or forodesine. More examples of additional chemotherapeutic agents include FLT3 inhibitors such as Semexanib (SU5416), Sunitinib (SU11248), Midostaurin (PKC412), Lestautinib (CEP-701), Tandutinib (MLN518), CHIR-258, Sorafenib (BAY-43-9006) and/or KW-2449. More examples of additional chemotherapeutic agents include farnesyltransferase inhibitors such as tipifarnib (R115777, Zarnestra), lonafarnib (SCH66336, Sarasar™) and/or BMS-214662. More examples of additional chemotherapeutic agents include topoisomerase II inhibitors such as the epipodophyllotoxins etoposide, teniposide, anthracyclines doxorubicin and/or 4-epi-doxorubicin. More examples of additional chemotherapeutic agents include P-glycoprotein modulators such as zosuquidar trihydrochloride (Z.3HCL), vanadate, or verapamil. More examples of additional chemotherapeutic agents include hypomethylating agents such as 5-aza-cytidine or 2' deoxyazacitidine.

Kits

Some embodiments of the methods and compositions provided herein include kits. In some such embodiments, a kit can include reagents to modify a cell to express a CAR. Some such embodiments can include an isolated polynucleotide provided herein which encodes a CAR having an antigen binding domain which specifically binds to B7H3. In some embodiments, a kit can also include reagents to transduce a cell with an isolated polynucleotide provided herein, which encodes a CAR having an antigen binding domain which specifically binds to B7H3.

EXAMPLES

Example 1—In Vitro and In Vivo Activities of B7H3 CAR T Cells

Viral vectors containing polynucleotides encoding CARs, which target human B7H3 were constructed with various spacer domains (FIG. 1A). Each polynucleotide encoded an antigen binding domain comprising a scFv that specifically binds human B7H3, one of three spacer domains, a signaling domain comprising CD28tm, 41BB, CD3-zeta, a T2A skip sequence, and an identifier marker comprising truncated EGFR (EGFRt). The scFv included nucleotide sequences encoding a $V_H$ region of SEQ ID NO:14, and encoding a $V_L$ region of SEQ ID NO: 16. The EGFRt provided a selection and an in vivo tracking marker for CAR-T-cells. The spacers included a short spacer (S), which included a human IgG4 hinge region; a medium spacer (S), which included a human IgG4 hinge region and CH3 domain; and a long spacer (L), which included a human IgG4 hinge region, CH2 domain and CH3 domain. In this example, the long spacer included a wild-type nucleotide sequence. Thus, the polynucleotides encoded B7H3 CARs with S, M and L (wild type) spacer regions.

CD8+ T cells were transduced with the polynucleotides encoding the B7H3-CARs to generate B7H3 CAR T cells having CARs with either the short (S), medium (M), or long (L) spacer regions, with a method was substantially similar to that described in Hudecek M, et al., (2013) Clin Cancer Res. 19:3153-64, which is incorporated by reference in its entirety.

Figure 1B:
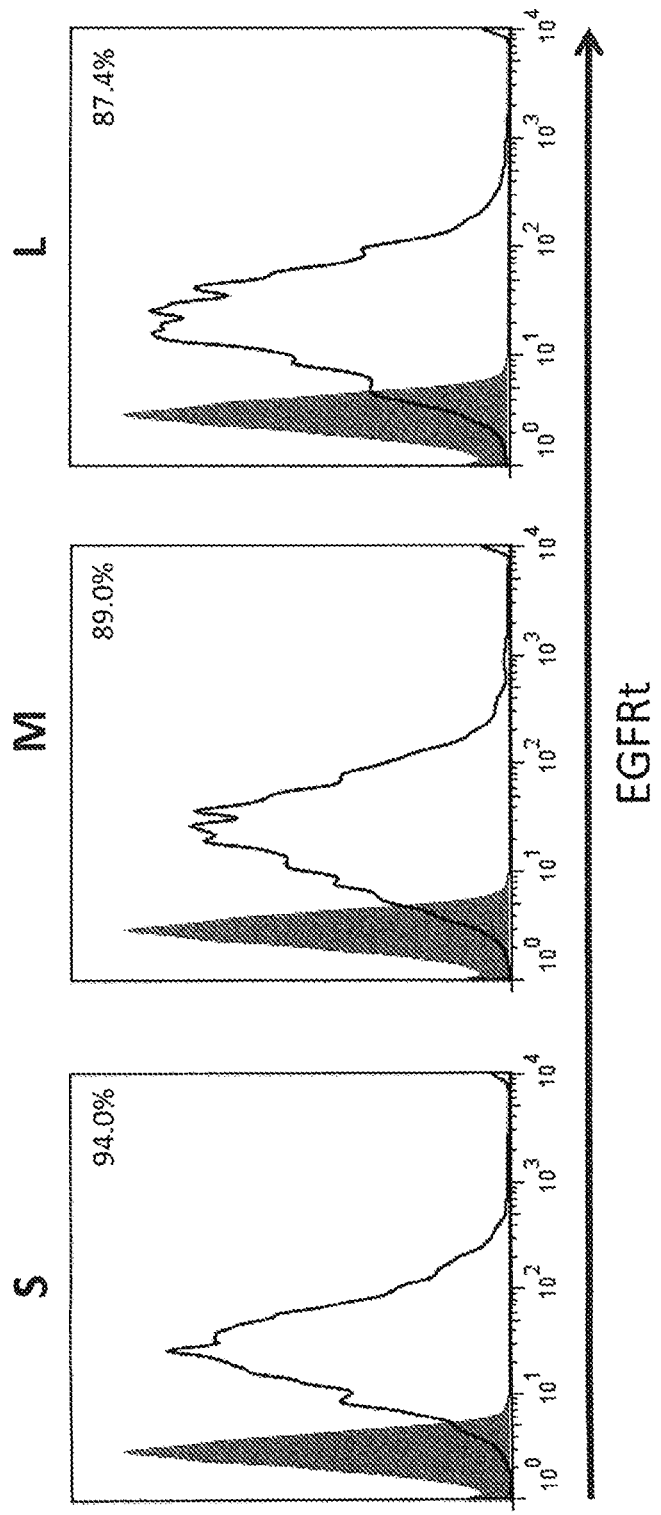
FIG. 1B are graphs showing identification by EGFRt of B7H3 CAR T cells containing CARs having either a short (S), medium (M), or long (L) spacer region.
Figure 1C:
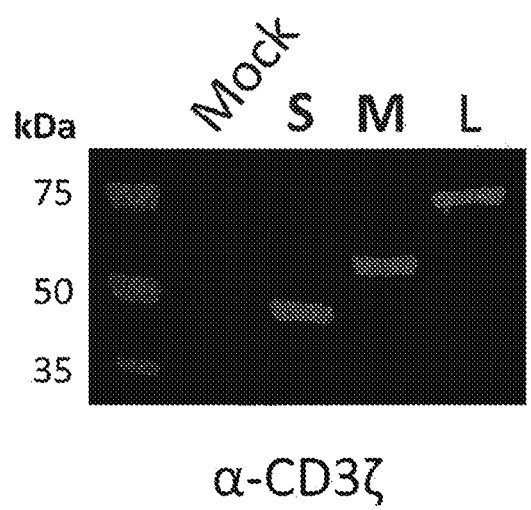
FIG. 1C is a photograph of a Western blot showing CD3-zeta expression in T cells transduced with polynucleotides encoding B7H3 CARs having either a short (S), medium (M), or long (L) spacer region.

Cytotoxicity, cytokine release, and proliferation assays were performed with the CAR T cells with a method substantially similar to that described in Hudecek M, et al., (2013). FIG. 1B shows identification by EGFRt of the B7H3 CAR T cells having CARs with either the short (S), medium (M), or long (L) spacer regions. FIG. 1C is a Western blot showing expression of CD3-zeta in the B7H3 CAR T cells.

Figure 1D:
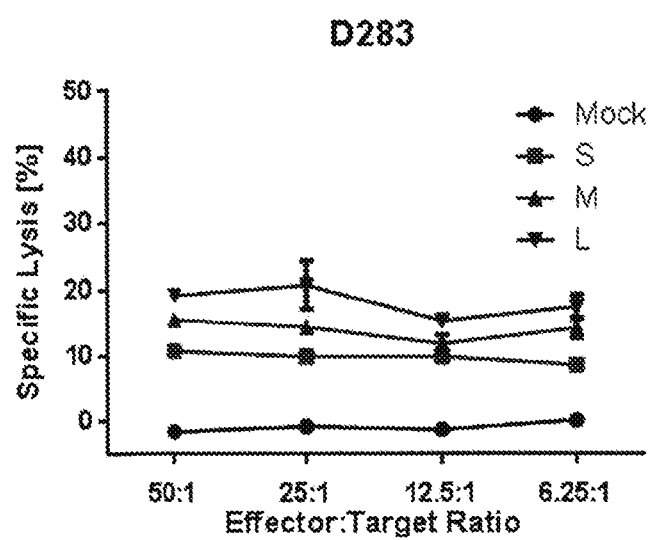
FIG. 1D is a series of graphs showing in vitro percentage specific lysis and levels of cytokine release for B7H3 CAR T cells containing CARs having either a short (S), medium (M), or long (L) spacer region, and stimulated with Epd-110GH cells, PNET-109FH cells line, D283 cell line, or Med411FH cell line. Measured cytokines include IFNγ, IL-2, and B7H3TNF.
Figure 1D:
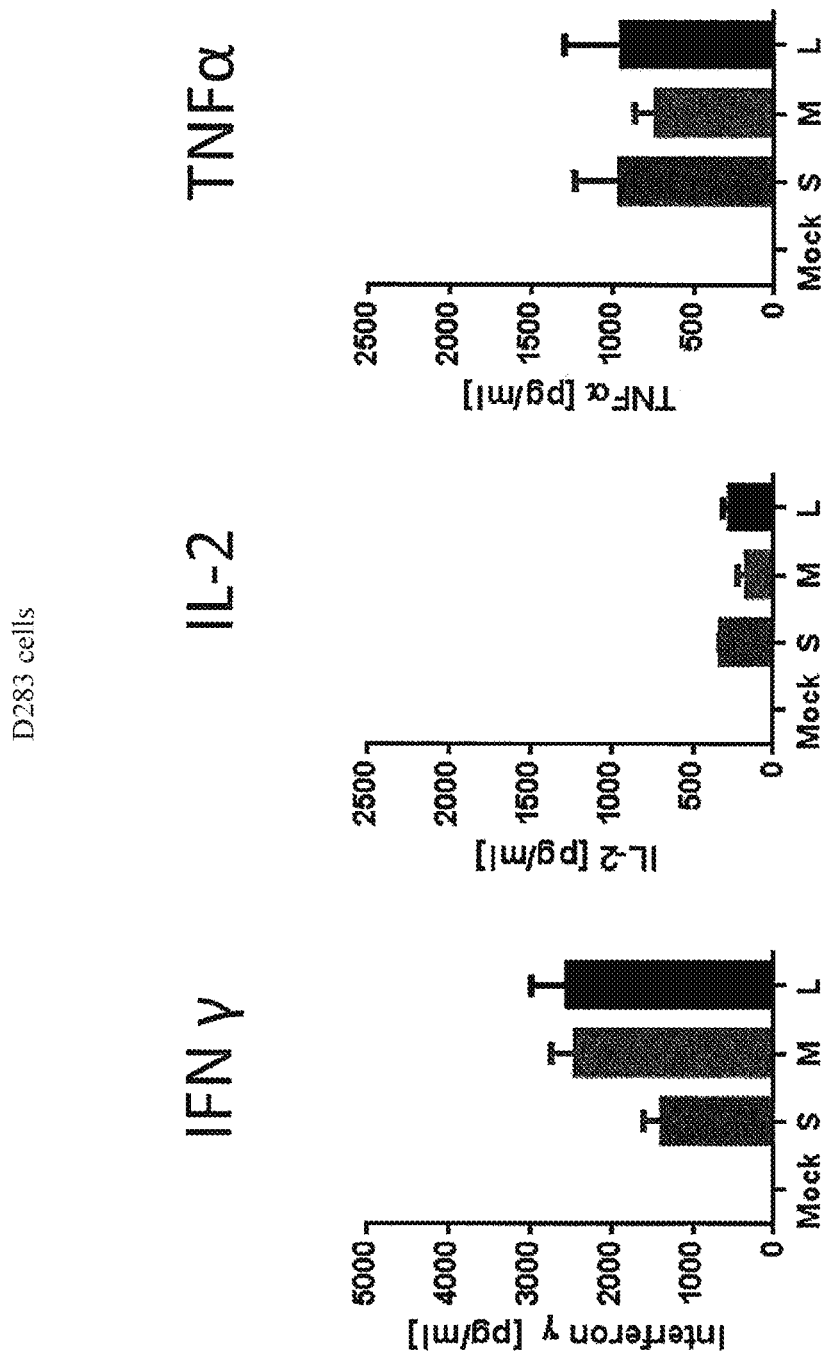
Figure 1D:
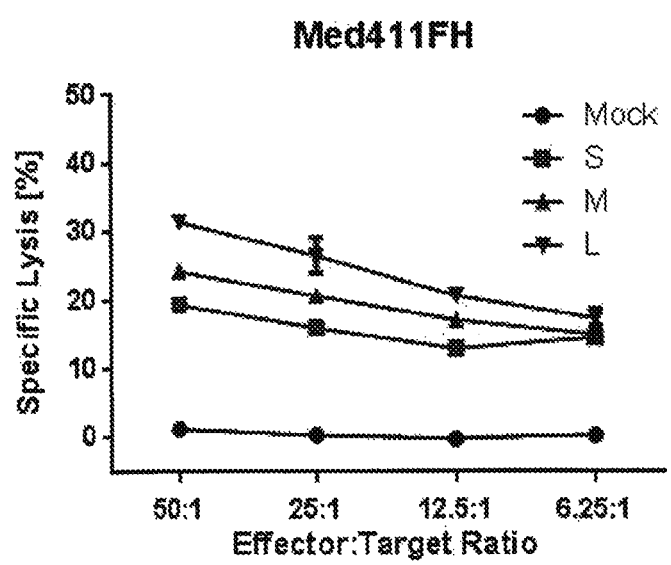
Figure 1D:
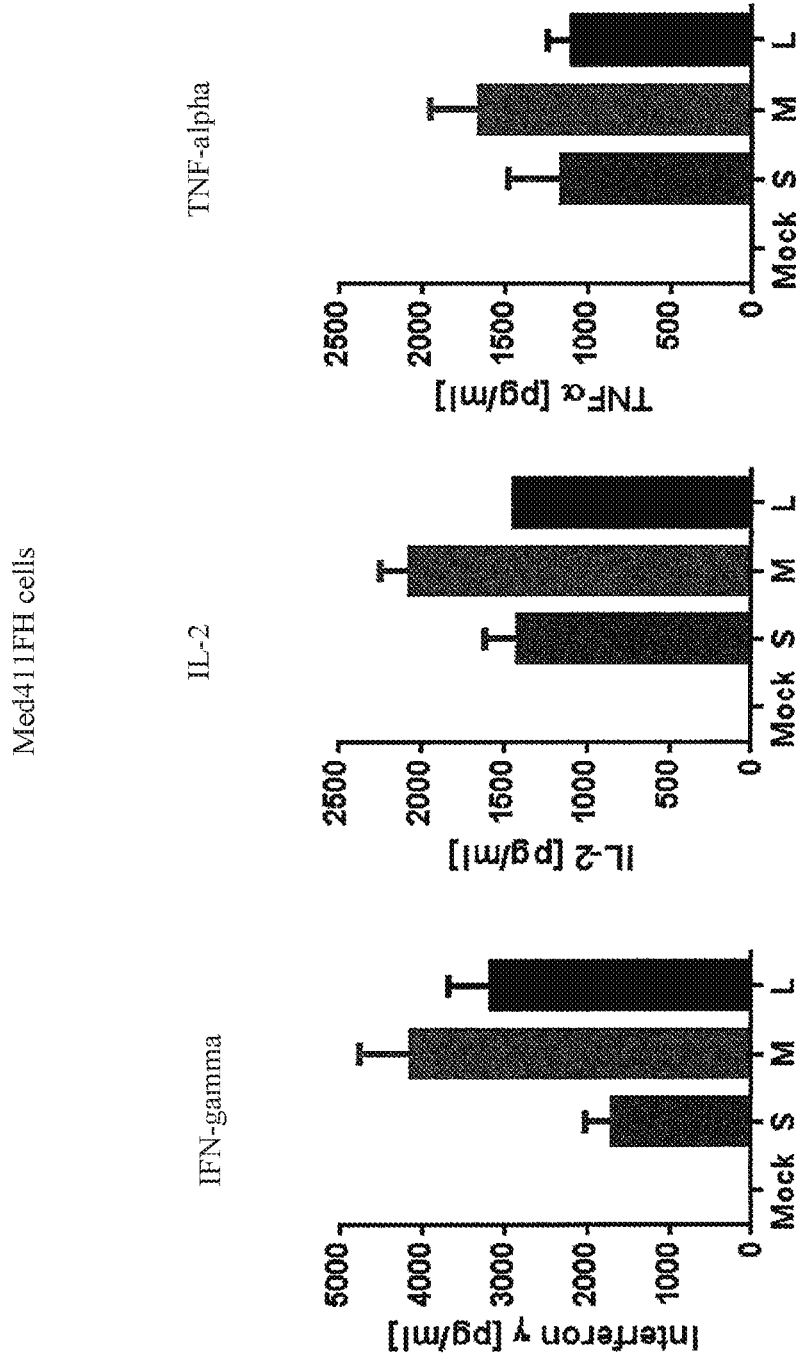
Figure 1D:
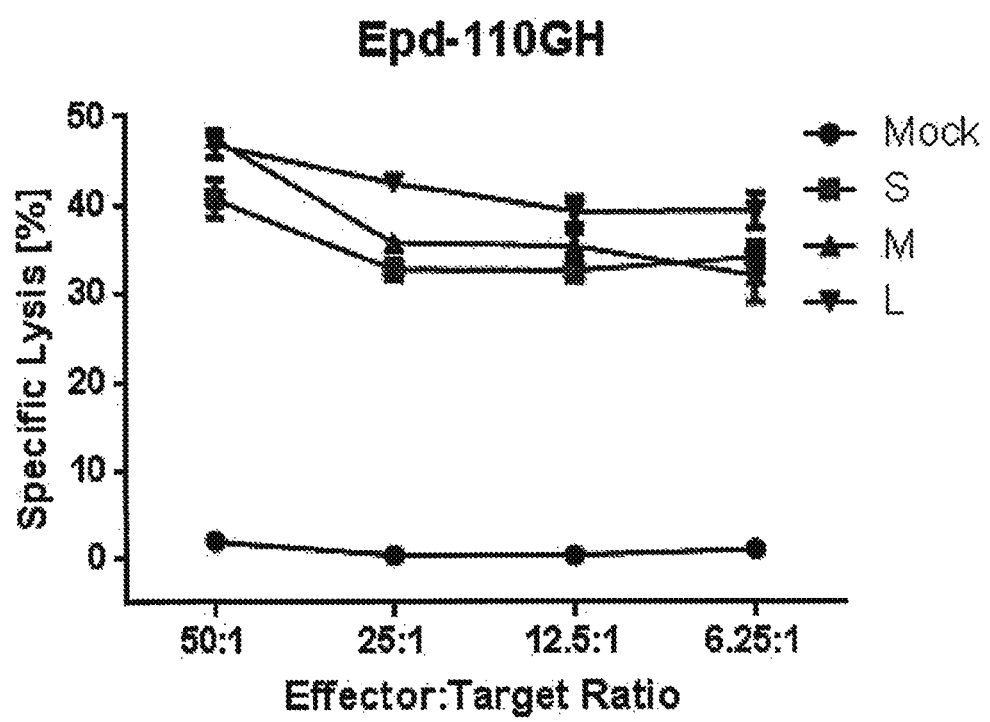
Figure 1D:
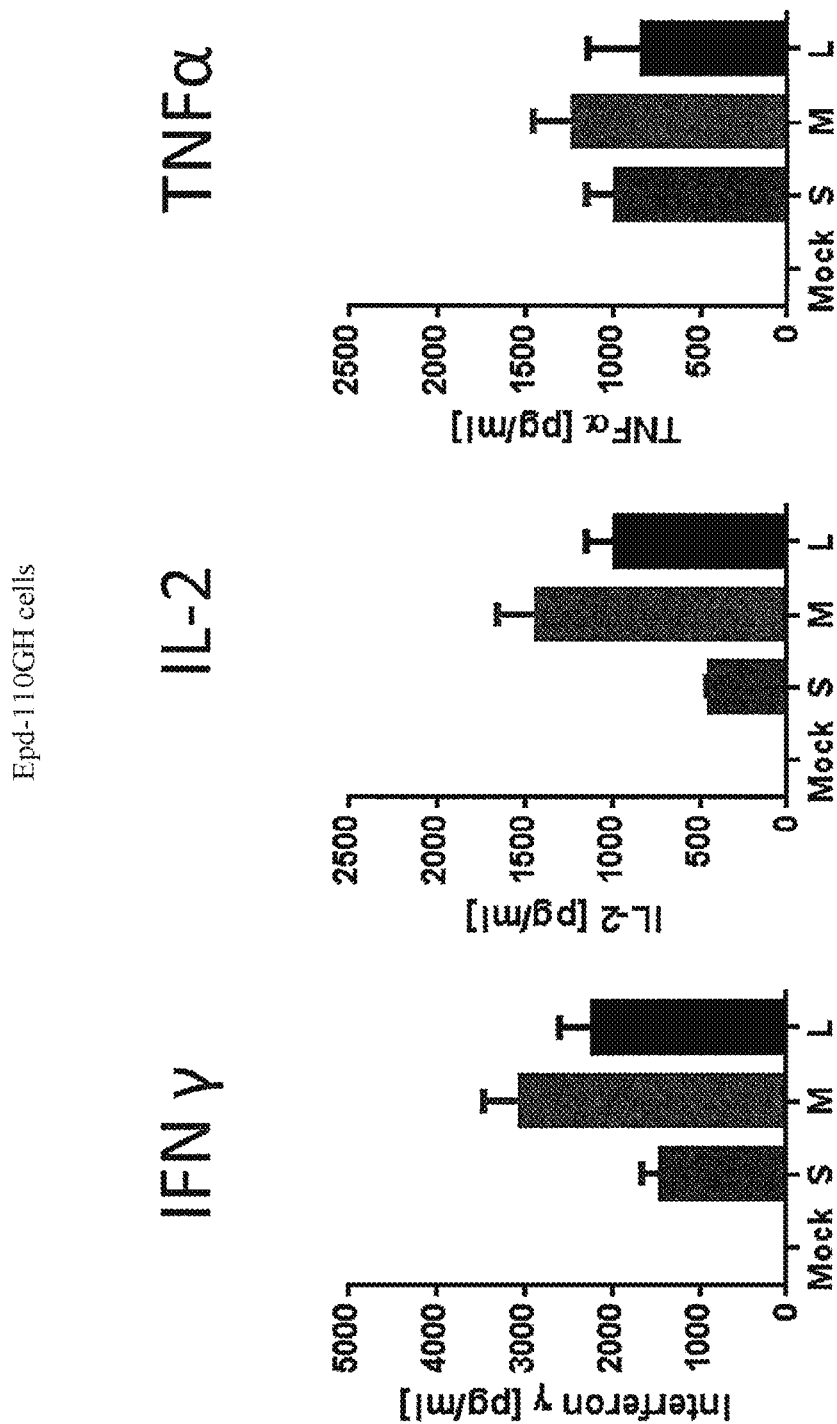
Figure 1D:
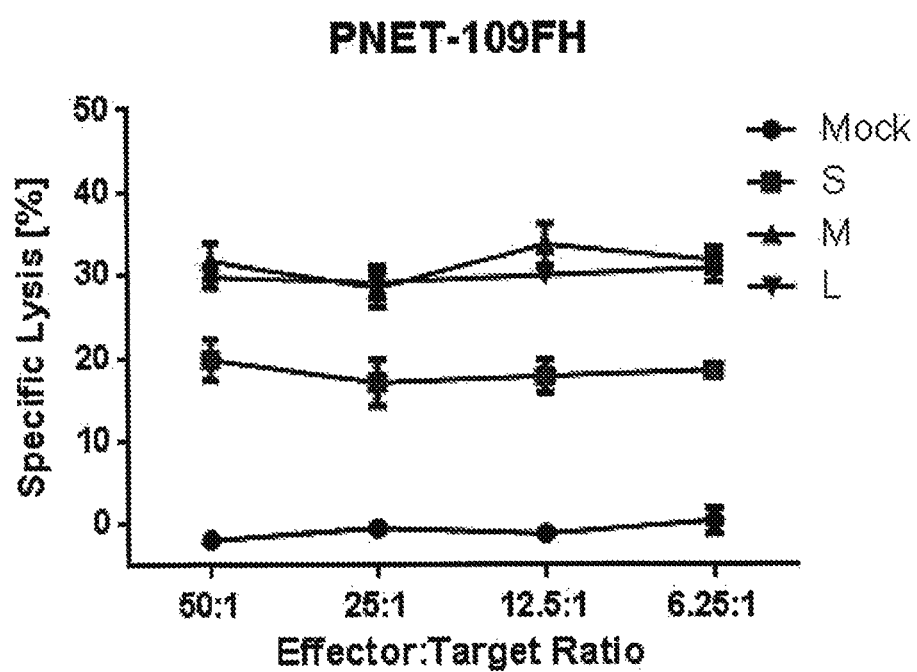
Figure 1D:
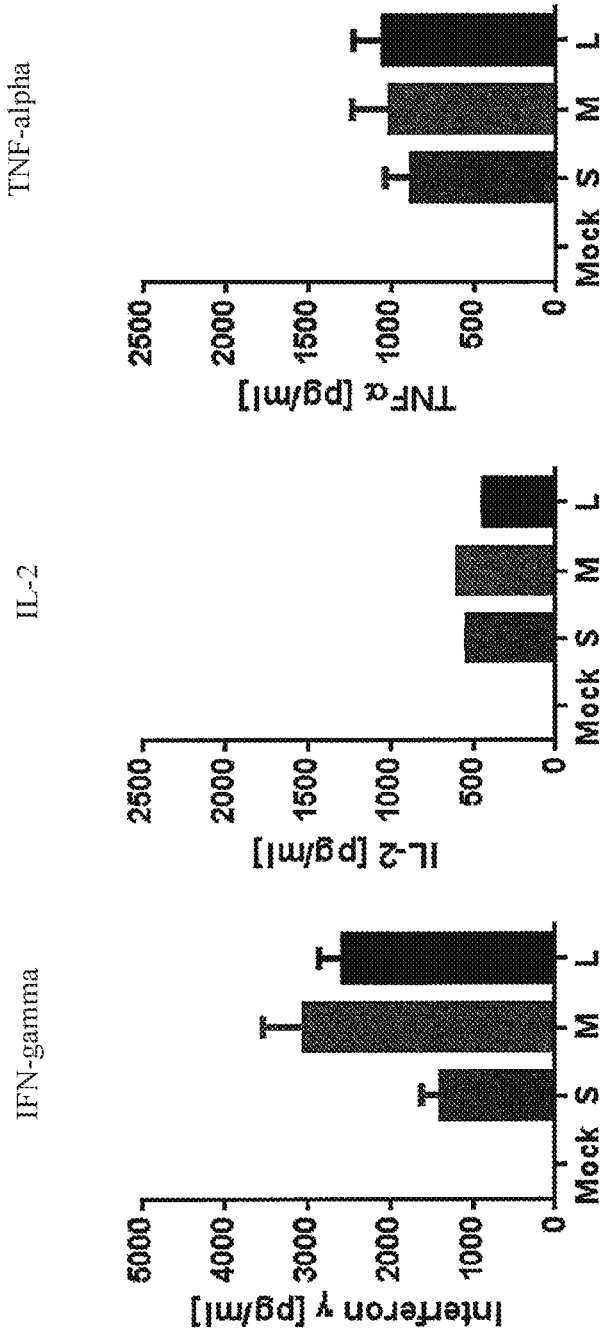

Cytolysis assays were performed with B7H3 CAR T cells and various B7H3+ cell lines including: human medulloblastoma cell lines (Med411FH and D283), a primitive neuroectodermal tumor cell line (PNET-109FH), and an ependymoma cell line (Epd-110GH). B7H3 CAR T cells having CARs with either the short (S), medium (M), or long (L) spacer regions each efficiently lysed B7H3+ cells (FIG. 1D). In response to stimulation with the Med411FH, D283, PNET-109FH, and Epd-110GH cells, B7H3 CAR T cells having CARs with either the short (S), medium (M), or long (L) spacer regions produced cytokines including IFNγ, IL-2, and TNFα (FIG. 1D). B7H3 CAR T cells having a CAR with the medium (M) spacer region demonstrated a substantial trend of higher levels of cytokines in with the Med411FH, PNET-109FH, and Epd-110GH cells, compared to B7H3 CAR T cells having CARs with either the short (S) or (L) spacer regions.

Figure 1E:
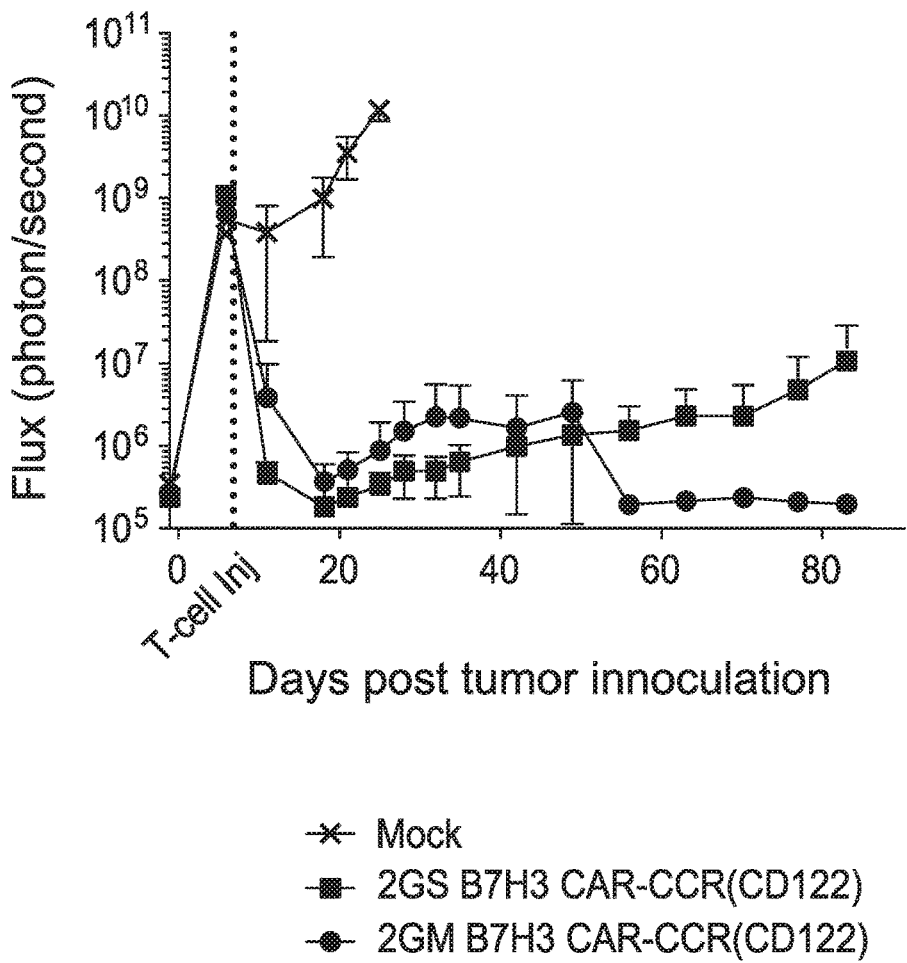
FIG. 1E is a series of graphs showing levels of B7H3+ U87 tumor cells detected using a firefly luciferase (ffluc) marker and survival rate by Kaplan Meier curve, in mice inoculated with U87 cells, and treated with B7H3 CAR T cells containing CARs having either a short (S), or medium (M) spacer region. (X) mock; (■) B7H3 CAR with shorter spacer region; (●) B7H3 CAR with medium spacer region.
Figure 1E:
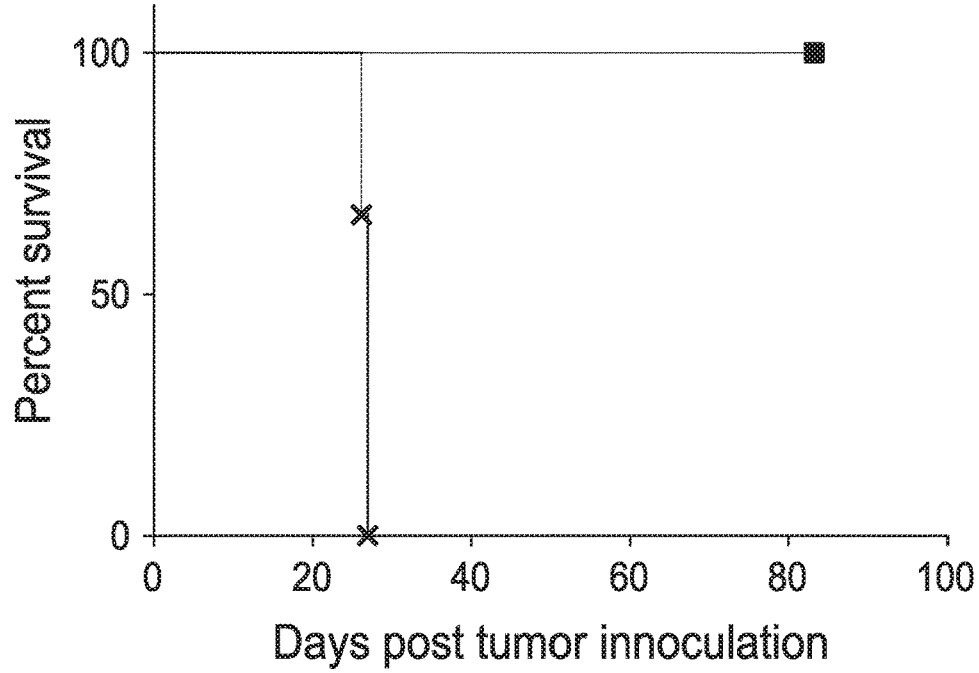
Figure 1E:
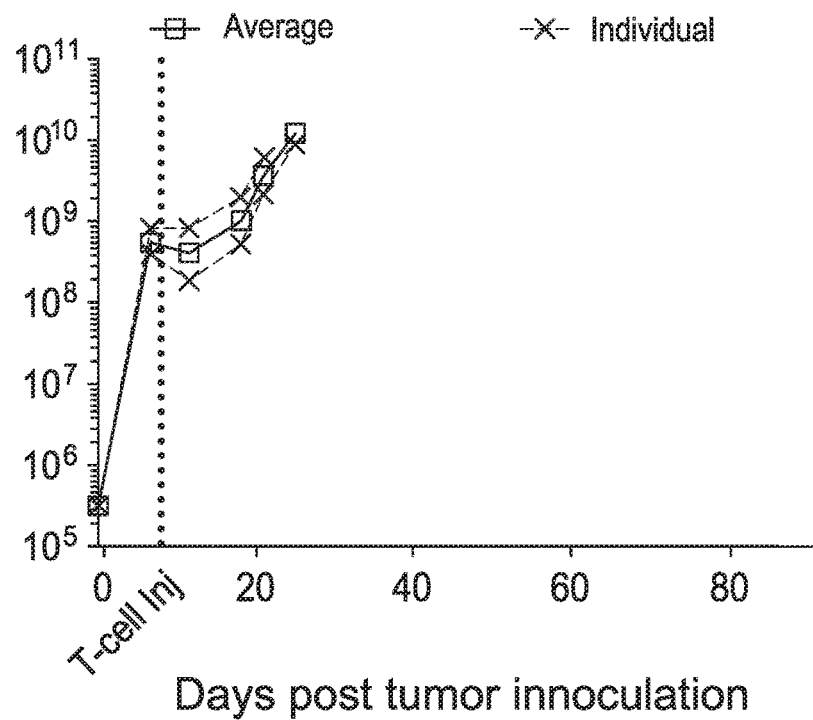
Figure 1E:
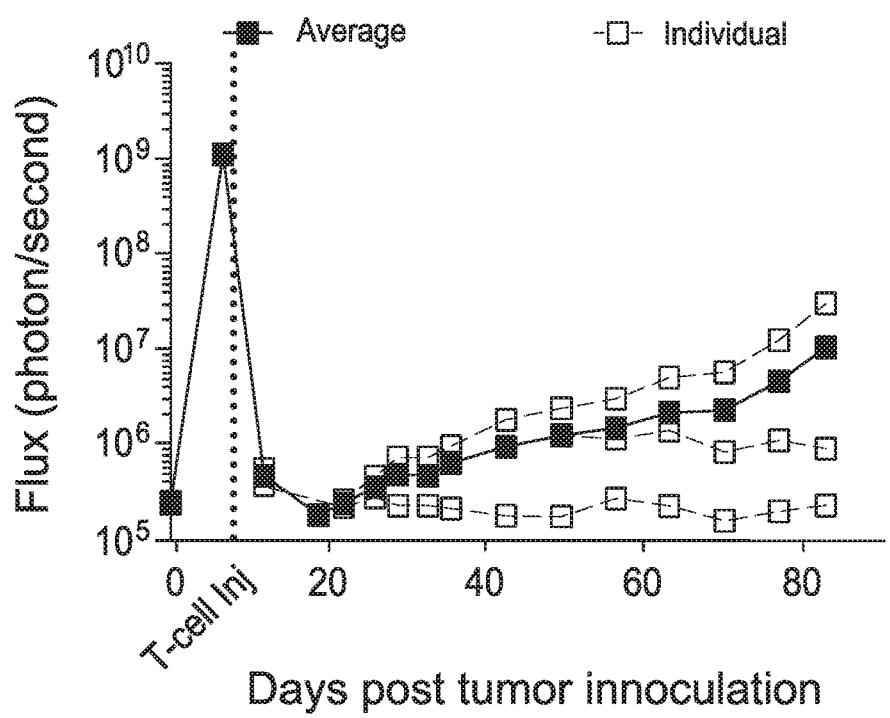
Figure 1E:
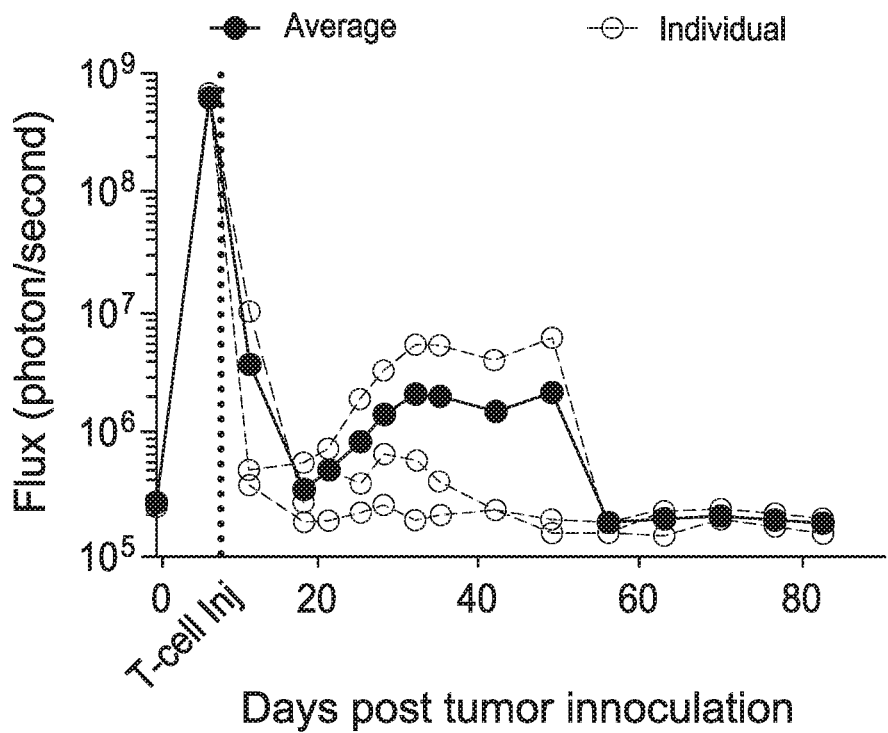

NOD-SCID mice were engrafted i.v. with 2×10$^6$ B7H3+ U87 tumor cells expressing an eGFP marker. The marker is a fusion of GFP with ffluc; the ffluc component is useful for in vivo imaging. B7H3 CAR T cells having CARs with either the short (S), or medium (M) spacer regions were injected via tail vein into tumor-free mice or mice engrafted with the U87 cells. Bioluminescence imaging was performed as described in Hudecek M, et al., (2013). B7H3 CAR T cells having a CAR with the long (L) spacer region were not used in this experiment because residual monocyte activity in NOD-SCID mice inhibited activity of CARs containing the wild-type long spacer. FIG. 1E shows that mice treated with B7H3 CAR T cells having CARs with either the short (S), or medium (M) spacer regions had a significant decrease in the number of U87 tumor cells and a significantly increased survival rate, compared to control mice.

Example 2—In Vitro and In Vivo Activities of B7H3 CAR T Cells

Figure 2A:
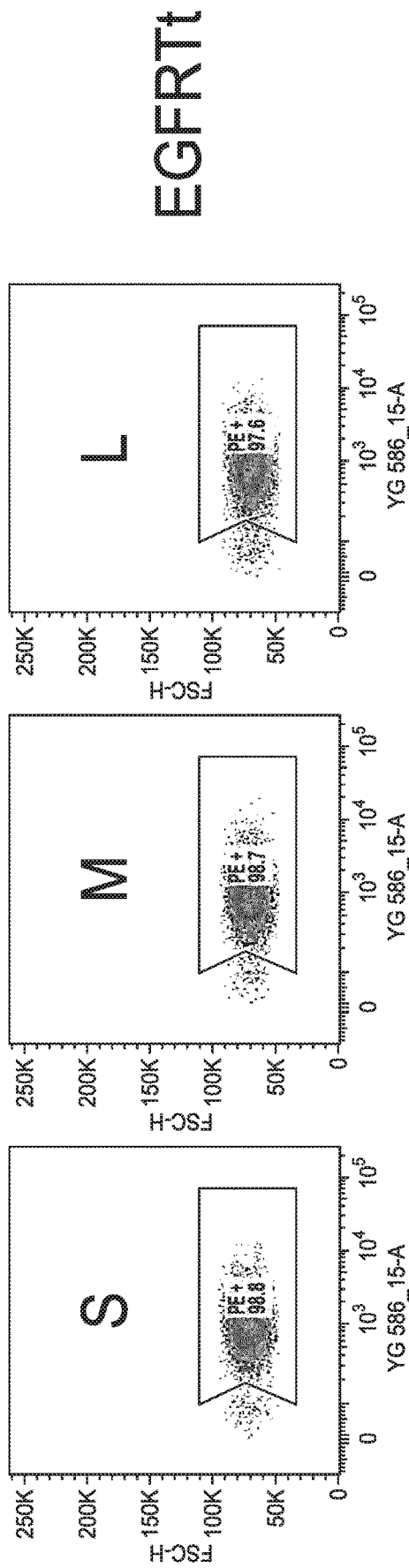
FIG. 2A is a series of graphs showing expression of EGFRt, immunoglobulin which binds Protein-L, and Fc which binds anti-Fc in CD4+ B7H3 CAR T cells containing CARs having either a short (S), medium (M), or long (L) spacer region.
Figure 2A:
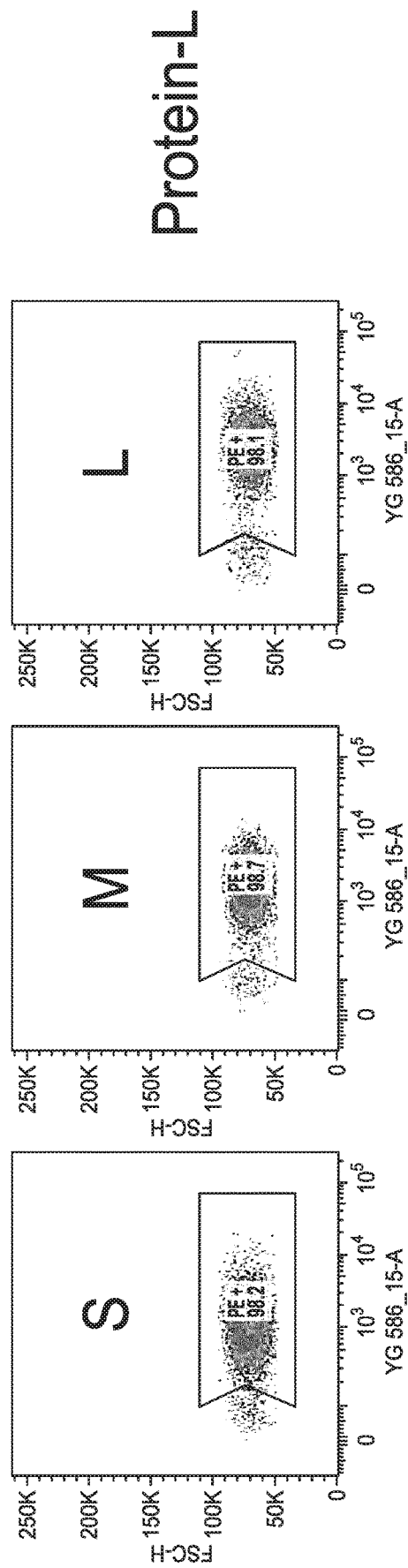
Figure 2A:
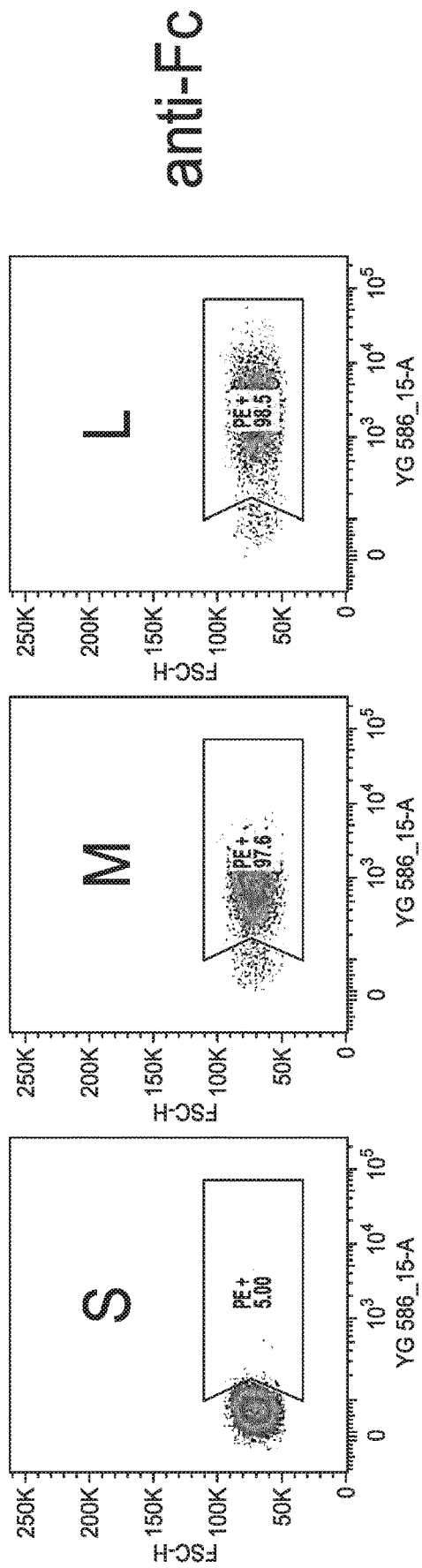
Figure 2B:
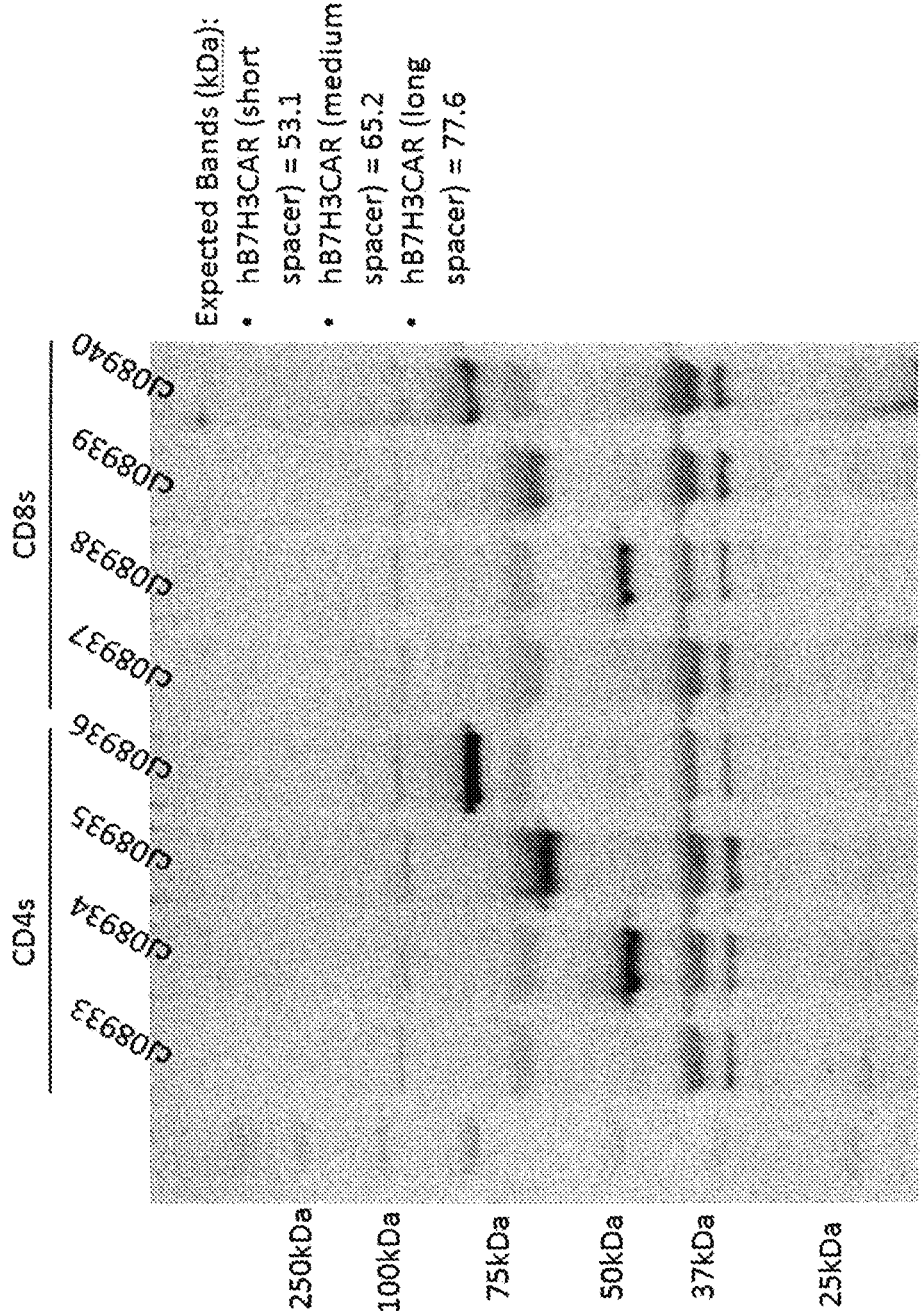
FIG. 2B is a photograph of a Western blot showing CD3-zeta expression in various clones of CD4+ or CD8+ cells transduced with polynucleotides encoding B7H3 CARs having either a short (S), medium (M), or long (L) spacer region.

CD4+ T cells and CD8+ T cells were transduced with polynucleotides encoding the B7H3-CARs having a short spacer region (S), a medium spacer region (M), and a long spacer region (L). In this example, the long spacer region contained a double mutant (L235D, N297Q). Expression of various proteins were measured including: EGFRt; immunoglobulin which is a binding partner for protein L; and human Fc which is a binding partner for anti-Fc (FIG. 2A). EGFRt and immunoglobulin were detected in B7H3 CAR T cells which contained CARS having the long spacer region, the medium spacer region, or the short spacer region. The level of detected human Fc was lower in B7H3 CAR T cells which contained CARs having the short spacer region, compared to B7H3 CAR T cells which contained CARs having the long or medium spacer region. This was consistent with the short spacer not containing certain Fc components. Expression of CD3-zeta was measured for various populations of transduced CD4+ T cells and CD8+ T cells (FIG. 2B).

Figure 2C:
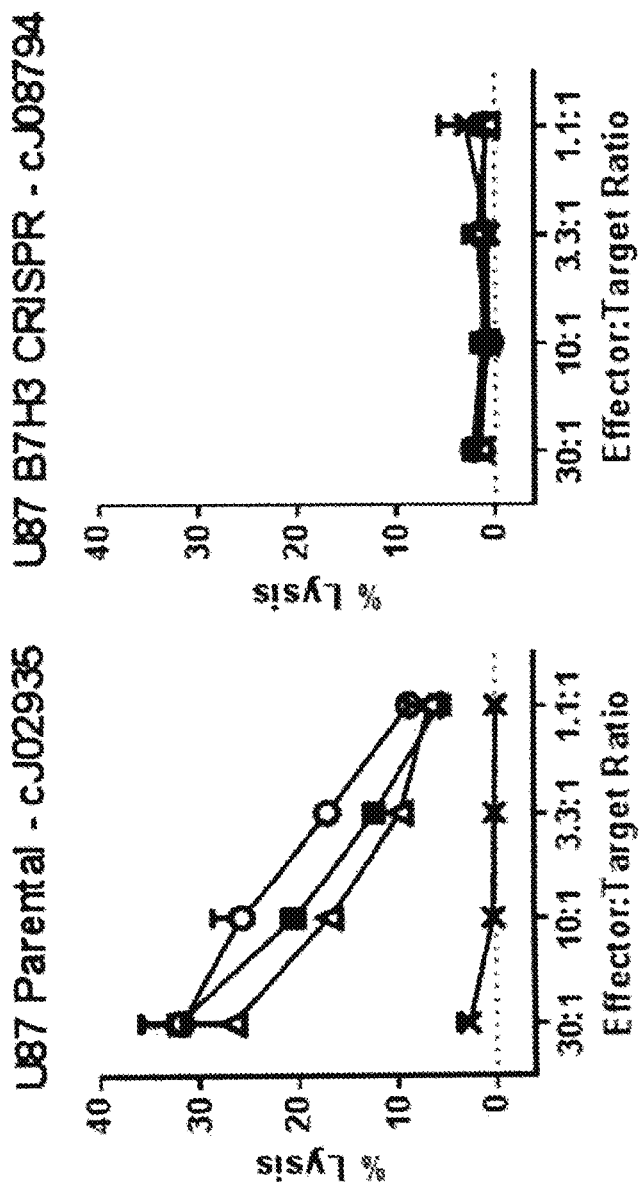
FIG. 2C is a series of graphs showing in vitro percentage specific lysis for B7H3 CAR T cells containing CARs having either a short (S), medium (M), or long (L) spacer region, and stimulated with either U87 cells, modified U87 lacking B7H3 expression, Be2 cells, or D283 cells. (X) mock; (▲) B7H3 CAR with short spacer region; (○) B7H3 CAR with medium spacer region; and (■) B7H3 CAR with long spacer region.
Figure 2C:
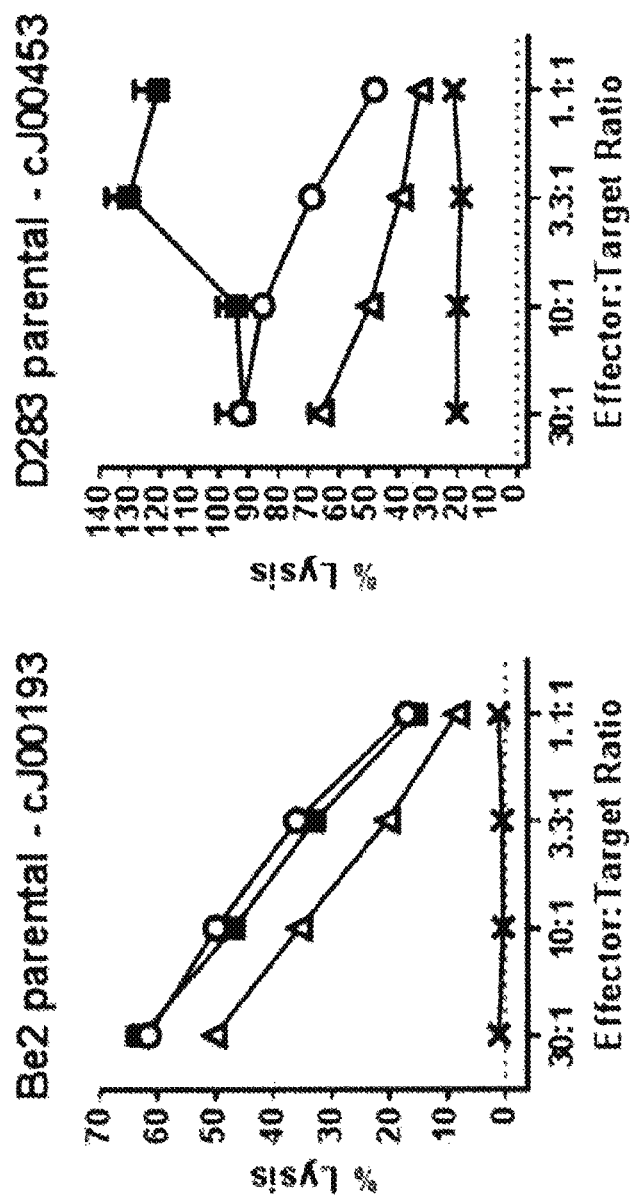
Figure 2D:
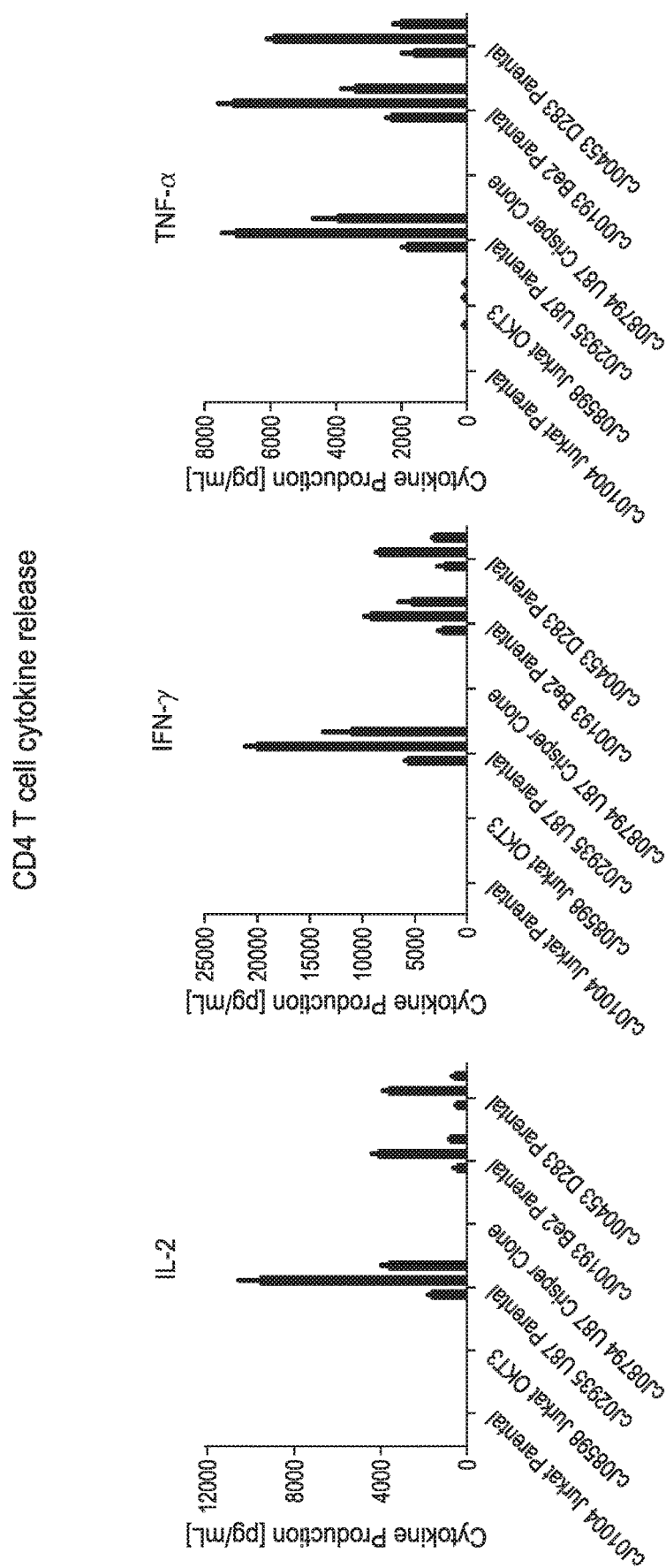
FIG. 2D is a series of graphs showing levels of cytokine release for CD4+ or CD8+ B7H3 CAR T cells containing CARs having either a short (S), medium (M), or long (L) spacer region, and stimulated with Jurkat cells, Jurkat OKT3 cells, U87 cells, modified U87 cells lacking B7H3 expression, Be2 cells, and D283 cells. Measured cytokines include IFNγ, IL-2, and TNF.
Figure 2D:
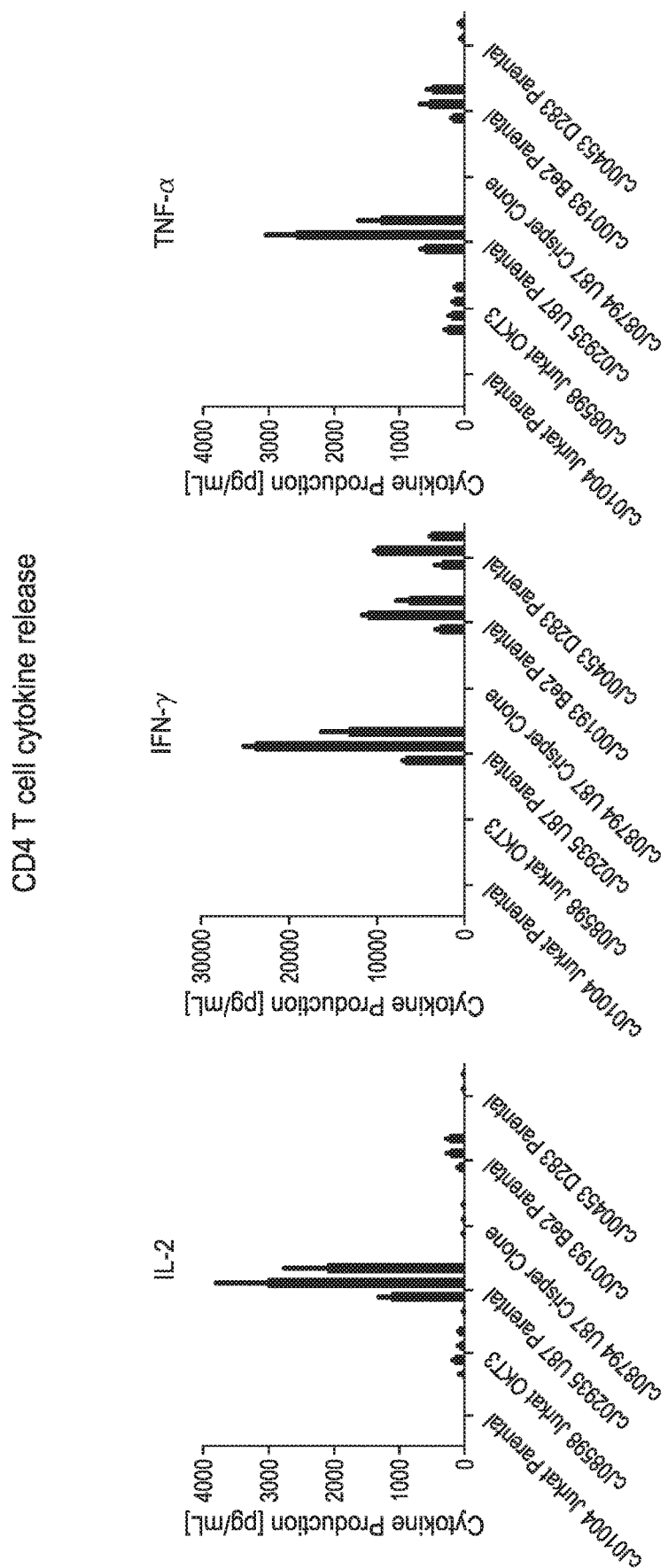

Cytolysis assays were performed with B7H3 CAR T cells and various cell lines including: U87 cells (glioblastoma cell line), modified U87 cells which lacked B7H3 expression, Be2 cells (neuroblastoma cell line), and D283 cells (medulloblastoma cell line). B7H3 CAR T cells having CARS with either the short (S), medium (M), or long (L) spacer regions each efficiently lysed B7H3+ cells (FIG. 2C). B7H3 CAR T cells had no significant cytotoxic effect on modified U87 cells lacking B7H3 expression. B7H3 CAR T cells having CARs with either the short (S), medium (M), or long (L) spacer regions had activity against each of the U87 cells, Be2 cells, and D283 cells.

in vitro cytokine production was measured for B7H3 CAR T cells against various cell lines including Jurkat cells (T cell line), Jurkat OKT3 cells, U87 cells, modified U87 cells lacking B7H3 expression, Be2 cells, and D283 cells. In response to stimulation with U87 cells, Be2 cells, and D283 cells, the CD4+ B7H3 CAR T cells having CARs with either the short (S), medium (M), or long (L) spacer regions each demonstrated substantial cytokine release, compared to CD4+ B7H3 CAR T cells incubated with Jurkat, Jurkat OKT3 cells, or modified U87 cells lacking B7H3 expression (FIG. 2D). Stimulated CD4+ B7H3 CAR T cells and CD8+ B7H3 CAR T cells, each having a CAR with a medium (M) spacer region demonstrated significant and substantial greater levels of cytokine release compared to CD4+ B7H3 CAR T cells and CD8+ B7H3 CAR T cells, each having a CAR with either a short (S) or long (L) spacer region (FIG. 2D).

Figure 2E:
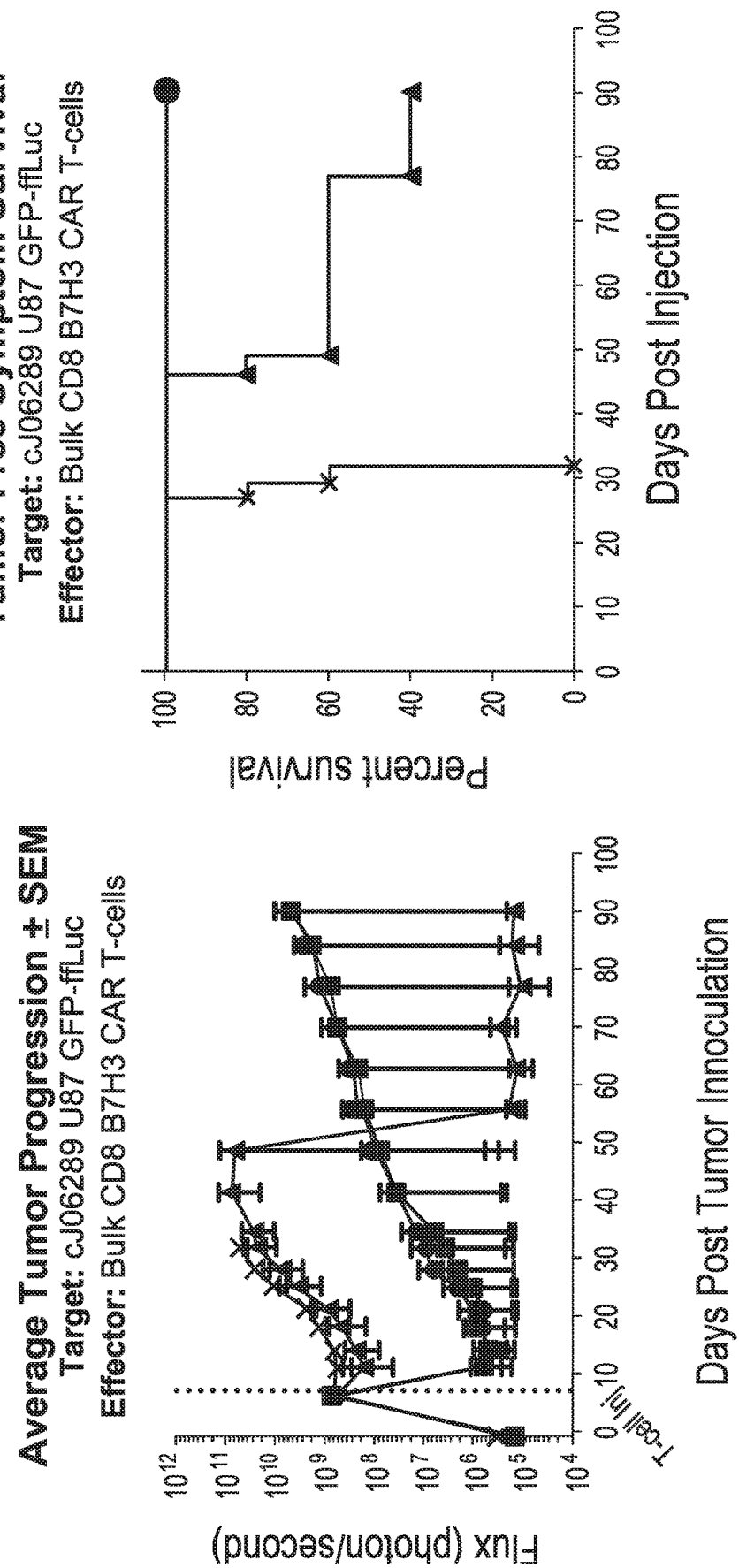
FIG. 2E is a series of graphs showing levels of B7H3$^+$ U87 tumor cells detected using a ffluc marker and survival rate by Kaplan Meier curve, in mice inoculated with U87 cells, and treated with CD8+ B7H3 CAR T cells containing CARs having either a short (S), medium (M), or long (L) spacer region. (X) mock; (●) B7H3 CAR with short spacer region; (●) B7H3 CAR with medium spacer region; and (▲) B7H3 CAR with long spacer region.
Figure 2E:
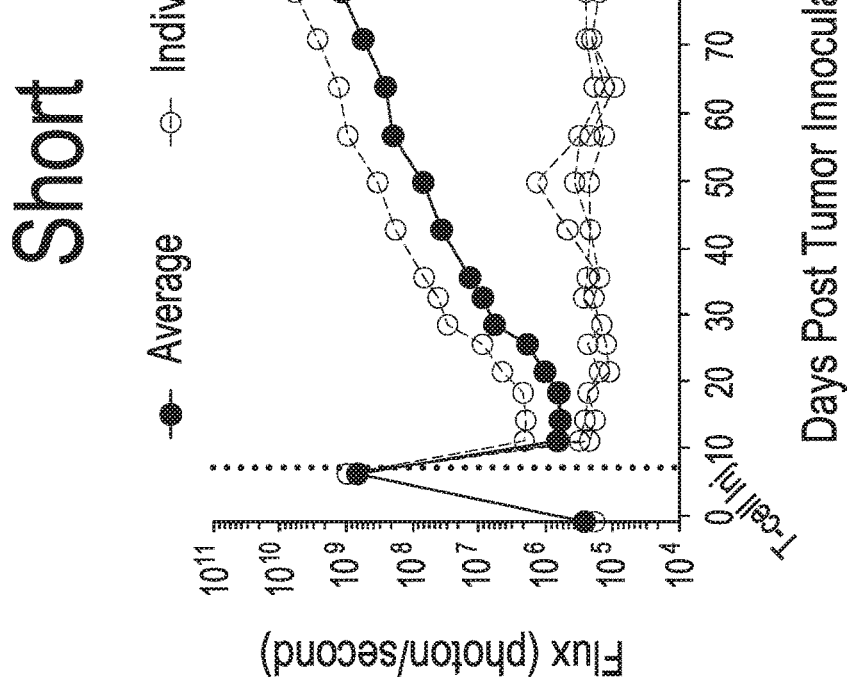
Figure 2E:
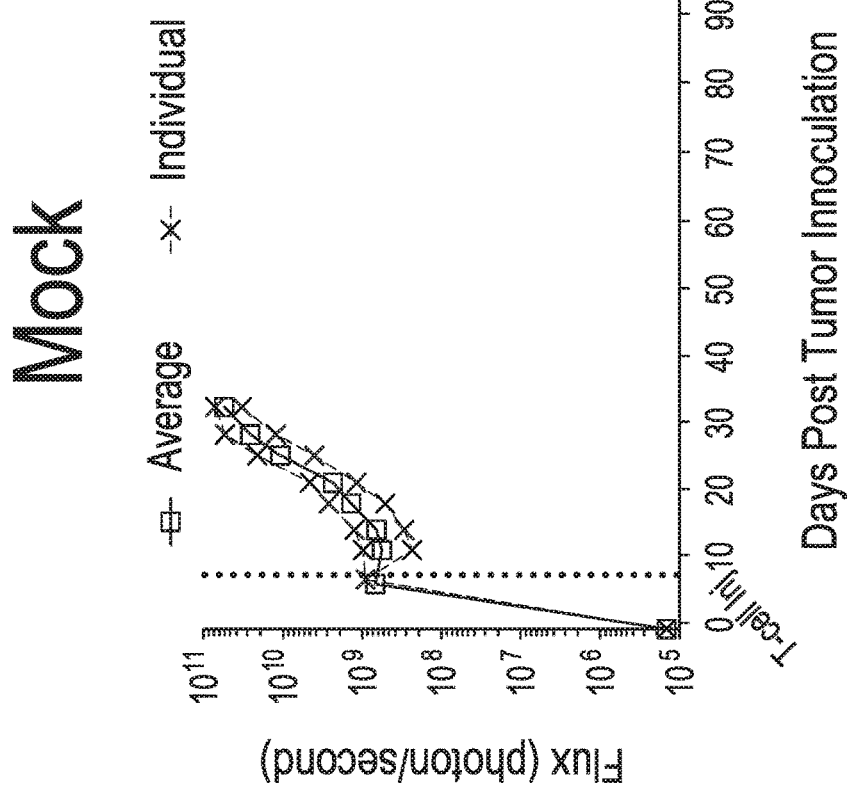
Figure 2E:
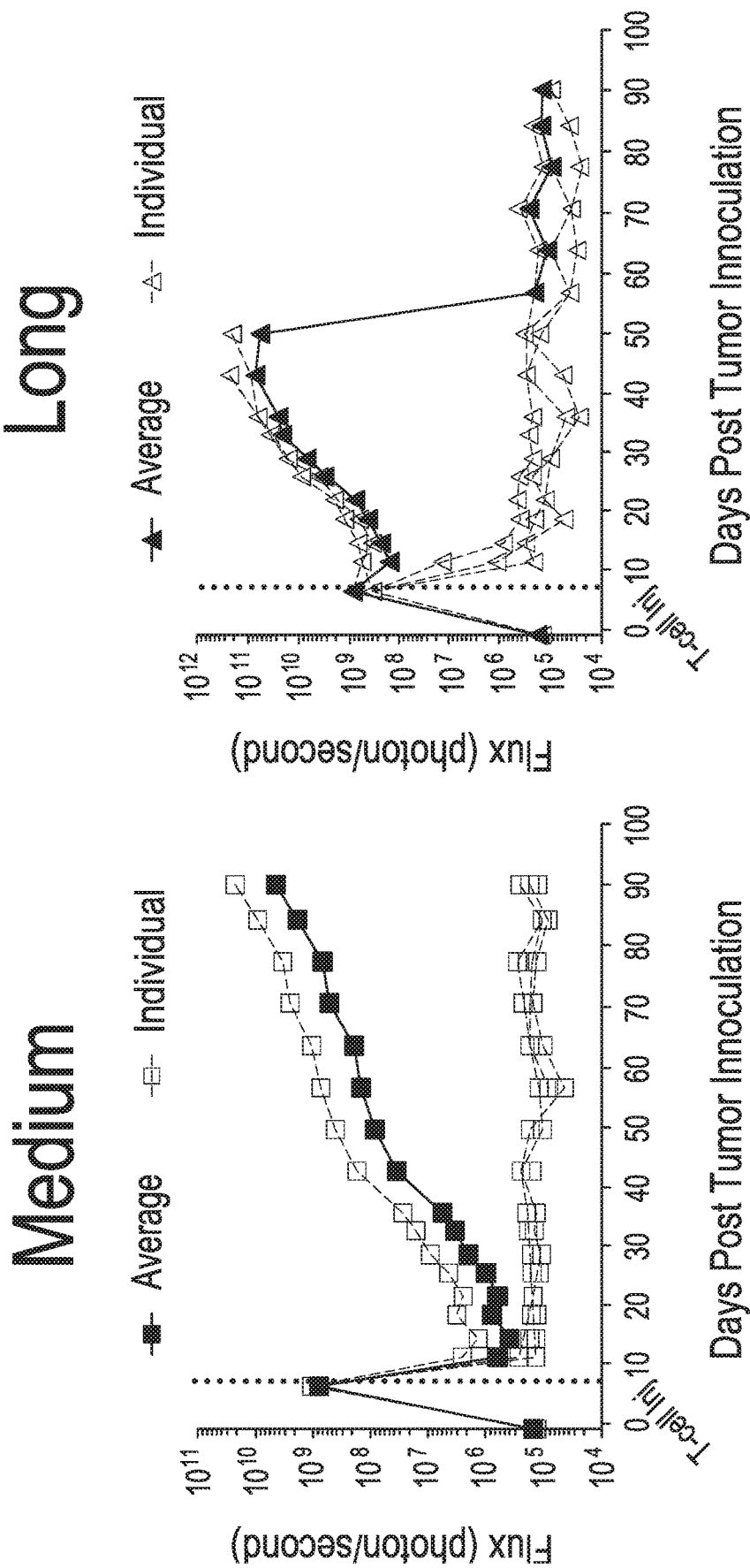

NOD-SCID mice were inoculated with U87 cells expressing a ffluc-eGFP marker. Mice were treated with CD8+ B7H3 CAR T cells having CARs with either the short (S), medium (M), or long (L) spacer regions. CD8+ B7H3 CAR T cells having CARs with either the short (S), medium (M), or long (L) spacer regions each reduced initial levels of detected U87 cells in mice. However, mice treated with CD8+ B7H3 CAR T cells having CARs with either the short (S) or medium (M) spacer regions demonstrated a much more substantial and dramatic initial decrease in detected U87 cells and increased survival rate, compared to mice treated with CD8+ B7H3 CAR T cells having a CAR with a long (L) spacer region (FIG. 2E). Thus, B7H3 CAR T cells having CARs with the medium (M) spacer region had much greater in vitro and in vivo activities, compared to B7H3 CAR T cells having CARs with either the short (S) or long (L) spacer regions.

Example 3—Methotrexate Selection of B7H3 CAR T Cells

Figure 3A:
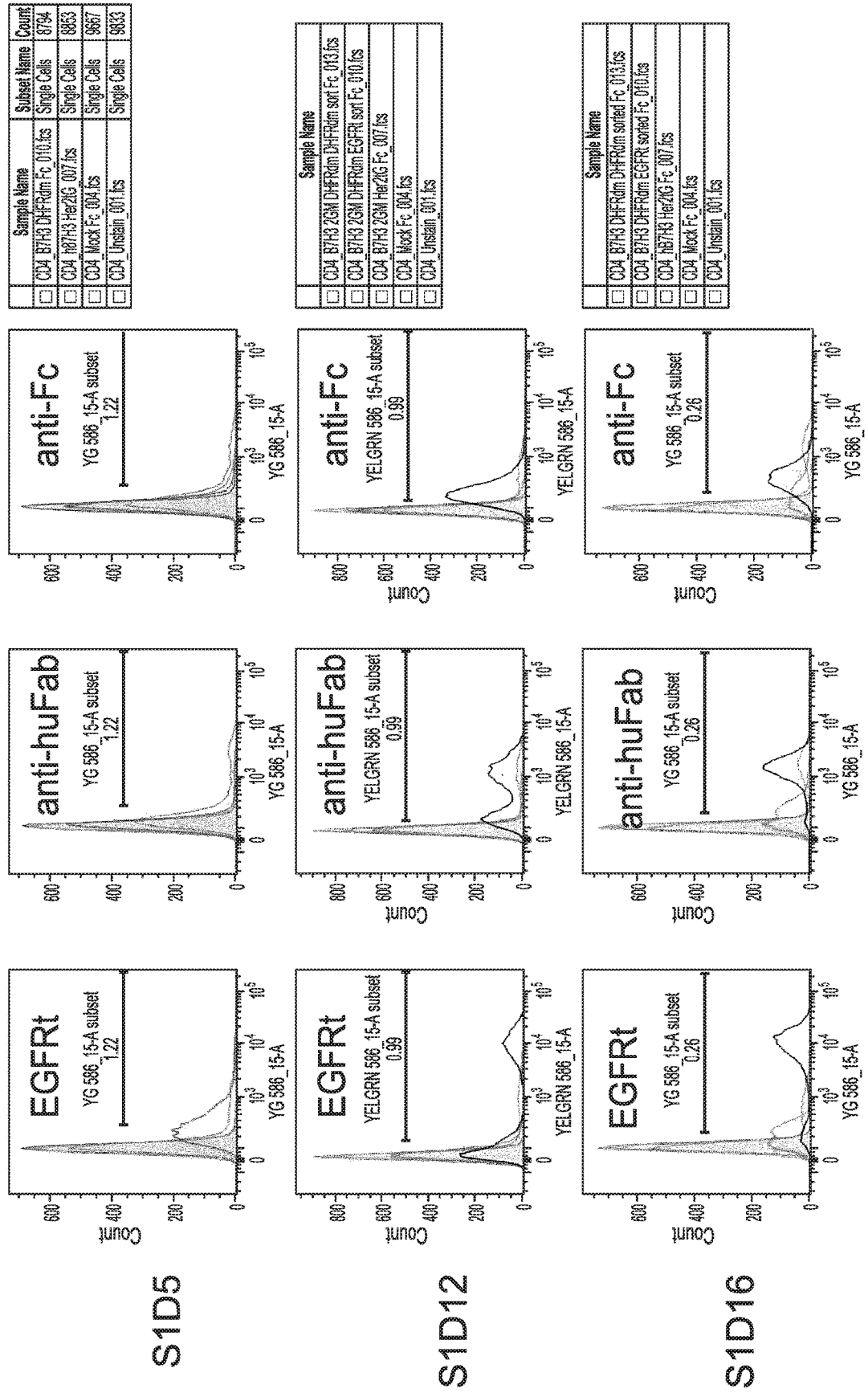
FIG. 3A is a series of graphs showing expression of EGFRt, human Fab, and Fc which binds anti-Fc in CD4+ cells transduced with a polynucleotide encoding a B7H3 CAR having a medium (M) spacer region, and a DHFRdm selectable marker.
Figure 3B:
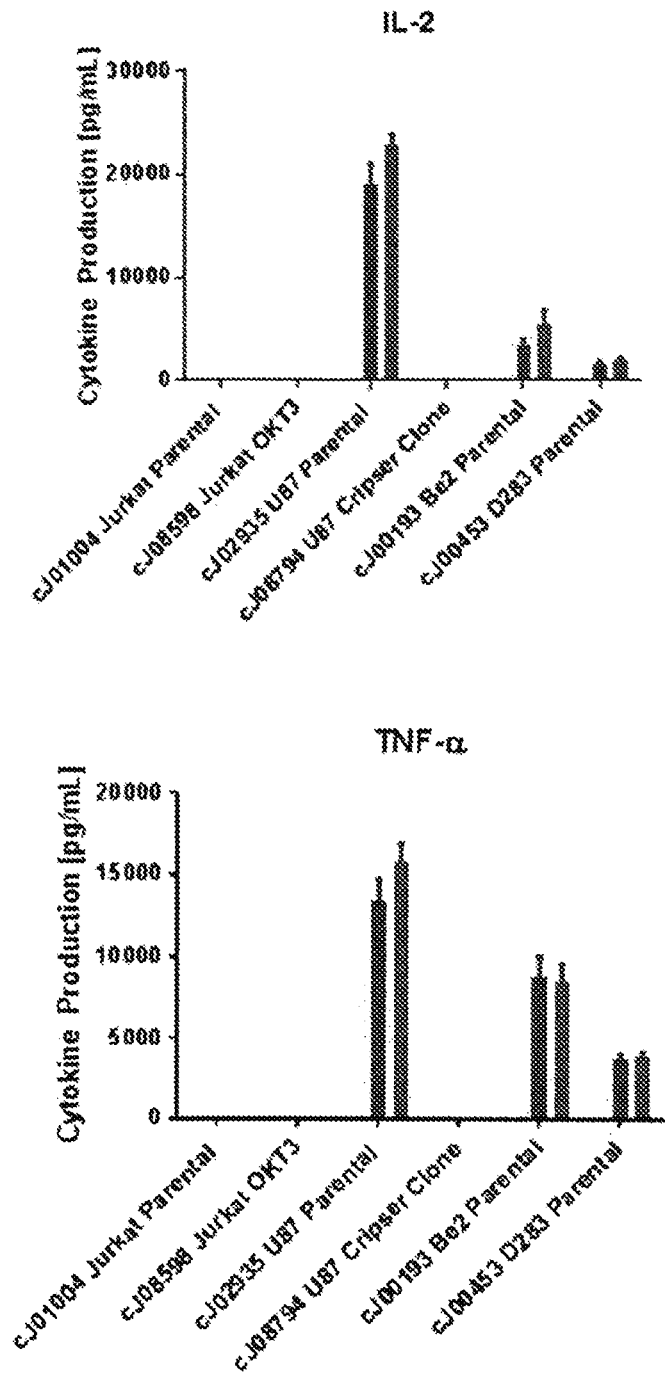
FIG. 3B is a series of graphs showing levels of cytokine release for CD4+ B7H3 CAR T cells stimulated with Jurkat cells, Jurkat OKT3 cells, U87 cells, modified U87 cells lacking B7H3 expression, Be2 cells, and D283 cells. Measured cytokines include IFNγ, IL-2, and TNF.
Figure 3B:
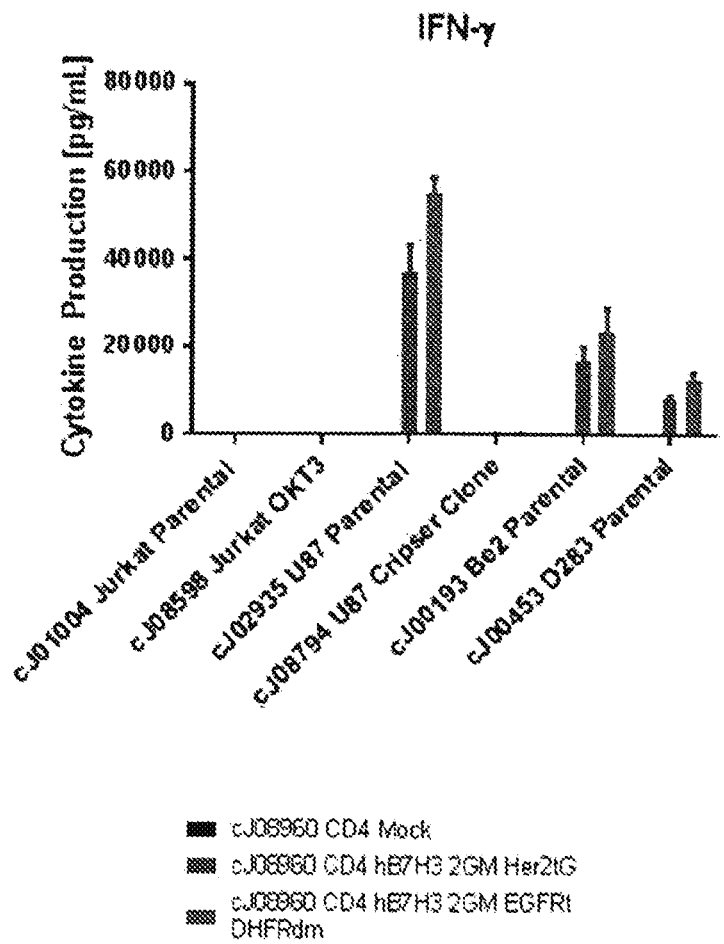

CD4+ T cells were transduced with viral vectors containing a polynucleotide encoding a B7H3 CAR having the medium spacer region, and a DHFR double mutant (DHFRdm) selectable marker. Cells were treated with methotrexate. Expression of EGFRt, human Fab, and human Fc were measured over the culture period for different transduced populations (FIG. 3A). EGFRt, human Fab, and human Fc were expressed in treated cells.

in vitro cytokine production was measured for B7H3 CAR T cells against various cell lines including Jurkat cells (T cell line), Jurkat OKT3 cells, U87 cells, modified U87 cells lacking B7H3 expression, Be2 cells, and D283 cells. Cytokine production was measured for B7H3 CAR T cells stimulated with U87, Be2, and D283 cells (FIG. 3B). The addition of a drug selection gene (DHFRdm) allows for the enrichment of CAR expressing T cells in the presence of Methotrexate.

Example 4—Production Run T Cells Lyse B7H3 Positive Target Cell Lines

Figure 4:
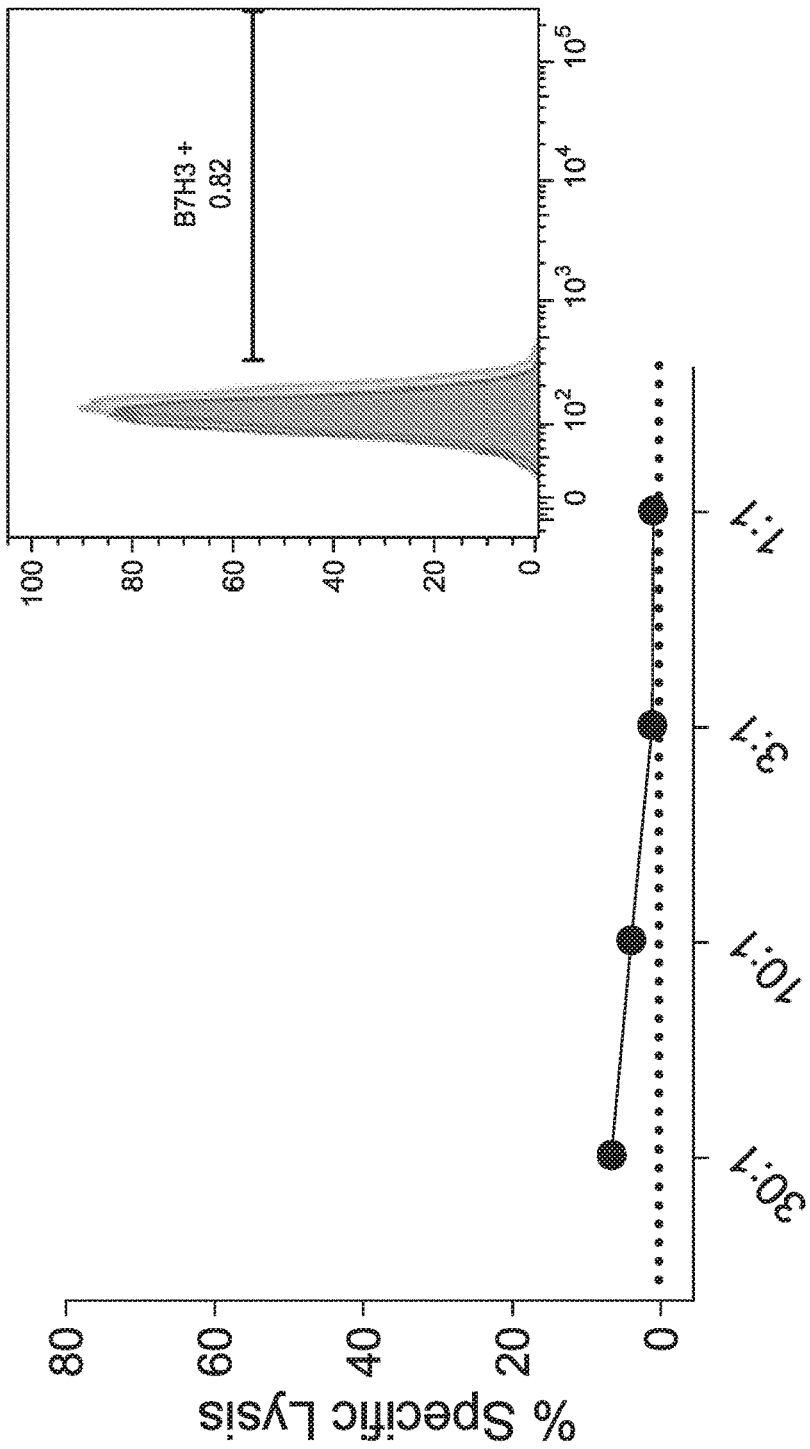
FIG. 4 is a series of graphs showing data related to lysis of B7H3 positive target cell lines by T cells (Example 4).
Figure 4:
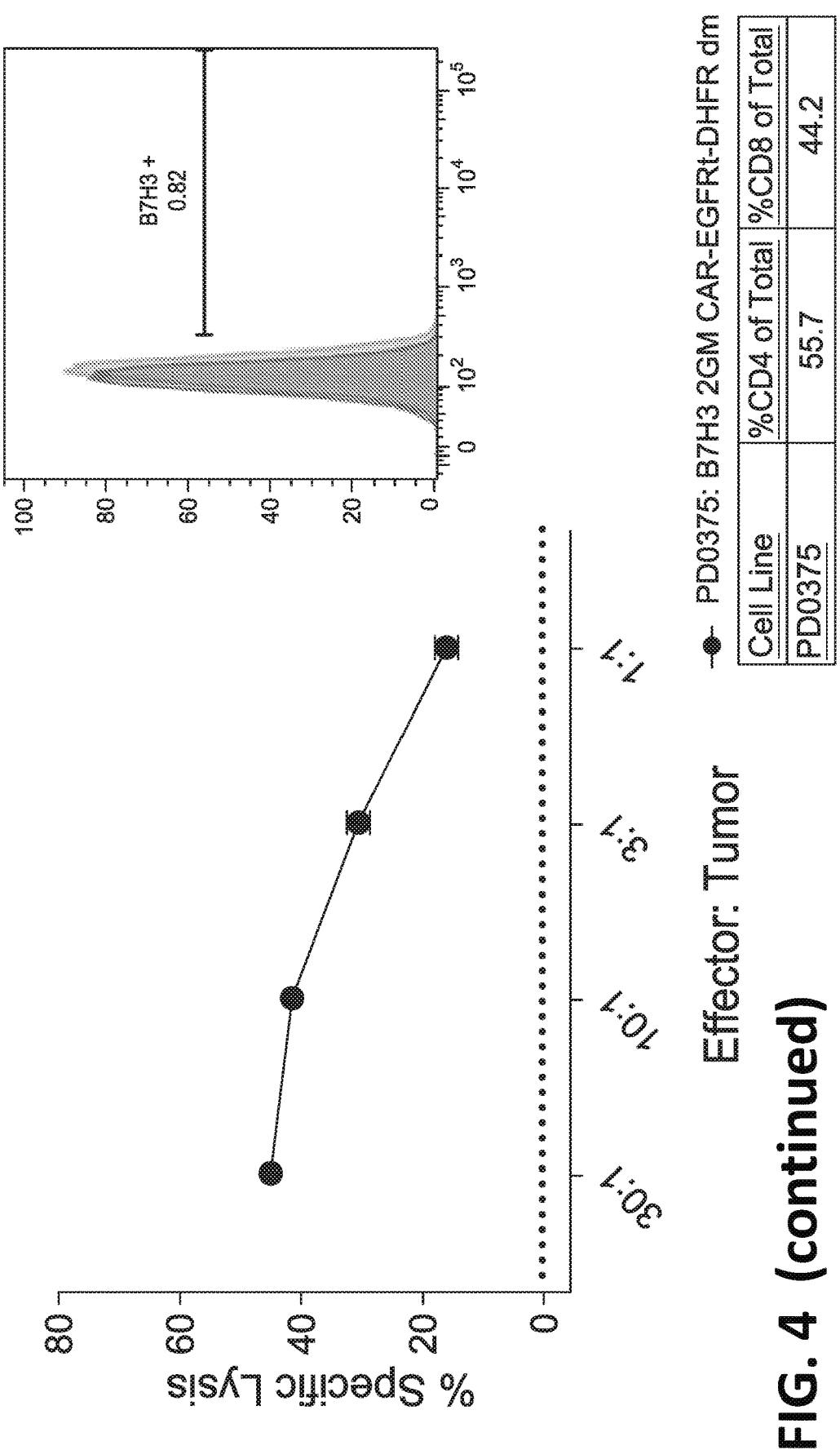
Figure 4:
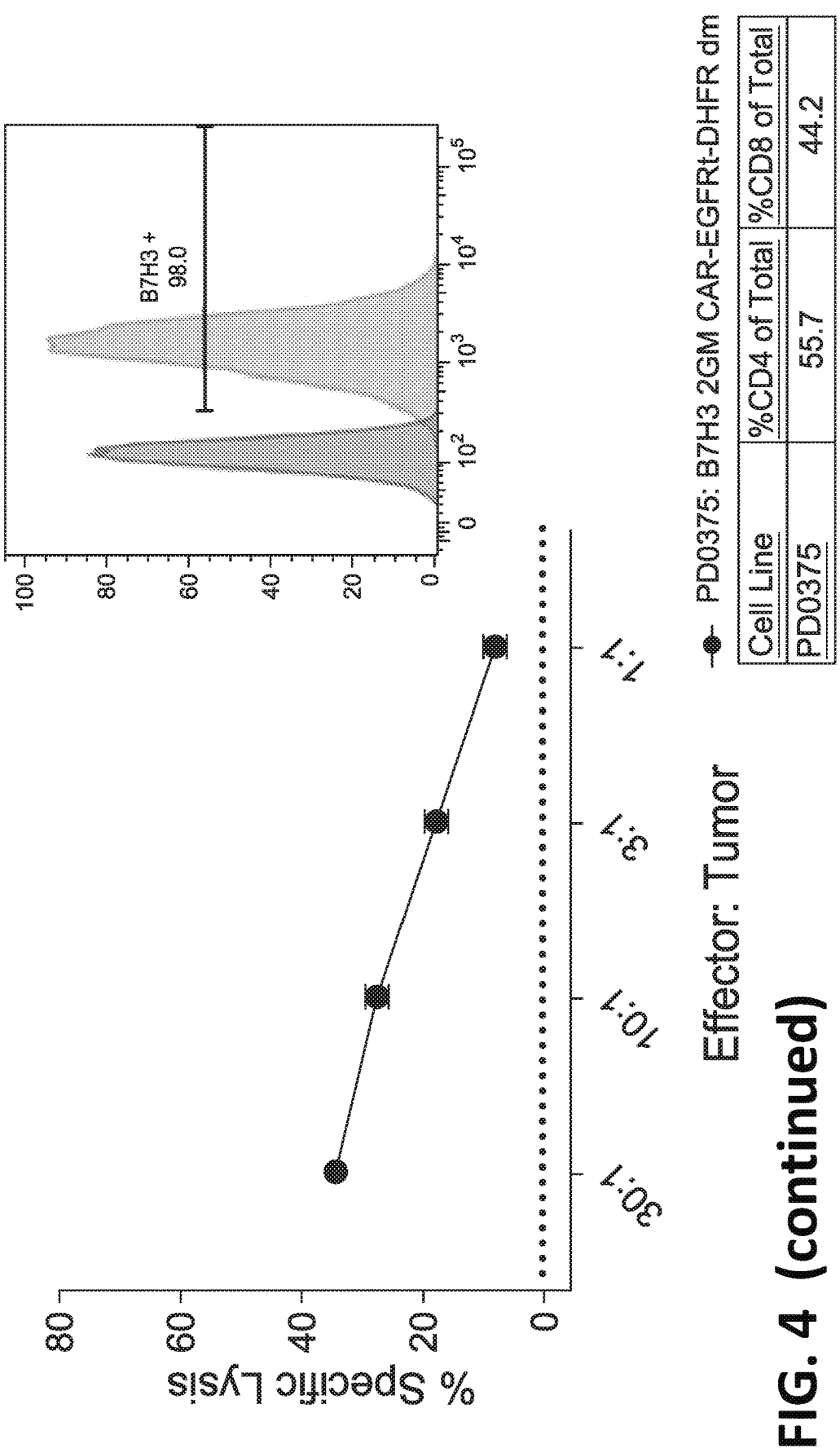
Figure 4:
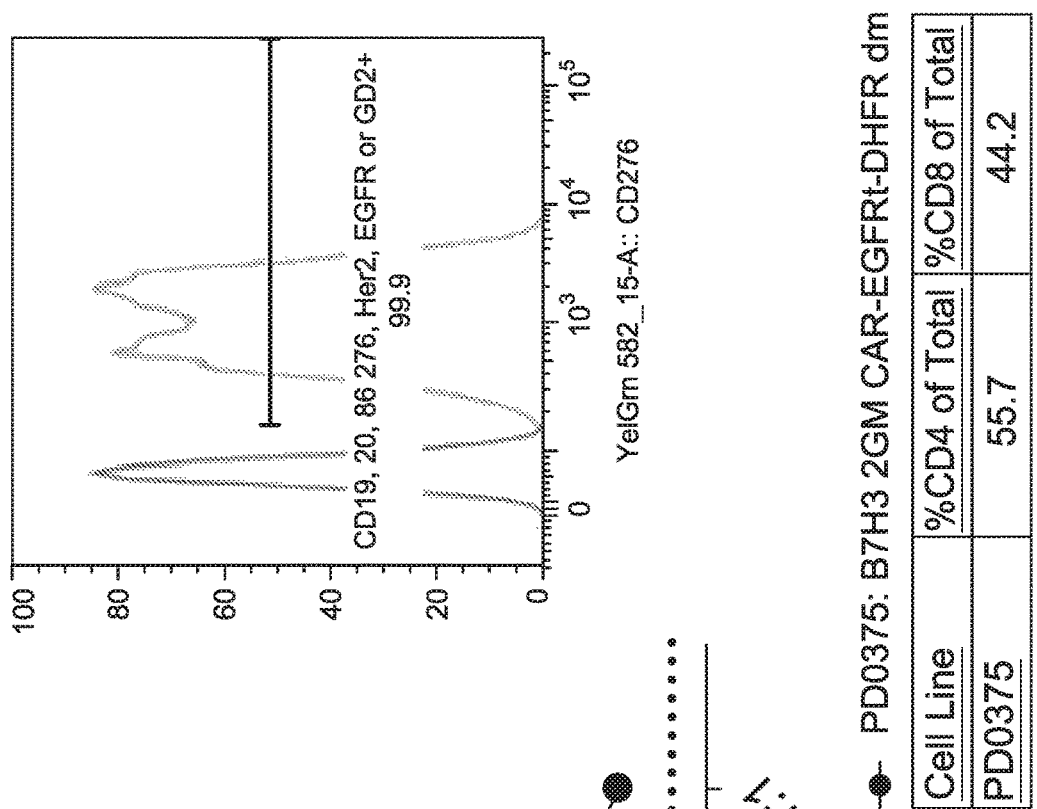
Figure 4:
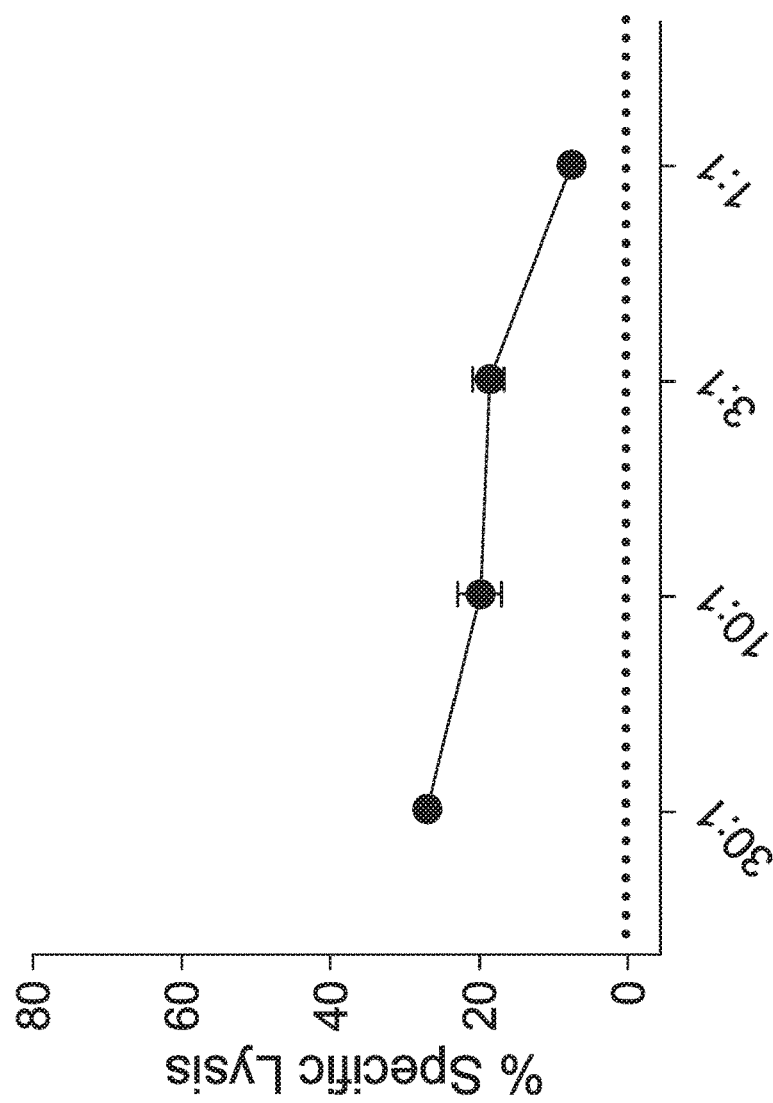
Figure 4:
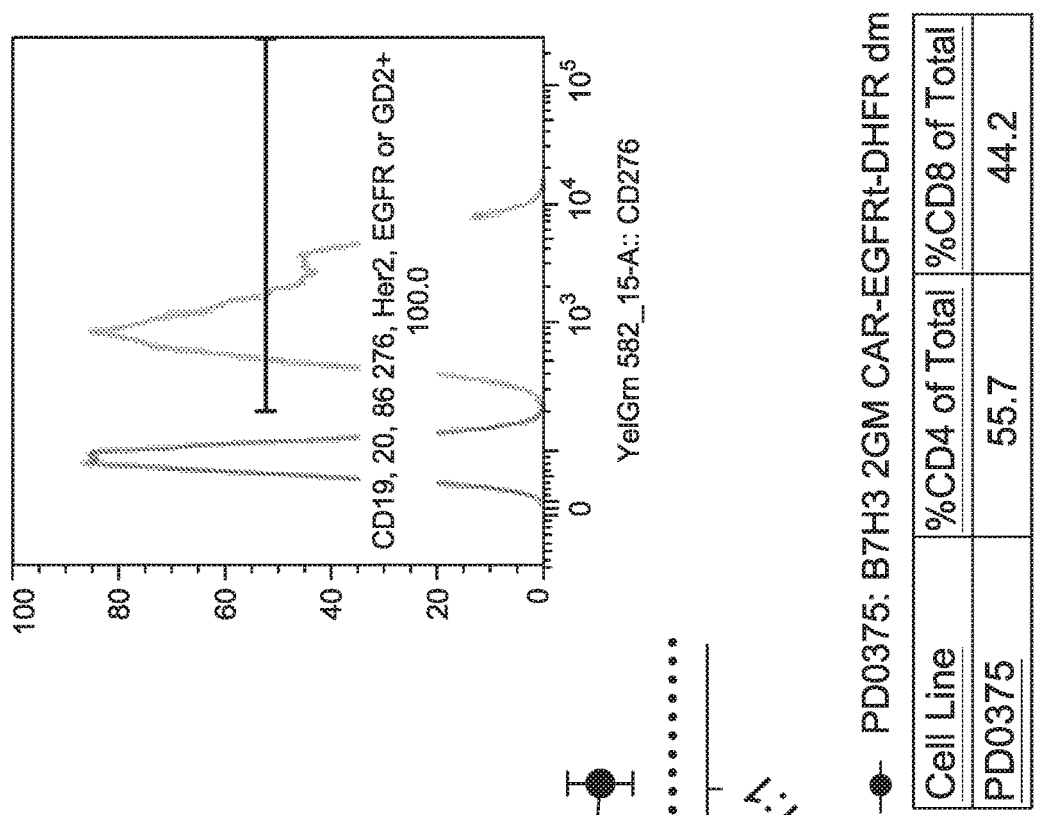
Figure 4:
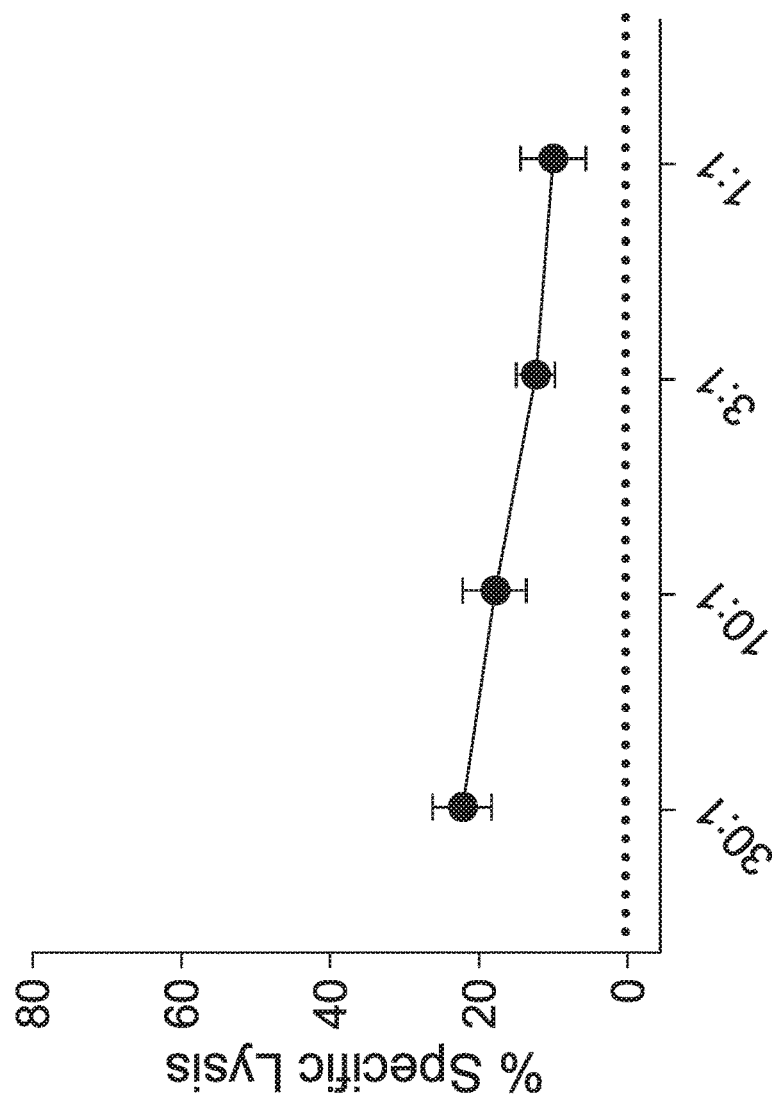
Figure 4:
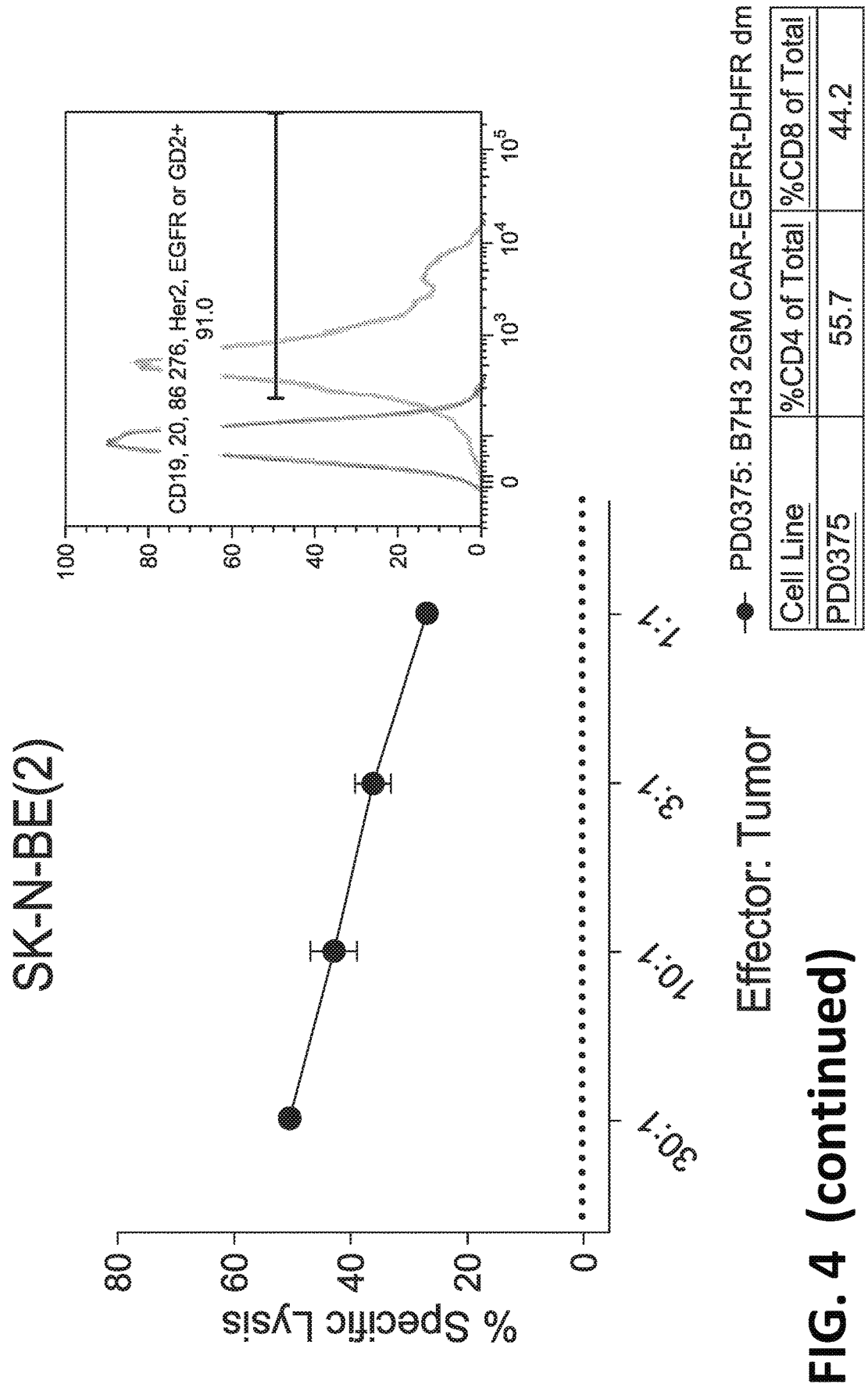
Figure 4:
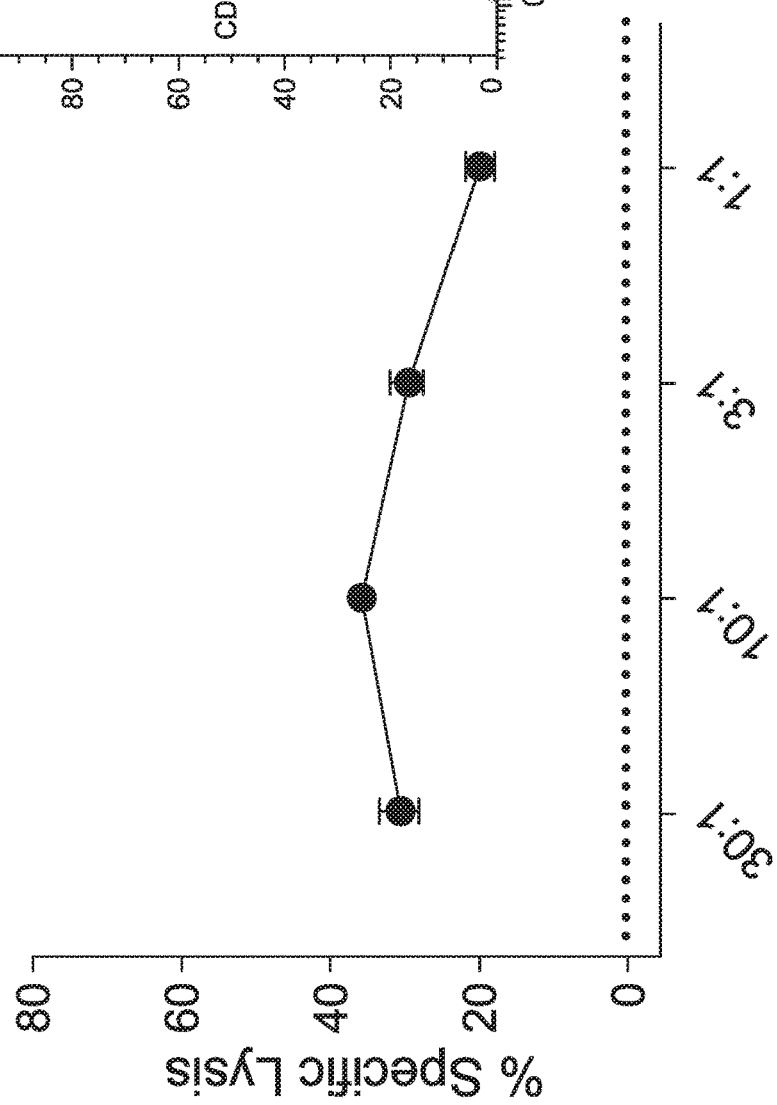

Target $^{51}$Cr labeled B7H3− (K562 B7H3 KO), control cells (K562 B7H3 KO+OKT3), or B7H3+ cell lines (K562 parental, U87MG, U251TMG, SKNBE2, and D283 med), were co-cultured with 2GM B7H3 CAR T cells for four hours. Specific lysis was measured using a scintillation counter (FIG. 4). The T cells were a mix of CD4 T cells (55.7% of total) and CD8 T cells (44.2% of total) that were >95% EGFRt positive. Histogram insets display B7H3 positivity for each target tumor cell. Little to no specific lysis was detected against the B7H3− K562 B7H3 KO cell line. In contrast, significant specific lysis against the control and experimental cell lines was observed.

Thus, the data show that B7H3CAR T cells specifically lyse B7H3+ control and experimental cell lines.

Example 5—Production Run T Cells Produce Cytokine Upon Co-Culture with B7H3 Positive Target Cell Lines Target B7H3− (K562 B7H3 KO), control cells (K562 B7H3 KO+OKT3), or B7H3+ cell lines (K562 parental, U87MG, U251TMG, SKNBE2, and D283 med), were co-cultured with 2GM B7H3CAR T cells for twenty-four hours. The T cells were a mix of CD4 T cells (55.7% of total) and CD8 T cells (44.2% of total) that were >95% EGFRt positive. The graphs (FIG. 5) show levels of cytokine release for Mock or B7H3CAR T cells when stimulated by co-culture with various targets of interest. Measured cytokines included IFNγ, IL-2, and TNFα.

Figure 5:
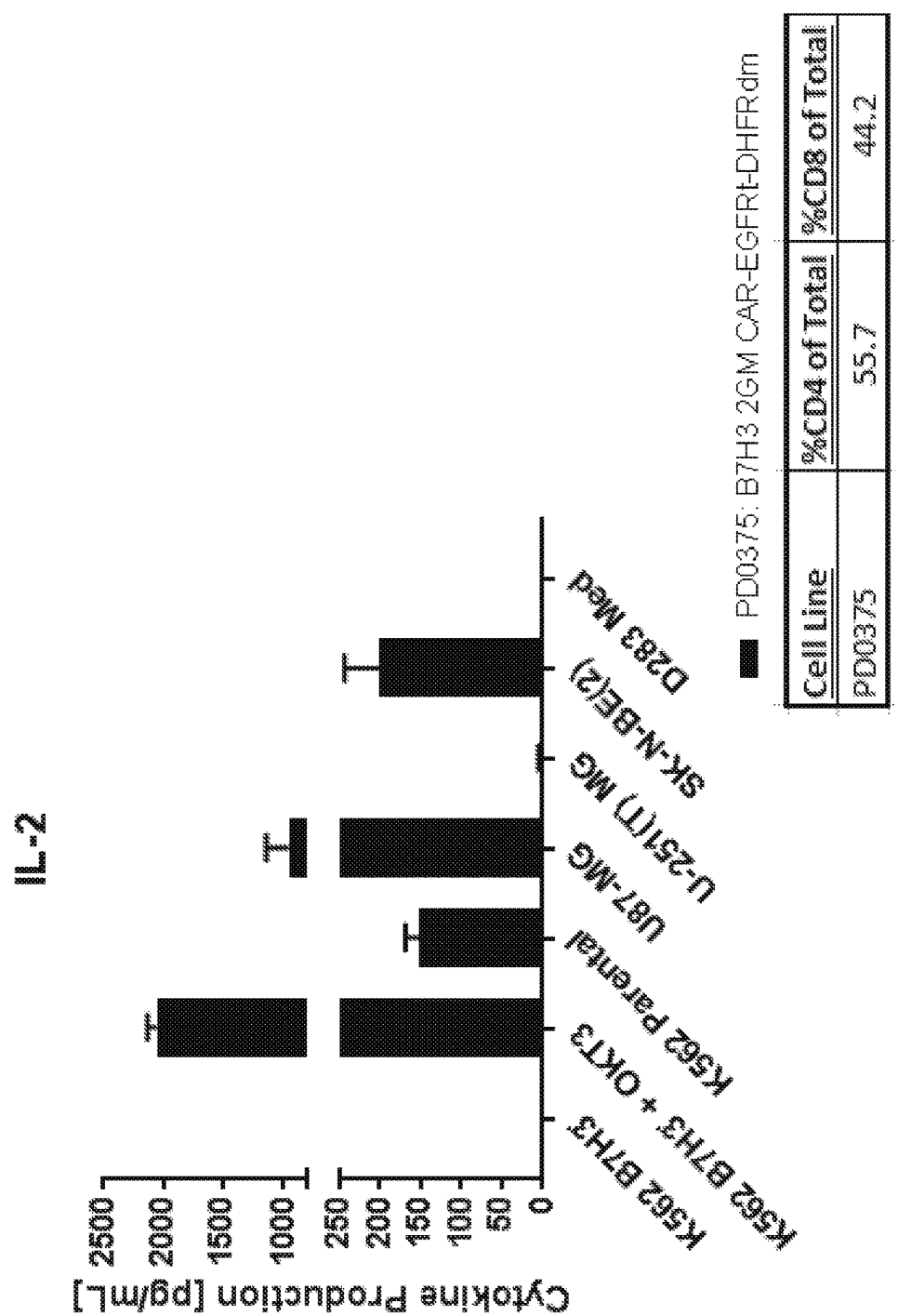
FIG. 5 is a series of graphs showing data related to production of cytokines by T cells co-cultured with B7H3 positive target cell lines (Example 5).
Figure 5:
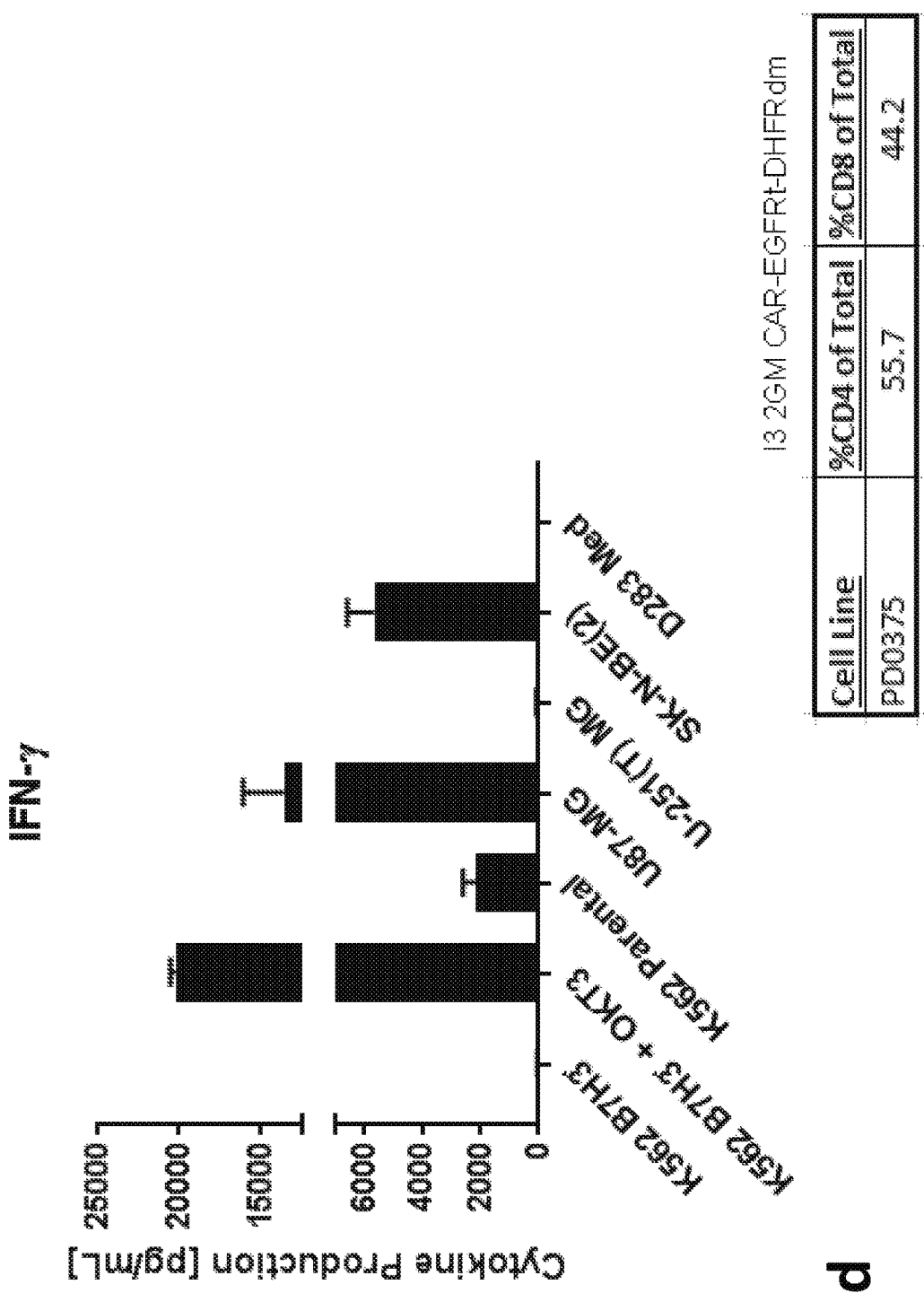
Figure 5:
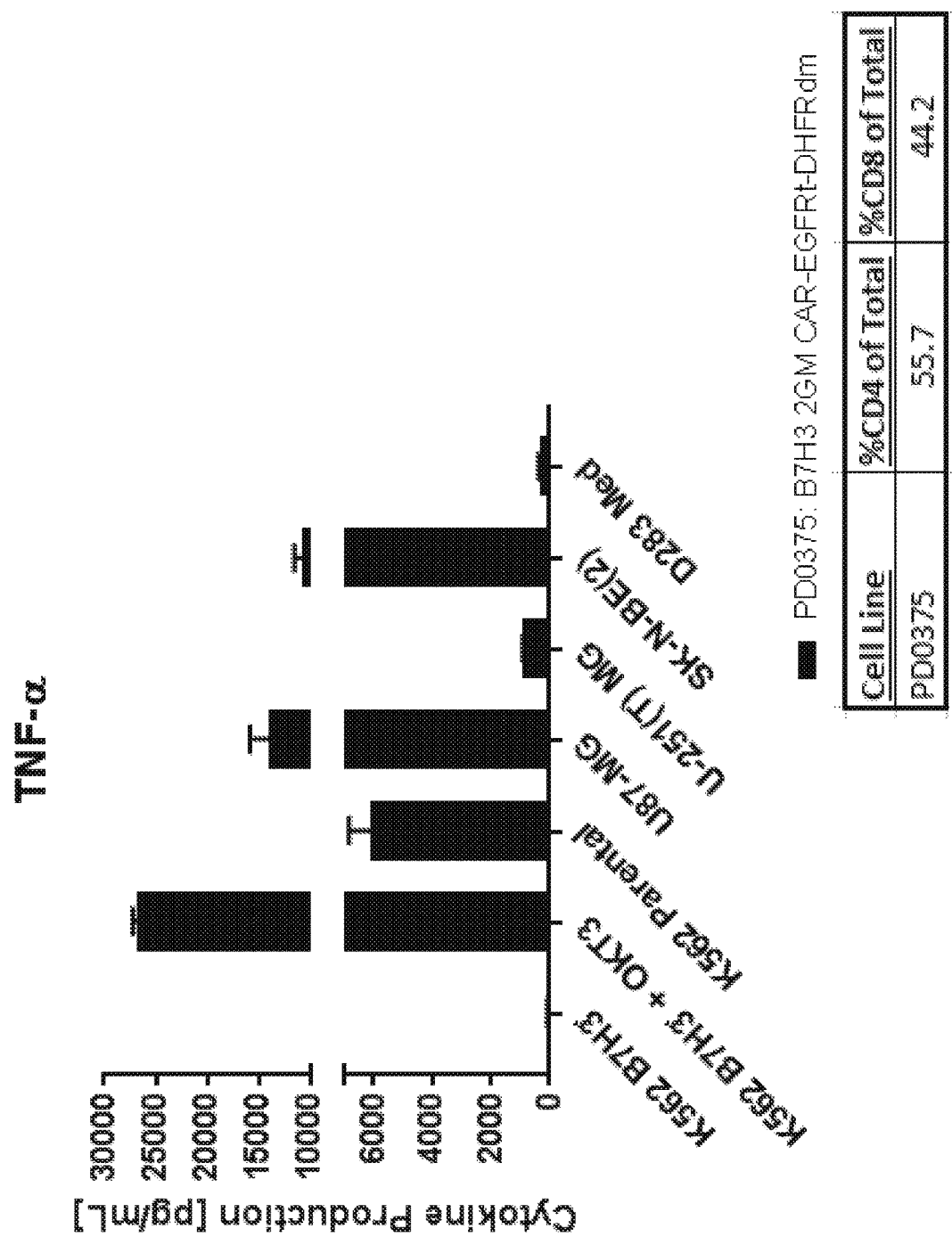

Data showed that T cells co-cultured with control cells (K562 B7H3 KO+OKT3), or B7H3+ cell lines (K562 parental, U87MG, and SKNBE2), whereas no B7H3-(K562 B7H3 KO) produced cytokines IFNγ, IL-2, and TNFα, whereas T cells co-cultured with B7H3− (K562 B7H3 KO) did not produce any of these cytokines (FIG. 5).

Example 6—Production Run T Cells can Eradicate U87 Tumor Cells In Vivo

Figure 6:
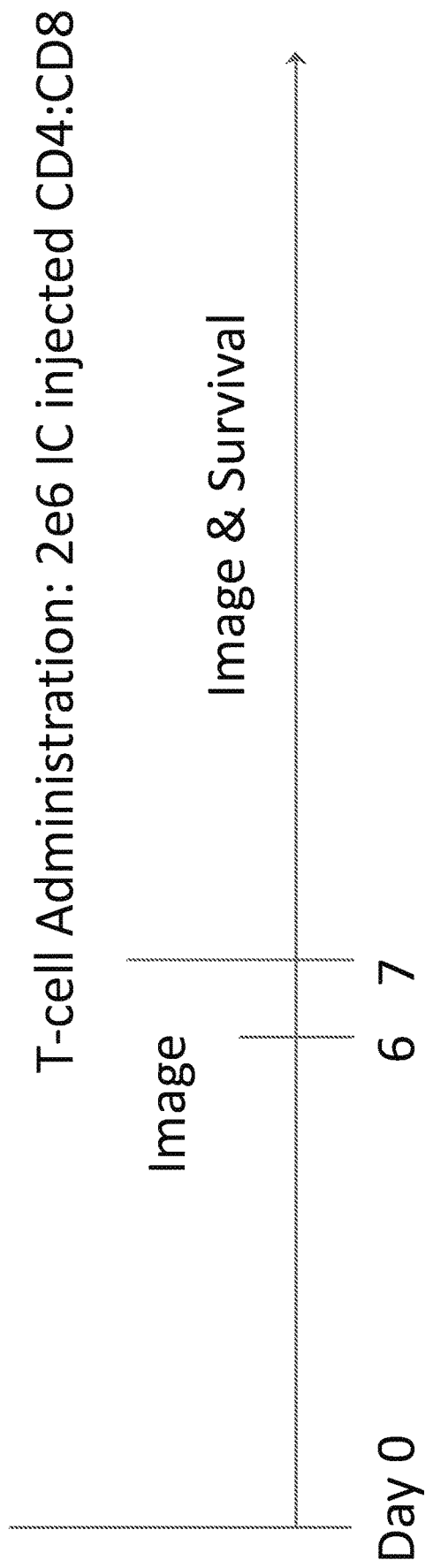
FIG. 6 is a series of graphs showing data related to eradication by T cells of U87 tumor cells in vivo (Example 6).
Figure 6:
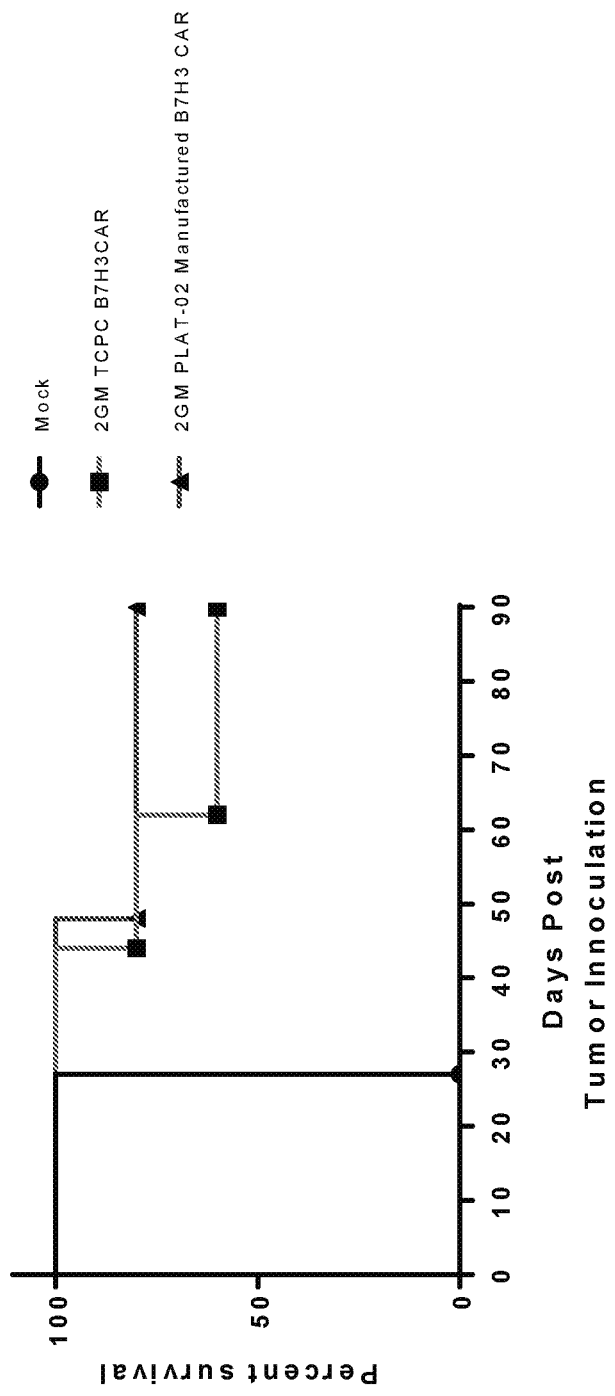
Figure 6:
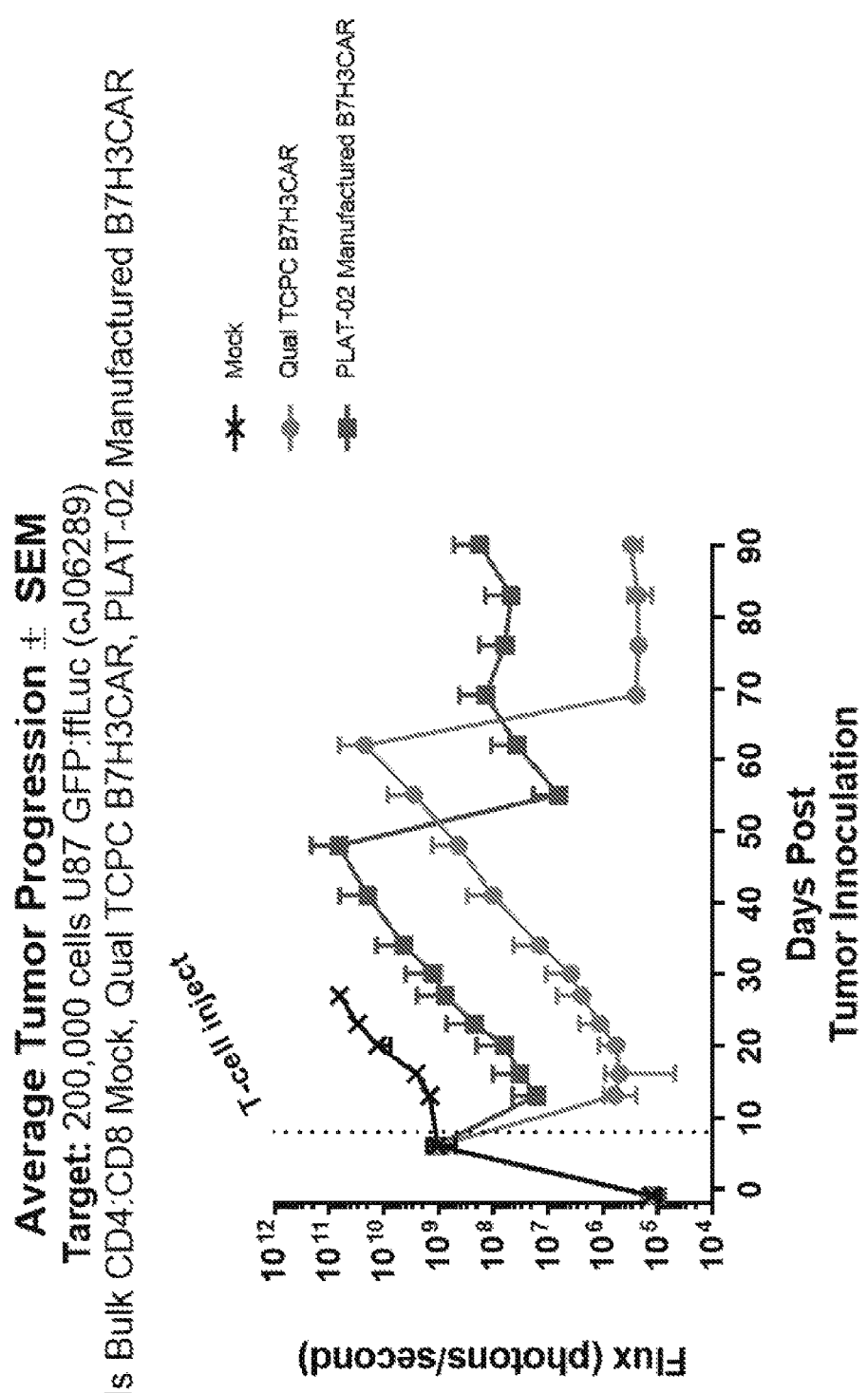
Figure 6:
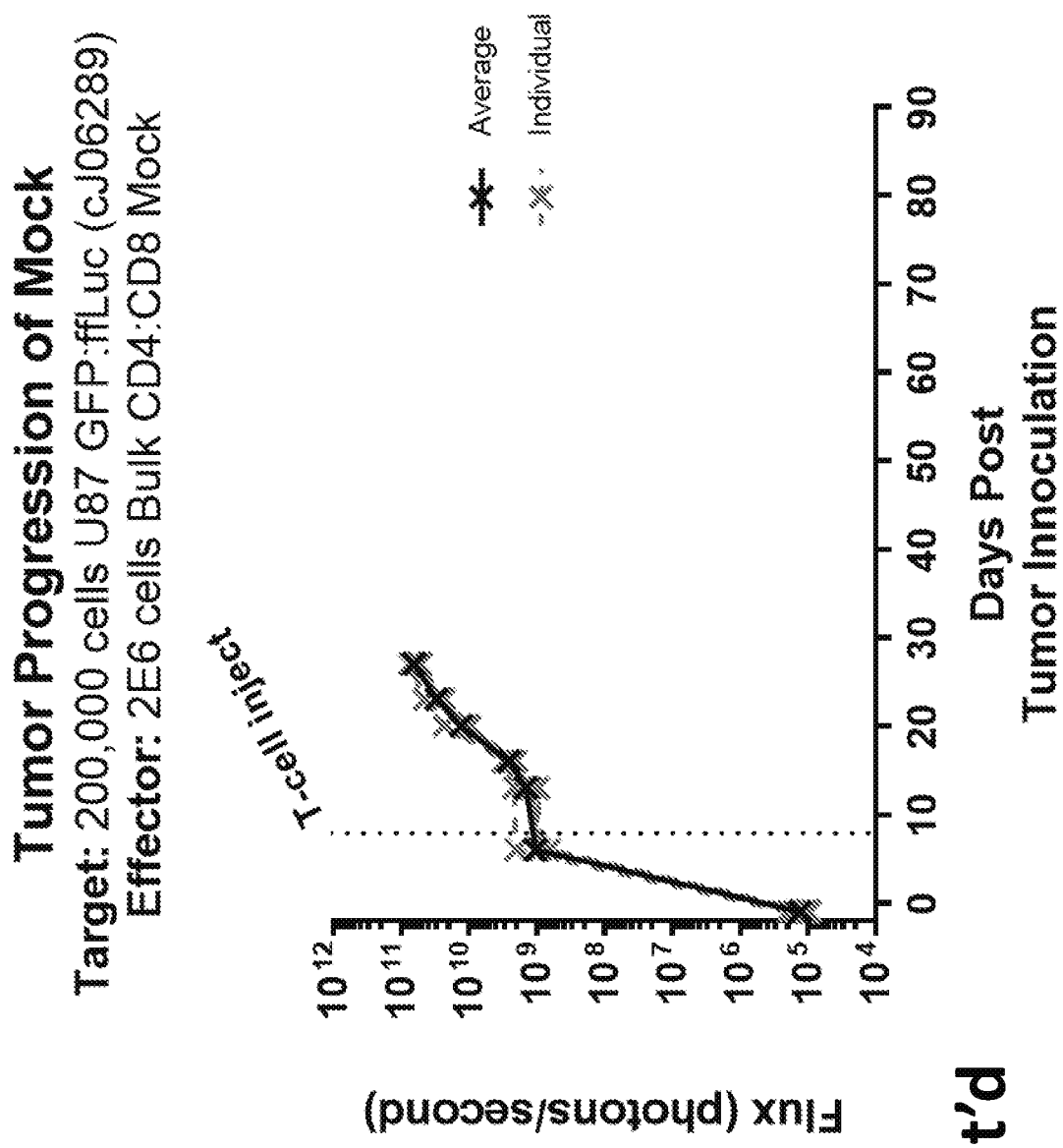
Figure 6:
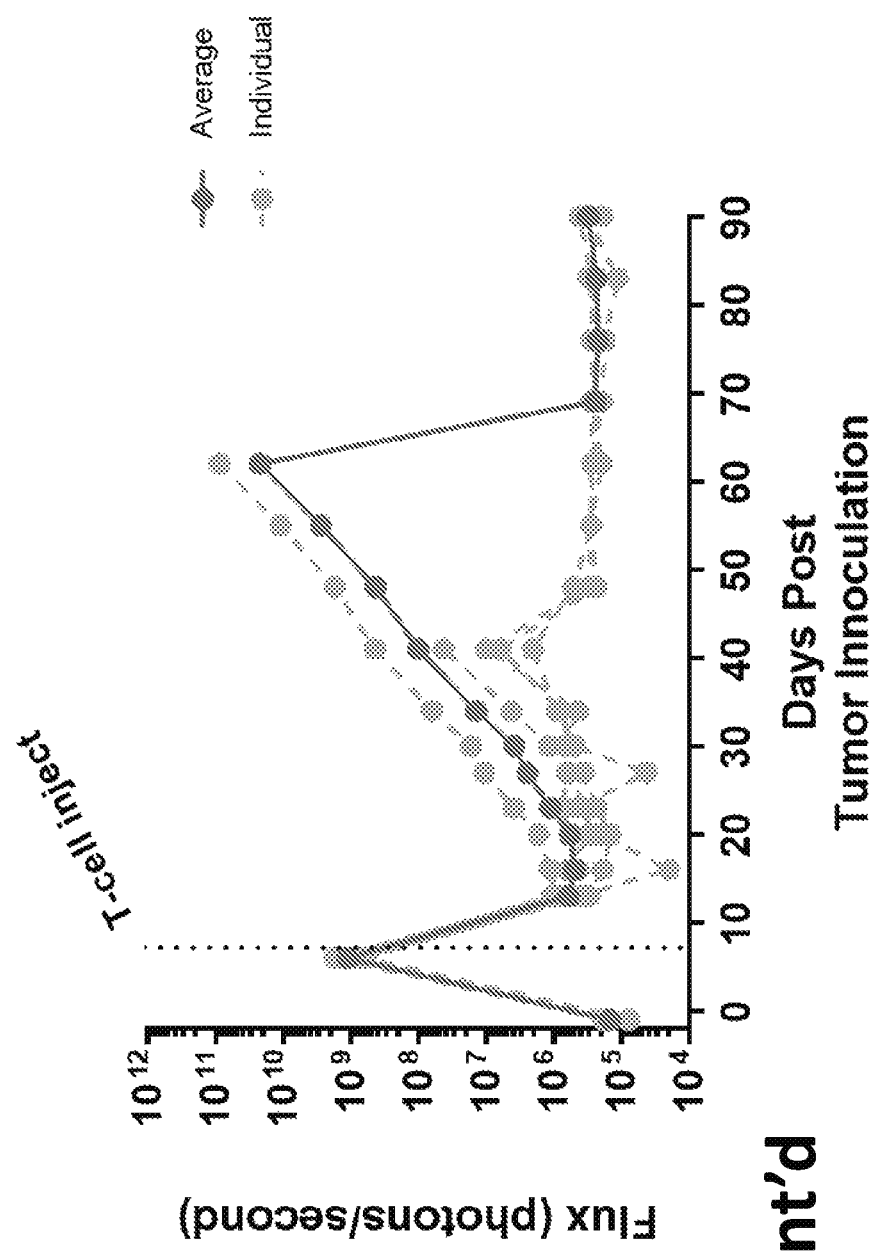
Figure 6:
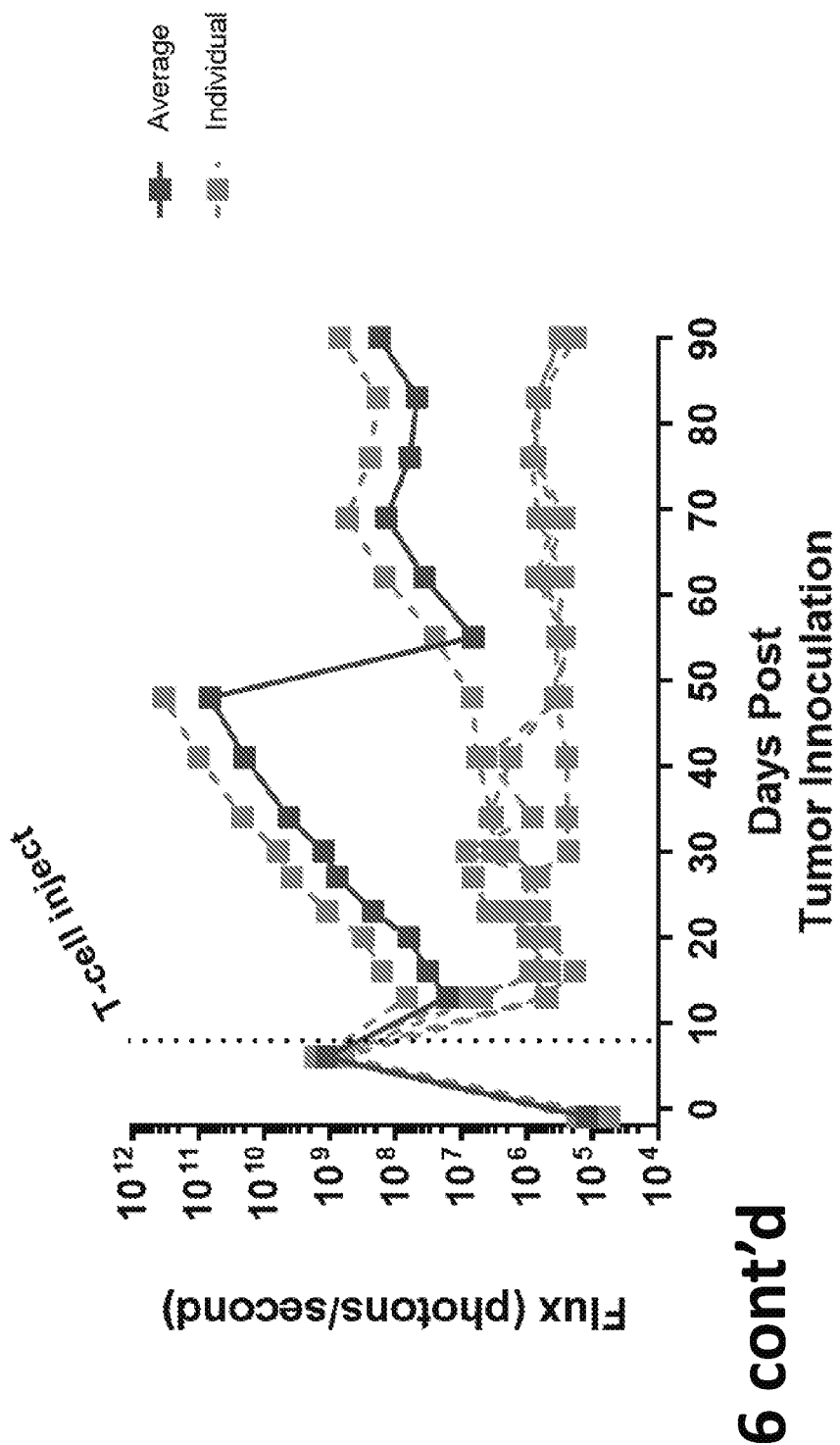

FIG. 6 shows levels of B7H3+U87 tumor cells detected using a ffluc marker and survival rate, in mice inoculated with U87 cells, and treated with CD4 and CD8+ B7H3 CAR T cells produced by the current tissue culture production center (TCPC) T cell production protocol and the previous PLAT-02 production protocol.

Approximately, 200,000 U87 GFP:ffluc (cJ06289) tumor cells were injected intracranially into mice on Day 0 (FIG. 6). On Day 6, flux analysis (by imaging) was performed to confirm the presence of tumor cells in the mice (FIG. 6). On Day 7, 2×10$^6$ 1:1 CD4:CD8 T cells were administered intracranially in the same coordinates. Flux analysis (by imaging) and survival was monitored until the end of study, i.e., Day 90 (FIG. 6).

Data showed that both B7H3CAR T cell populations were able to reduce flux and prolong survival in this intracranial U87 model (FIG. 6). Thus, the data showed that B7H3CAR T cells were able to eradicate U87 tumor cells in vivo.

Example 7—Production Run T Cells can Eradicate Subcutaneous Tumor Cells In Vivo

Figure 7:
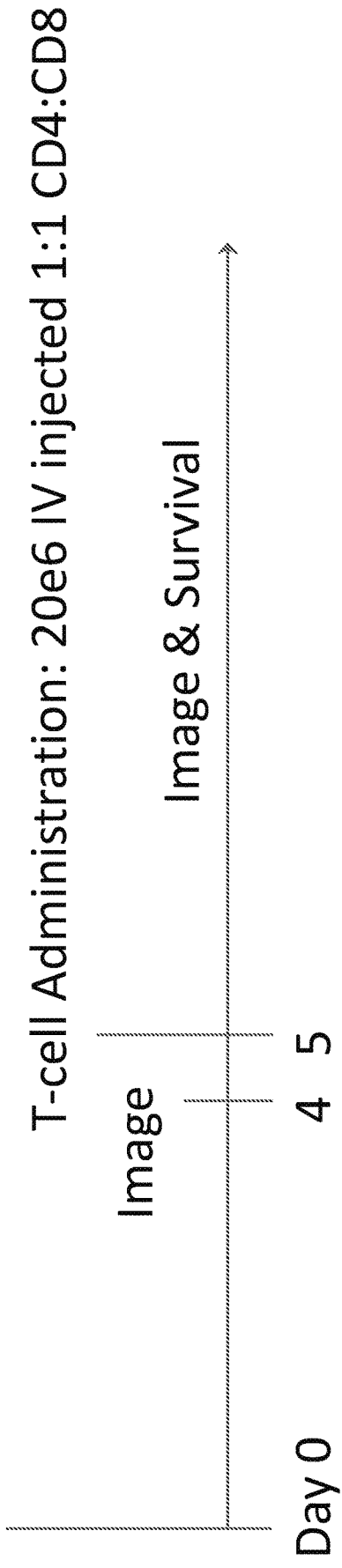
FIG. 7 is a series of graphs showing data related to eradication by T cells of subcutaneous Be2 neuroblastoma tumor cells in vivo (Example 7).
Figure 7:
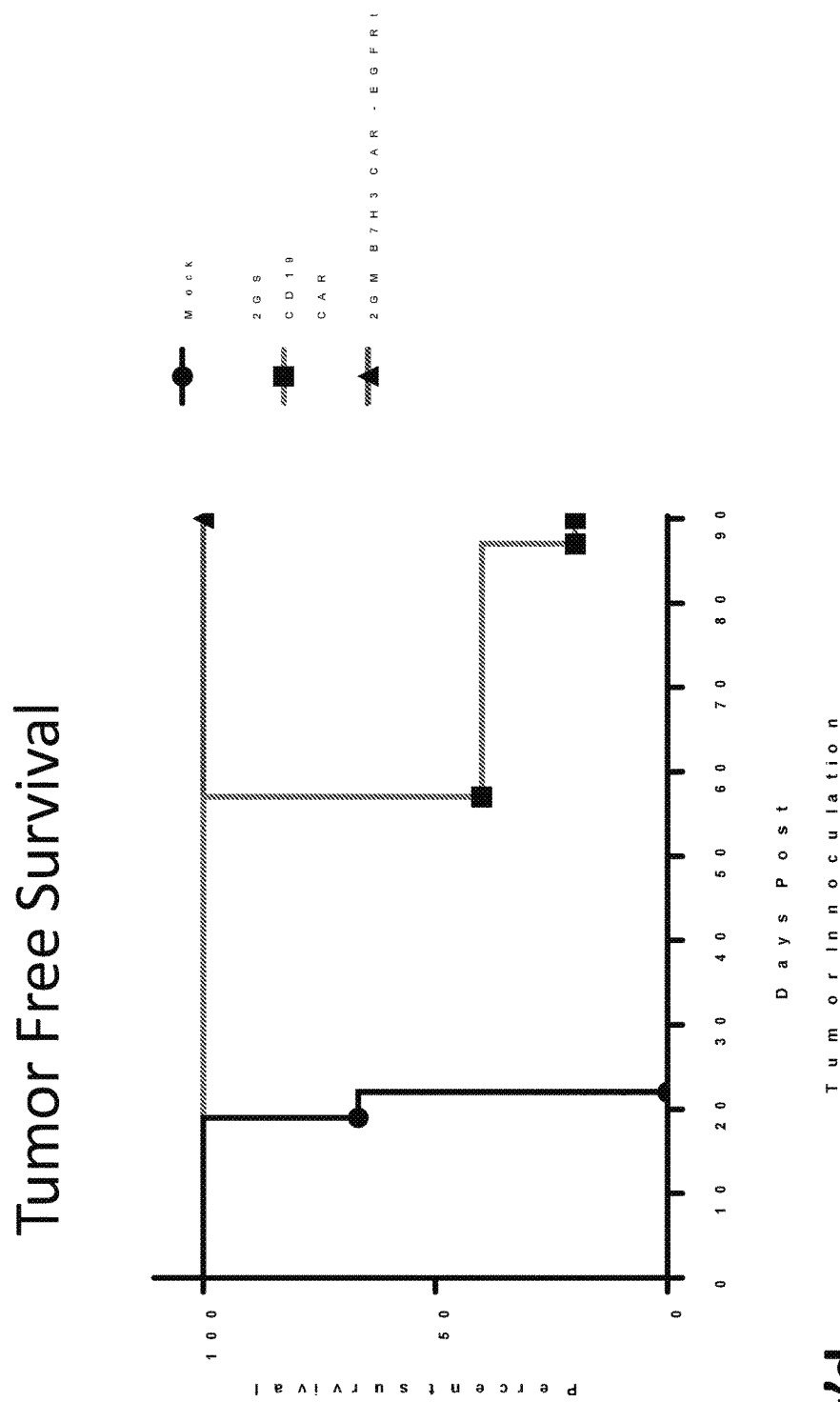
Figure 7:
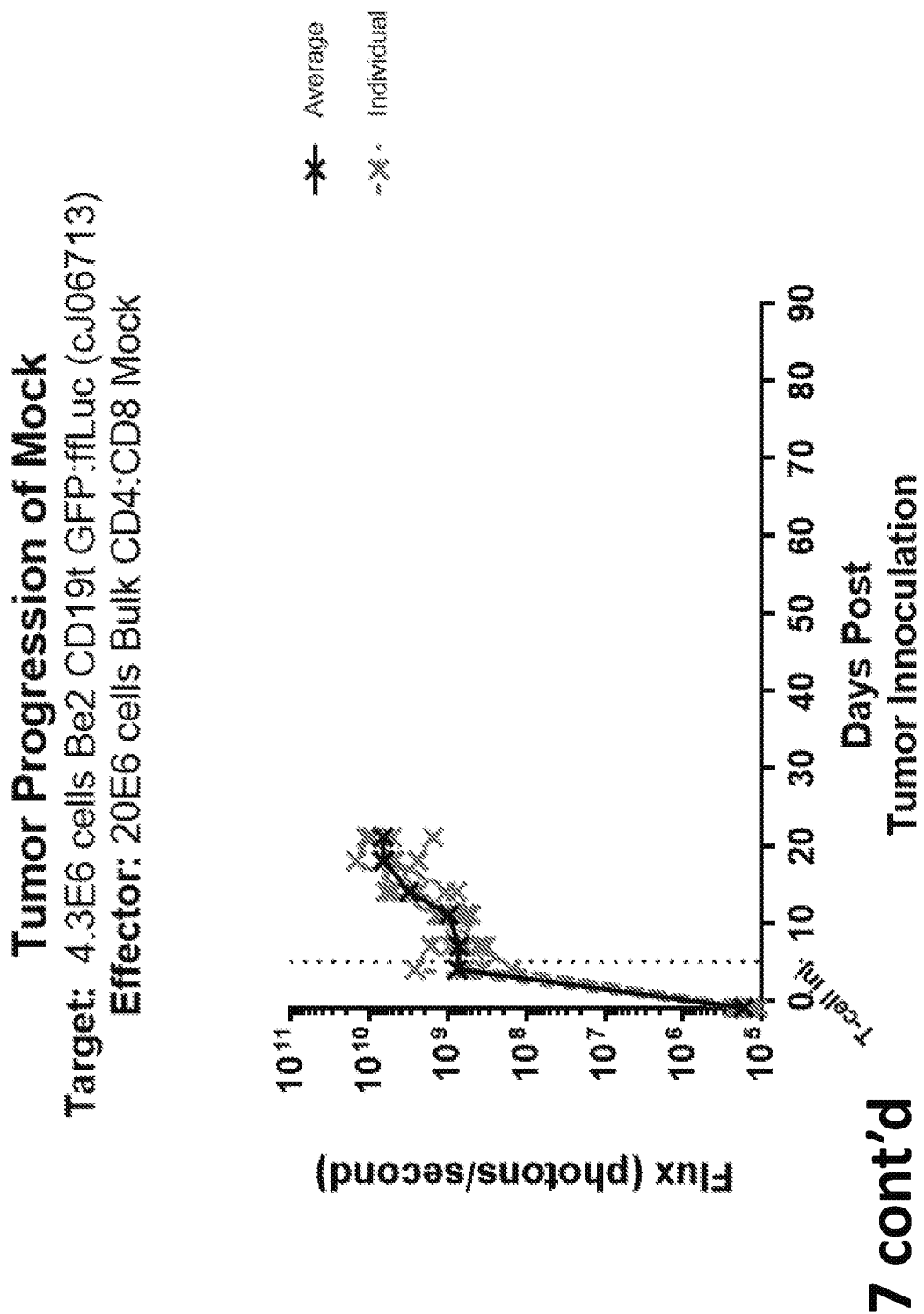
Figure 7:
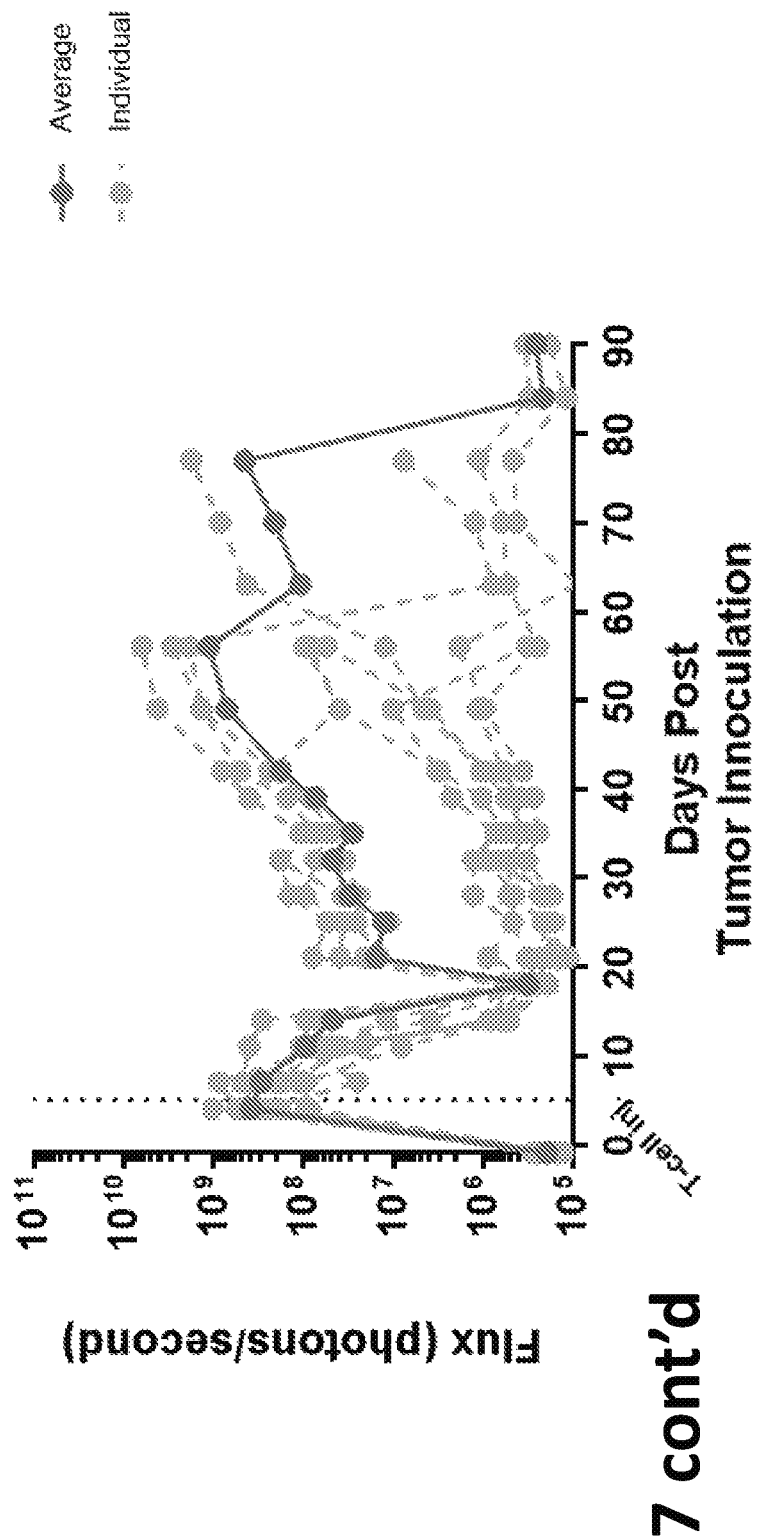
Figure 7:
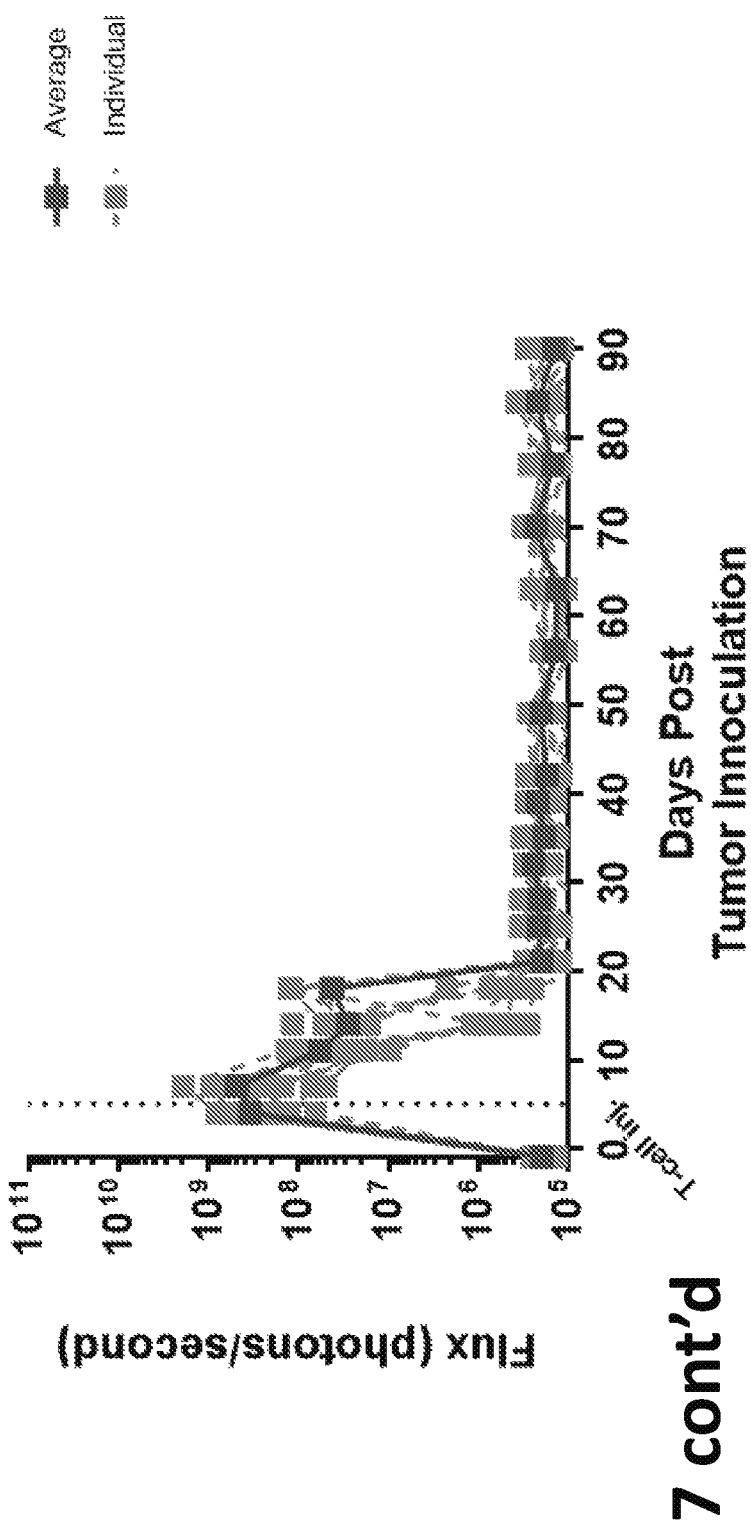

FIG. 7 shows levels of B7H3+ Be2 tumor cells detected using a ffluc marker and survival rate, in mice inoculated with Be2 cells, and treated with CD4 and CD8+ B7H3 or CD19CAR T cells produced by the current tissue culture production center (TCPC) T cell production protocol or the previous PLAT-02 CD19CAR T cell production protocol, respectively.

In this model, approximately 4.3×10$^6$ Be2 CD19t GFP:ffluc (cJ06713) tumor cells were injected subcutaneously on Day 0 (FIG. 7). On Day 4, flux analysis (by imaging) was performed to confirm the presence of tumor cells in the mice (FIG. 7). On Day 5, approximately 20×10$^6$ 1:1 CD4:CD8T cells were administered by intravenous injection (FIG. 7). Flux analysis (by imaging) and survival was monitored until the end of study, i.e., Day 90 (FIG. 7).

Data showed both the B7H3CAR T cells and CD19CAR T cells were able to reduce flux and prolong survival in this subcutaneous Be2 model (FIG. 7). Thus, data showed that both the B7H3CAR T cells and CD19CAR T cells were able to eradicate subcutaneous tumor cells in vivo.

Example 8—Production Run T Cells can Eradicate Subcutaneous Tumor Cells In Vivo

Figure 8:
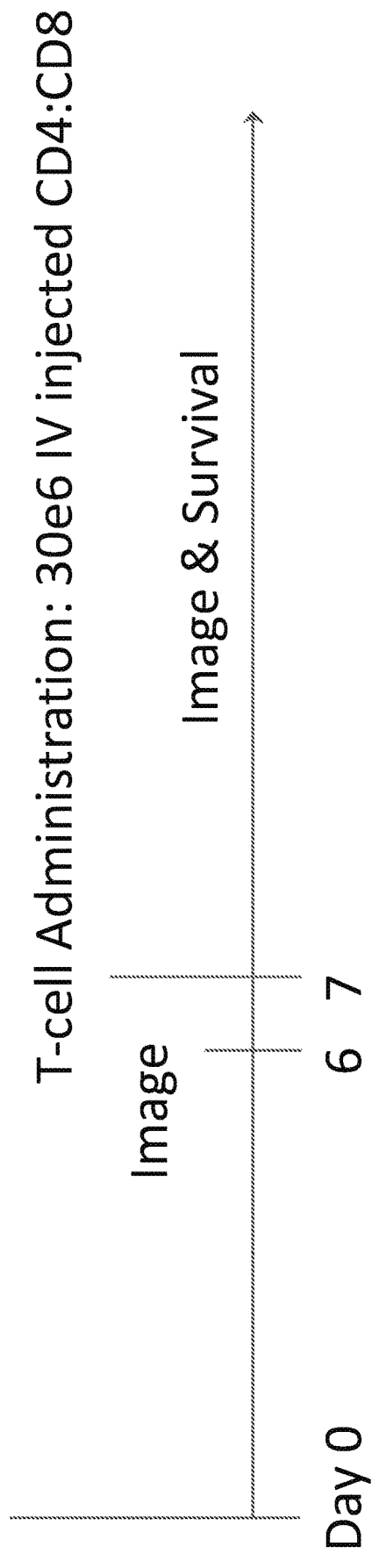
FIG. 8 is a series of graphs showing data related to eradication by T cells of subcutaneous Be2 neuroblastoma tumor cells in vivo (Example 8).
Figure 8:
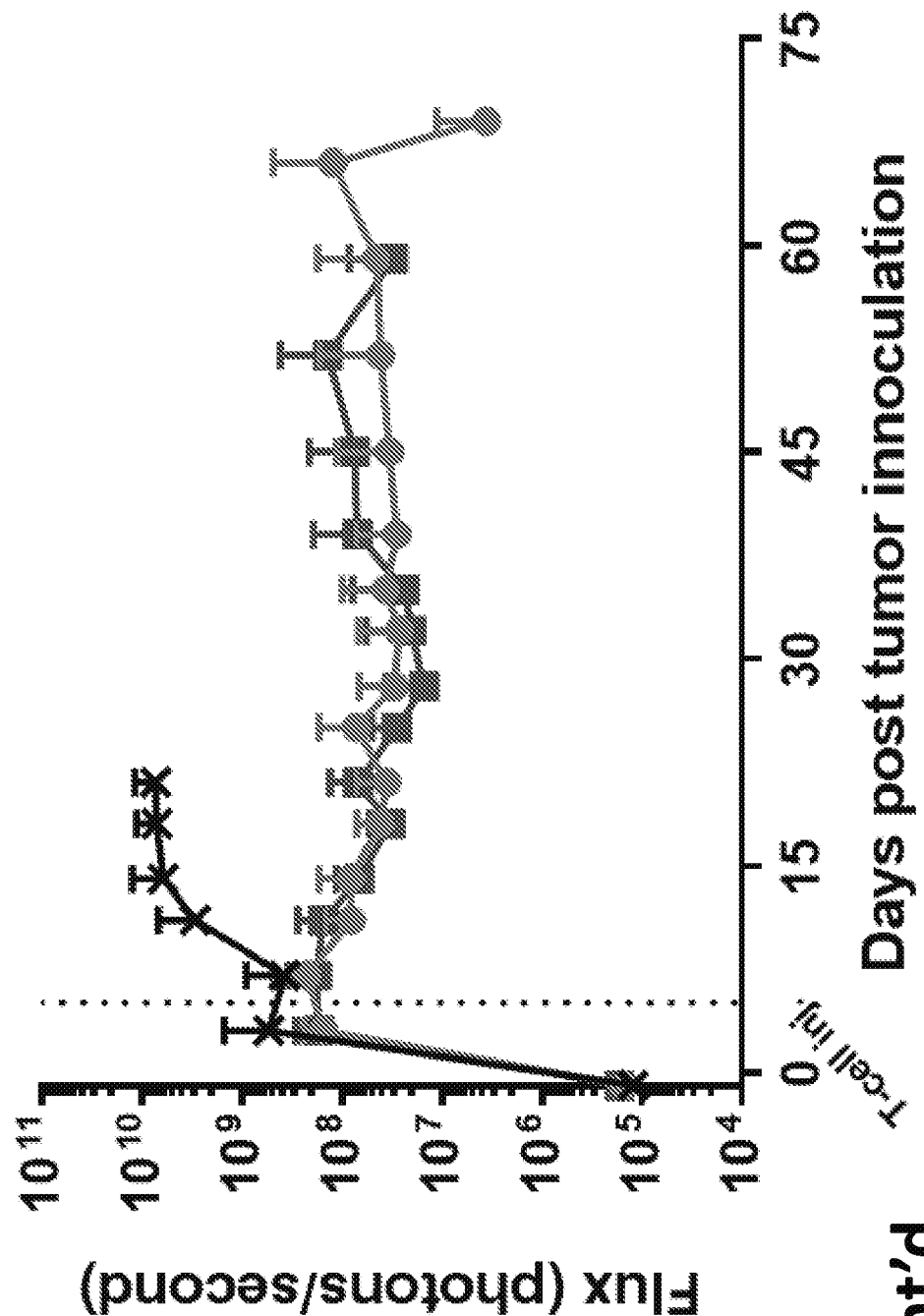
Figure 8:
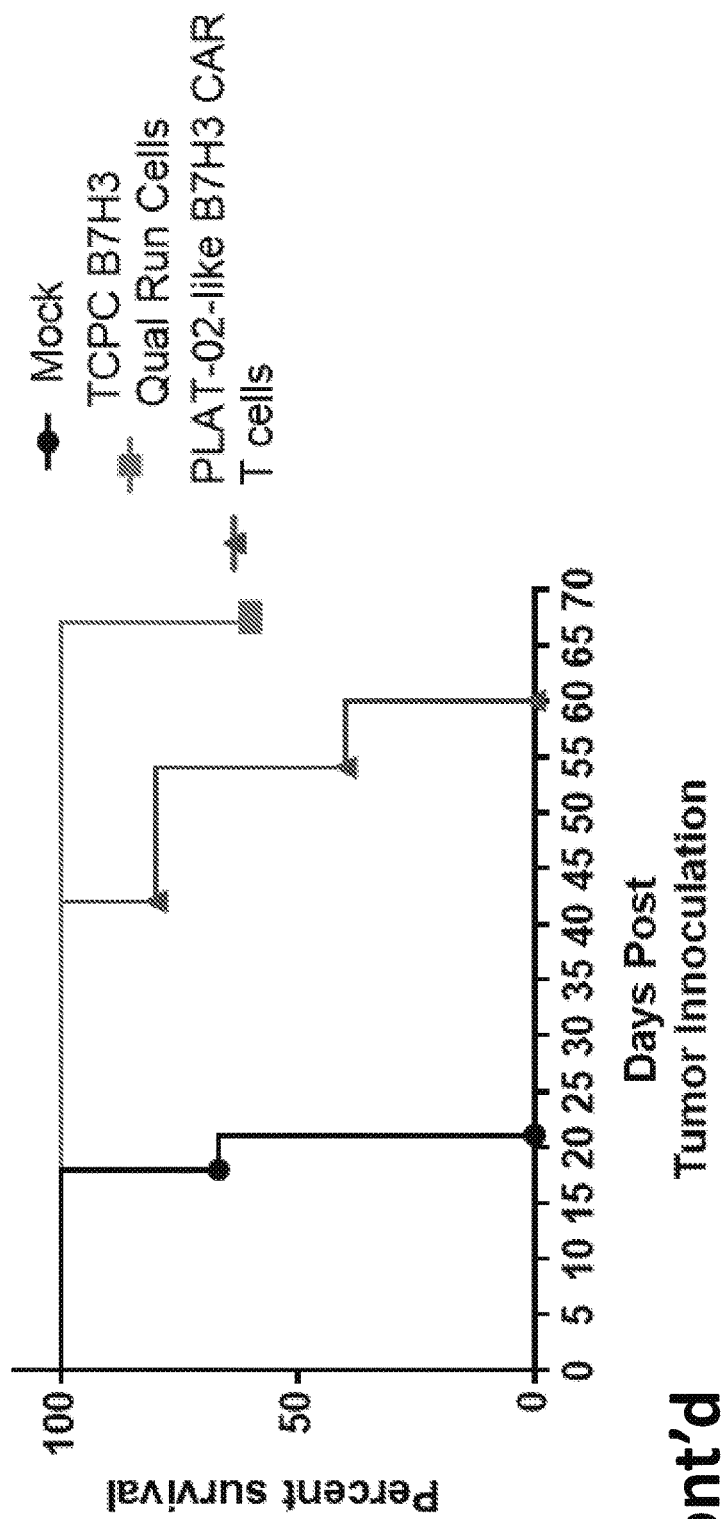
Figure 8:
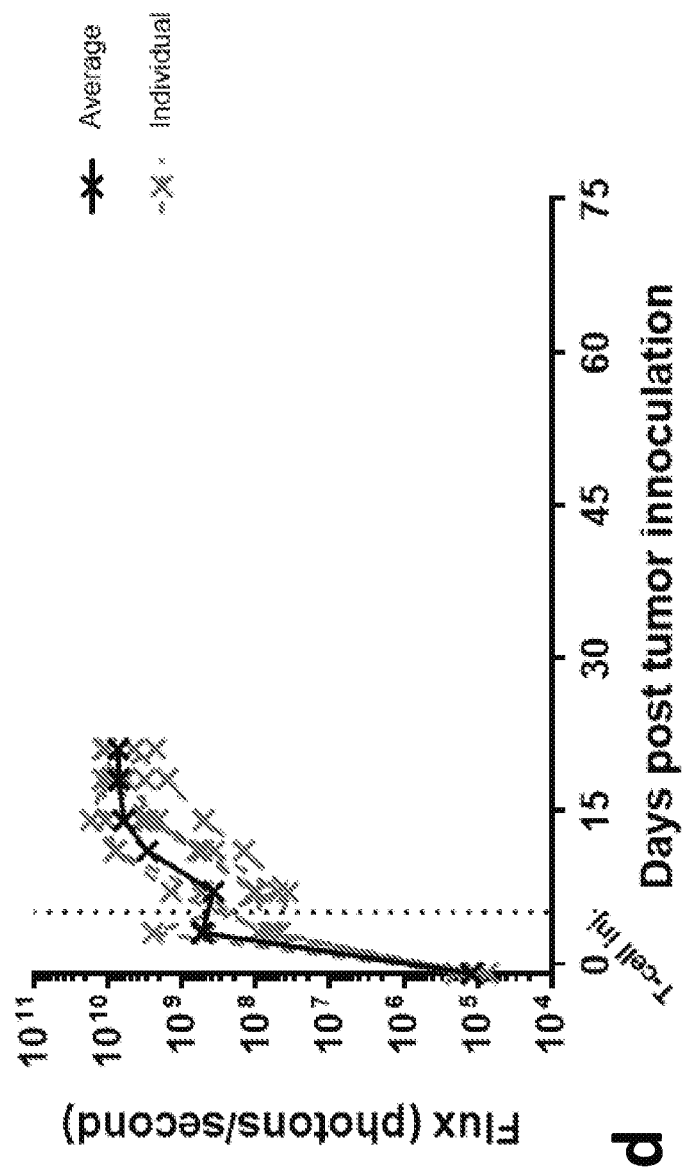
Figure 8:
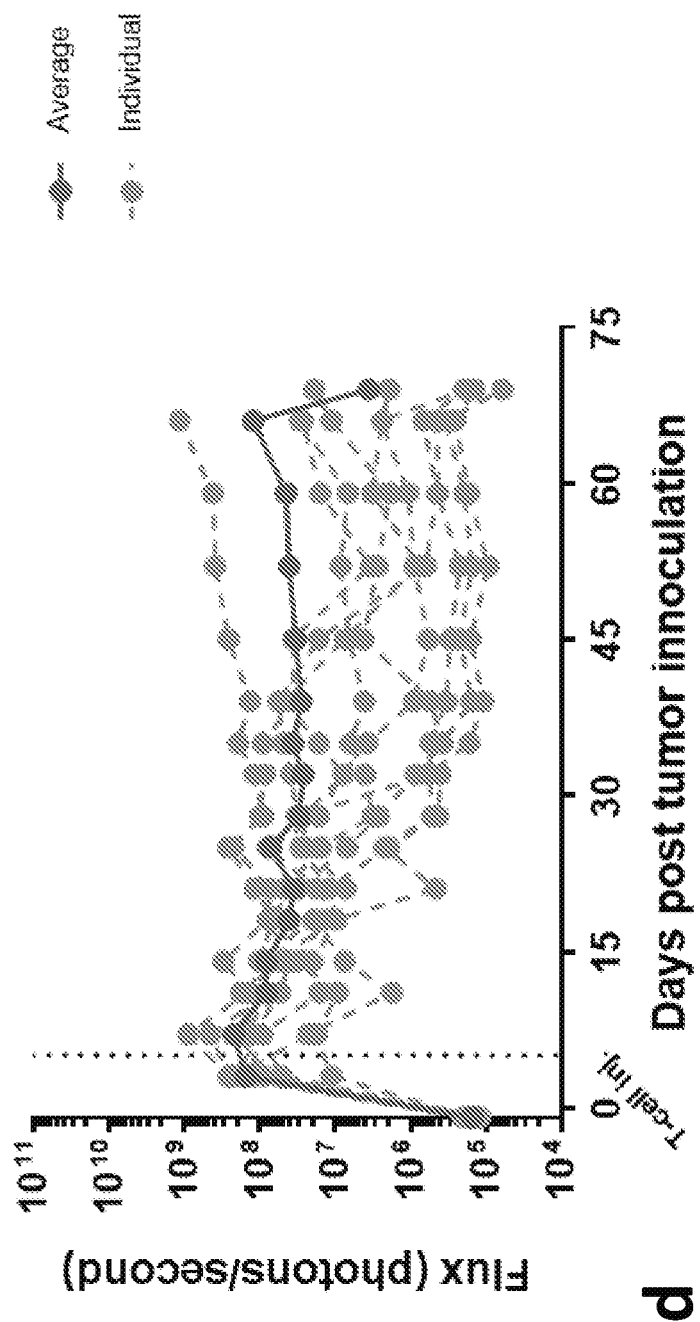
Figure 8:
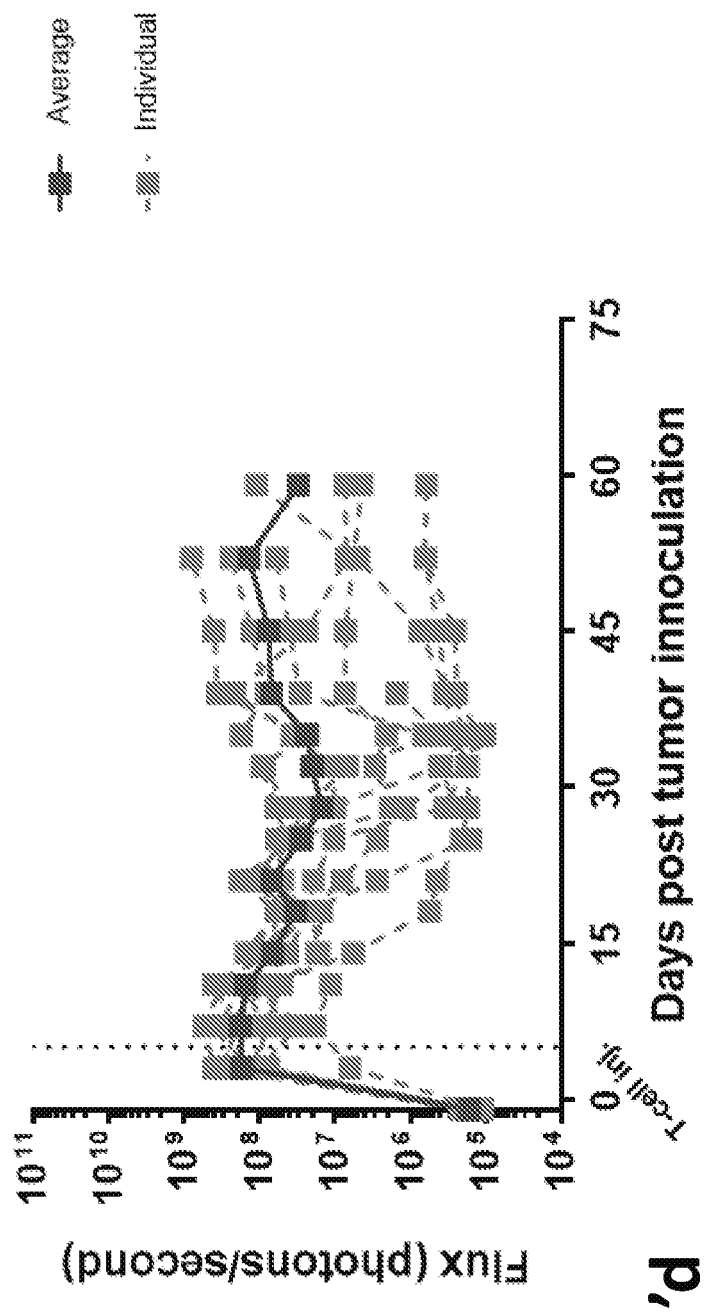

FIG. 8 shows levels of B7H3+ Be2 tumor cells detected using a ffluc marker and survival rate, in mice inoculated with Be2 cells, and treated with CD4 and CD8+ B7H3 T cells produced by the current tissue culture production center (TCPC) T cell production protocol or the previous PLAT-02 T cell production protocol.

In this model, approximately $5\times10^6$ Be2 CD19t GFP:ffluc (cJ06713) tumor cells were injected subcutaneously on Day 0 (FIG. 8). One Day 6, flux analysis (by imaging) was performed to confirm the presence of tumor cells in the mice (FIG. 8). On Day 5, $30\times10^6$ 1:1 CD4:CD8 T cells were administered by intravenous injection (FIG. 8). Flux analysis (by imaging) and survival was monitored until the end of study, i.e., Day 75 (FIG. 8).

Data showed both of the B7H3CAR T cell lots were able to reduce flux and prolong survival in this subcutaneous Be2 model (FIG. 8). Thus, data showed that both of the B7H3CAR T cell lots were able to eradicate subcutaneous tumor cells in vivo Example 9—CD8+ B7H3CAR T Cells can Eradicate U251T Glioma Tumor Cells In Vivo FIG. 9 shows levels of B7H3+U251T tumor cells detected using a ffluc marker and survival rate, in mice inoculated with U251T cells, and treated with CD8+ B7H3 CAR T cells.

Figure 9:
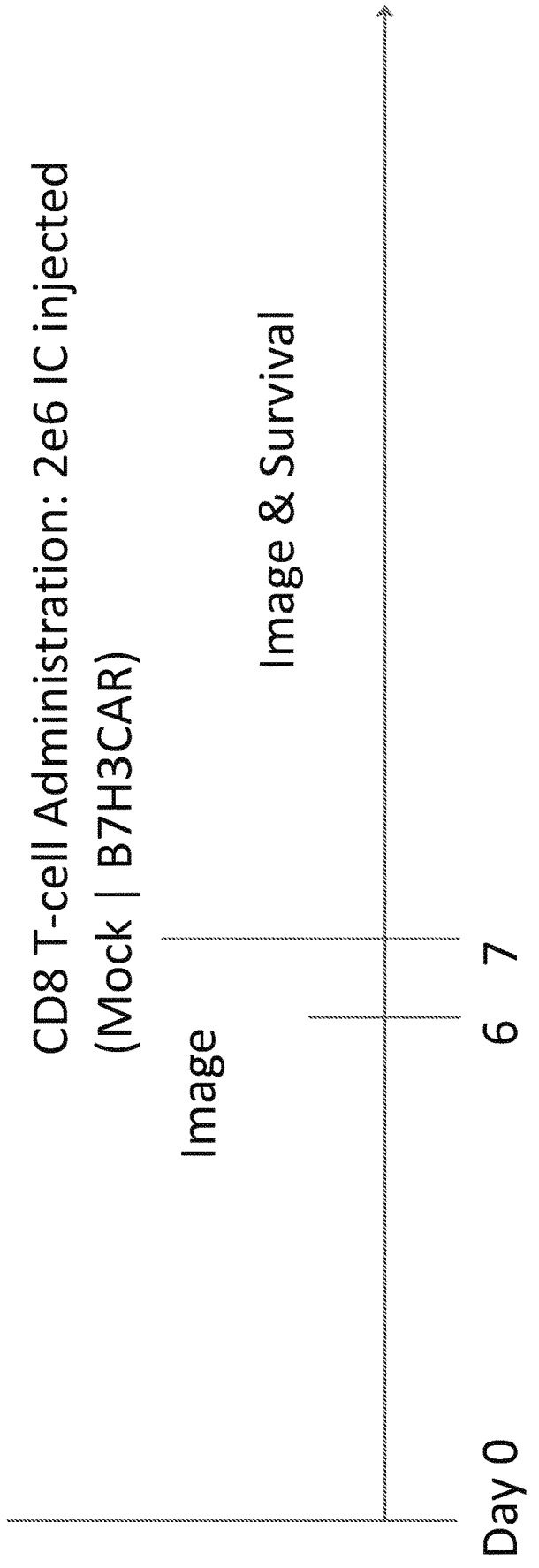
FIG. 9 is a series of graphs showing data related to eradication by CD8+ B7H3CAR T cells of U251T glioma tumor cells in vivo (Example 9).
Figure 9:
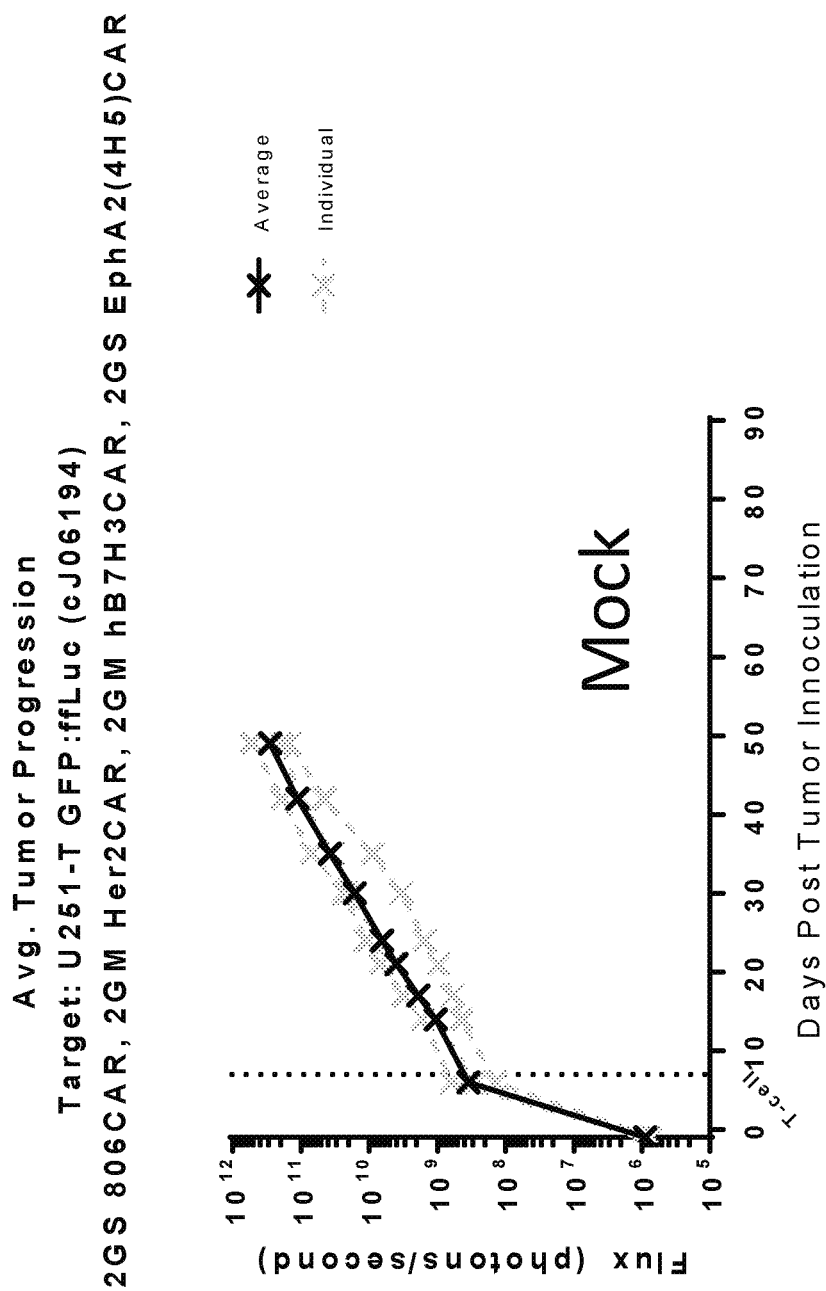
Figure 9:
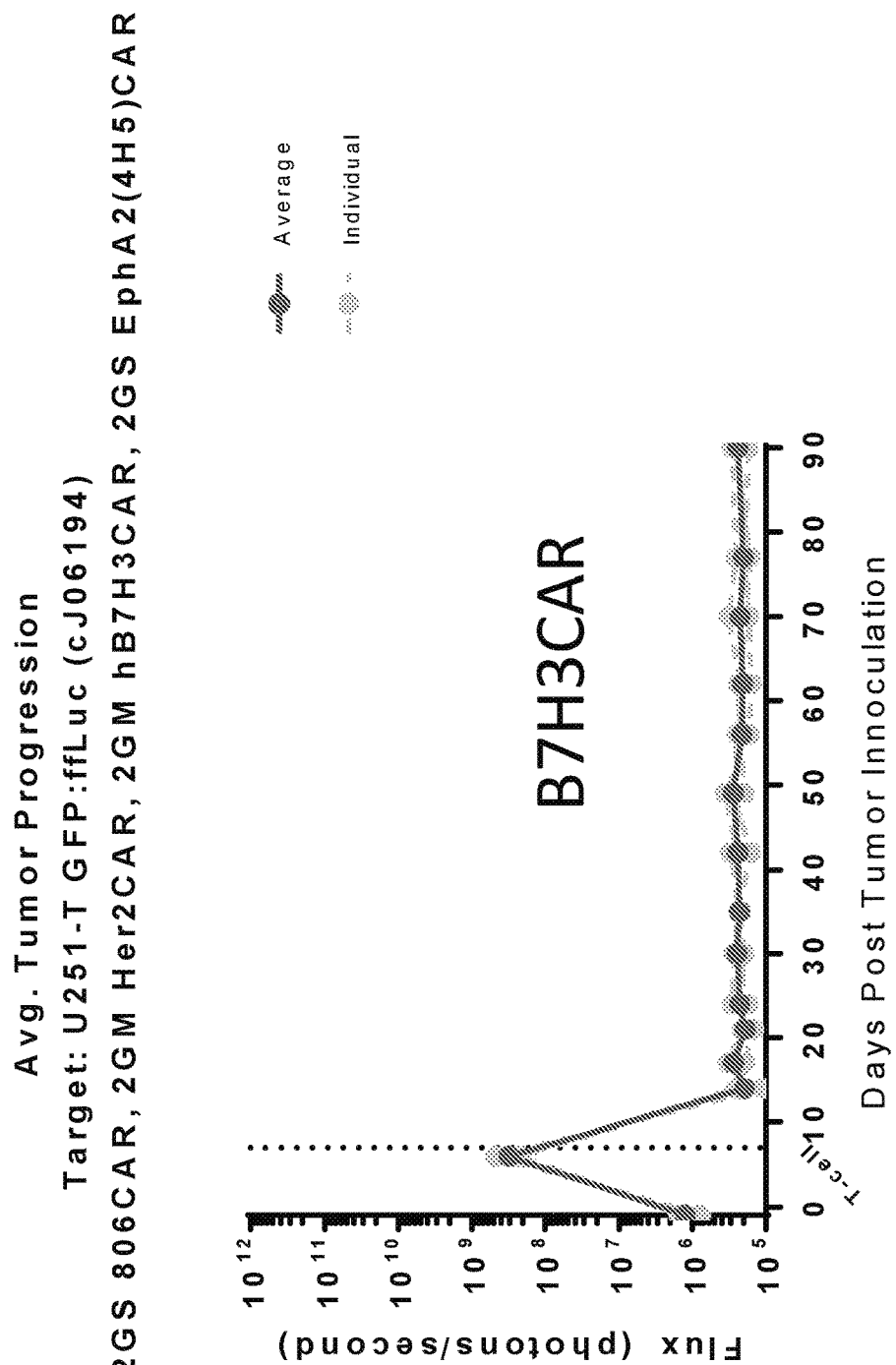
Figure 9:
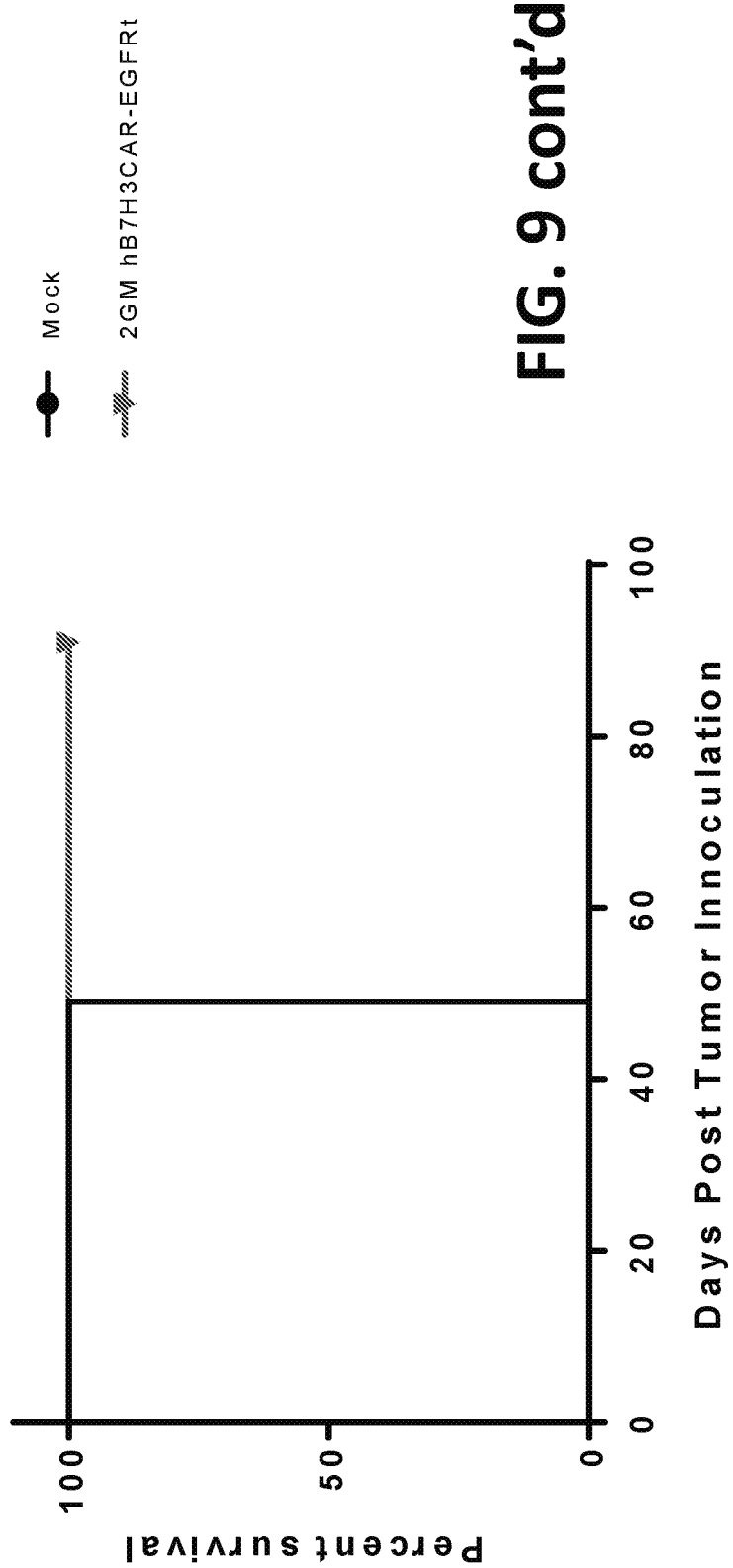

In this model, approximately 200,000 U251T GFP:ffluc (cJ06194) tumor cells were injected intracranially on Day 0 (FIG. 9) One Day 6, flux analysis (by imaging) was performed to confirm the presence of tumor cells in the mice (FIG. 9). On Day 7, approximately $2\times10^6$ Mock or B7H3CAR T cells were administered in the same coordinates. Flux analysis (by imaging) and survival was monitored until the end of study, i.e., Day 90 (FIG. 9).

Data showed that B7H3CAR T cell population was able to reduce flux and prolong survival in this intracranial U251T model (FIG. 9). Thus, data showed that CD8+ B7H3 CAR T cells were able to eradicate U251T glioma tumor cells in vivo Example 10—CD8+ B7H3CAR T Cells can Eradicate Diffuse Intrinsic Pontine Glioma (DIPG) Primary Tumor Cells In Vivo FIG. 10 shows levels of B7H3+ DIPG tumor cells detected using a ffluc marker and survival rate, in mice inoculated with DIPG cells, and treated with CD8+ B7H3 CAR T cells.

Figure 10:
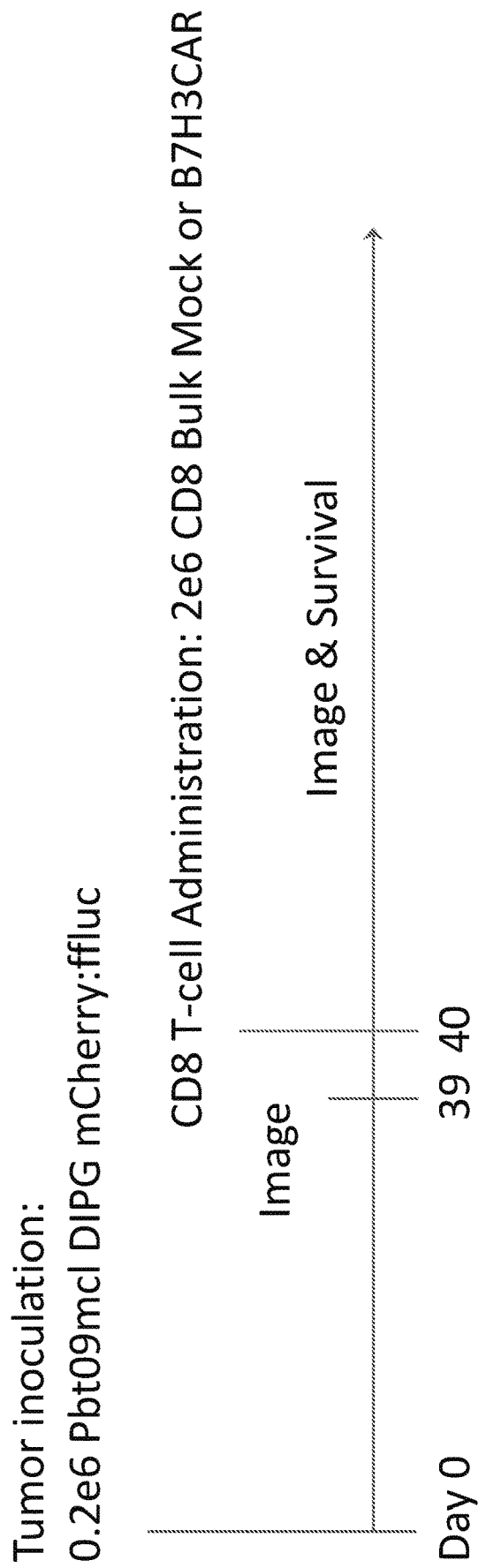
FIG. 10 is a series of graphs showing data related to eradication by CD8+ B7H3CAR T cells of Diffuse Intrinsic Pontine Glioma (DIPG) primary tumor cells in vivo (Example 10).
Figure 10:
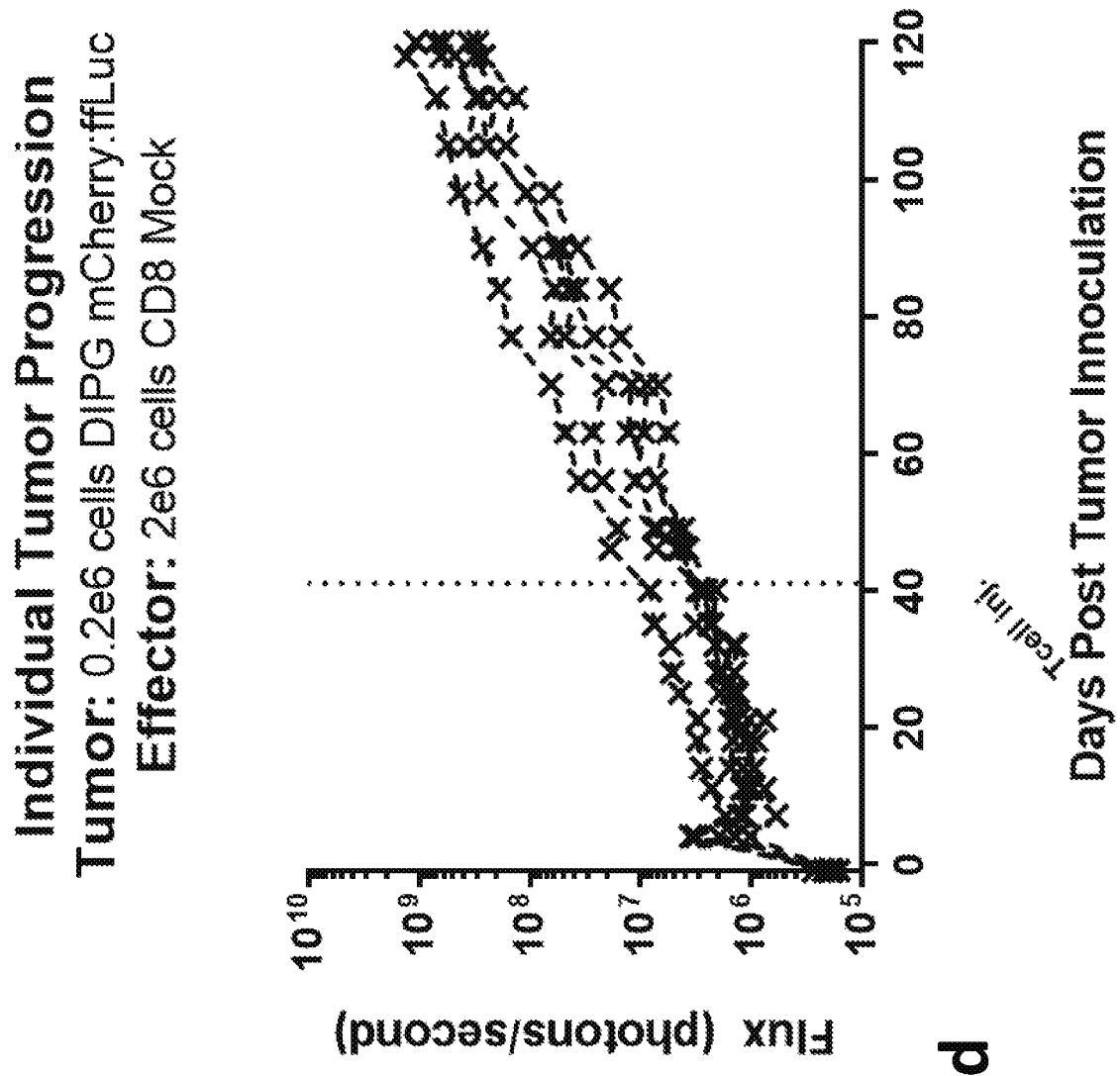
Figure 10:
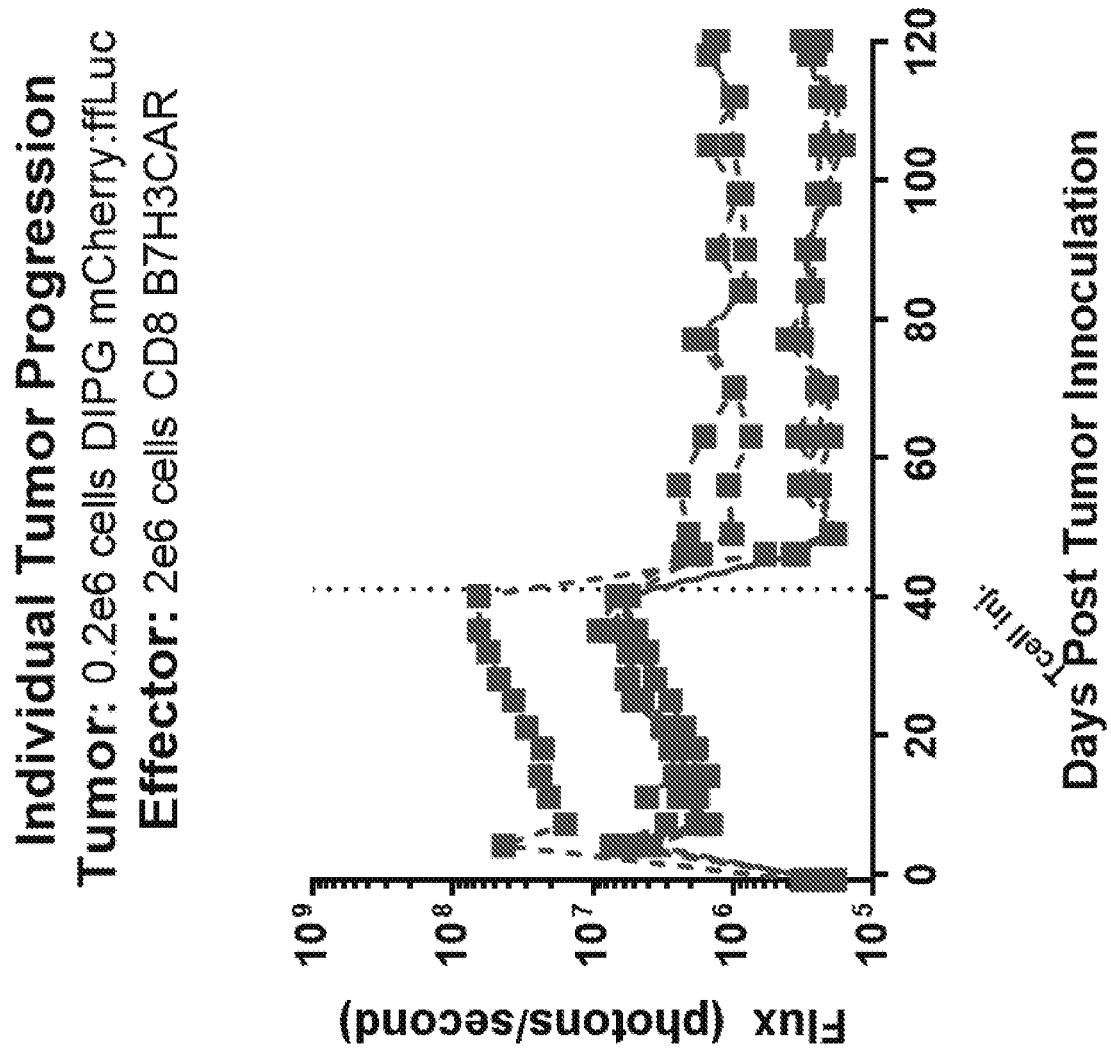
Figure 10:
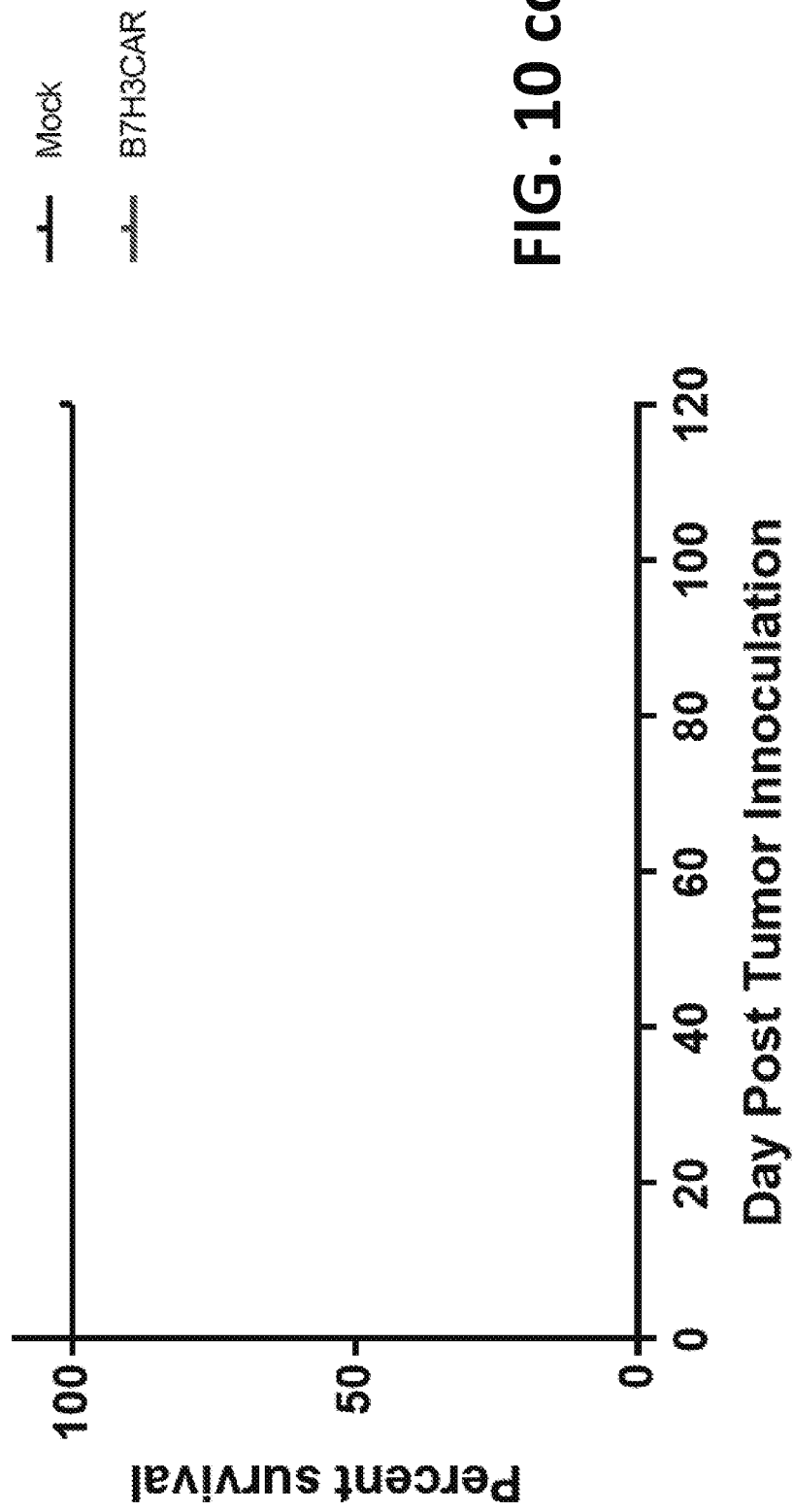

In this model, approximately $0.2^6$ Pbt09mcl DIPG mCherry:ffluc tumor cells were injected intracranially on Day 0 (FIG. 10). One Day 39, flux analysis (by imaging) was performed to confirm the presence of tumor cells in the mice (FIG. 10). On Day 40, approximately $2\times10^6$ CD8 Bulk Mock or B7H3CAR T cells were administered in the same coordinates (FIG. 10). Flux analysis (by imaging) and survival was monitored until the end of study, i.e., Day 90 (FIG. 10). The study was ended prior to the Mock group succumbing to tumor; however, the B7H3 CAR T cells were able to reduce flux back to baseline as compared to the Mock treated group. DIPG is a rare tumor type that is not currently targeted by cellular immunotherapy approaches.

Data showed that the B7H3CAR T cell population was able to reduce flux and prolong survival in this intracranial DIPG model (FIG. 10). Thus, data showed that CD8+ B7H3CAR T cells were able to eradicate DIPG primary tumor cells in vivo.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. An isolated polynucleotide encoding a chimeric antigen receptor (CAR) comprising:
   a single-chain variable fragment (scFv) capable of specifically binding a human B7H3 Ig4 isoform;
   a transmembrane domain;
   an IgG4 hinge spacer between the scFv and the transmembrane domain, wherein the IgG4 hinge spacer comprises an IgG4 hinge-CH3 spacer having a length less than 229 consecutive amino acid residues; and
   an intracellular signaling domain.

2. The isolated polynucleotide of claim 1, wherein the scFv comprises:
   a heavy chain variable region ($V_H$) polypeptide comprising a $V_H$ CDR3 having at least 95% sequence identity with the amino acid sequence of SEQ ID NO:03, and
   a light chain variable region ($V_L$) polypeptide comprising a $V_L$ CDR3 having at least 95% sequence identity with the amino acid sequence of SEQ ID NO:06.

3. The isolated polynucleotide of claim 2, wherein:
   the $V_H$ polypeptide further comprises a $V_H$ CDR1 having at least 95% sequence identity with the amino acid sequence of SEQ ID NO:01, and a $V_H$ CDR2 having at least 95% sequence identity with the amino acid sequence of SEQ ID NO:02; and
   the $V_L$ polypeptide further comprises a $V_L$ CDR1 having at least 95% sequence identity with the amino acid sequence of SEQ ID NO:04, and a $V_L$ CDR2 having at least 95% sequence identity with the amino acid sequence of SEQ ID NO:05.

4. The isolated polynucleotide of claim 2, wherein:
   the $V_L$ polypeptide comprises an amino acid sequence having at least 95% sequence identity with the amino acid sequence of SEQ ID NO: 15; and
   the $V_H$ polypeptide comprises an amino acid sequence having at least 95% sequence identity with the amino acid sequence of SEQ ID NO:13.

5. The isolated polynucleotide of 1, wherein the IgG4 hinge spacer comprises a sequence having at least 95% sequence identity with the amino acid sequence of SEQ ID NO:19.

6. The isolated polynucleotide of claim 1, wherein the transmembrane domain comprises a CD28 transmembrane domain (CD28tm) having at least 95% sequence identity with the amino acid sequence of SEQ ID NO:30.

7. The isolated polynucleotide of claim 1, wherein the intracellular signaling domain comprises all or a portion of a CD3 zeta in combination with a co-stimulatory domain selected from the group consisting of signaling domains of CD27, CD28, 4-1BB, OX-40, CD30, CD40, PD-1, ICOS, LFA-1, CD2, CD7, NKG2C, B7-H3, and a combination thereof.

8. The isolated polynucleotide of claim 7, wherein the intracellular signaling domain comprises the CD3 zeta encoded by a nucleic acid having at least 95% sequence identity with the nucleotide sequence of SEQ ID NO:31; and the 4-1BB is encoded by a nucleic acid having at least 95% sequence identity with the nucleotide sequence of SEQ ID NO:32.

9. The isolated polynucleotide of claim 1, further comprising:
a nucleic acid encoding an identifier marker; optionally, wherein the identifier marker is a truncated receptor selected from the group consisting of a truncated EGFR (EGFRt), a truncated HER2 (HER2t), and a truncated CD19 (CD19t);
a ribosomal skip sequence comprises P2A or T2A; or
a selectable marker comprising a dihydrofolate reductase (DHFR) transgene, optionally, wherein the DHFR comprises amino acid mutations of L22F and F31S.

10. A protein encoded by the polynucleotide of claim 1.

11. A vector comprising the polynucleotide of claim 1, wherein the vector is a viral vector.

12. The vector of claim 11, wherein the vector is a lentiviral, an adenoviral vector, or an adeno-associated virus (AAV) vector.

13. A cell comprising the polynucleotide of claim 1, or a protein encoded by the polynucleotide.

14. The cell of claim 13, wherein the cell is selected from the group consisting of (i) a CD8+ T cell, (ii) a CD4+ T cell, (iii) a CD8+ T cytotoxic lymphocyte selected from the group consisting of a naïve CD8+ T cell, a central memory CD8+ T cell, an effector memory CD8+ T cell, and a bulk CD8+ T cell; (iv) a CD4+ T helper lymphocyte cell selected from the group consisting of a naïve CD4+ T cell, a central memory CD4+ T cell, an effector memory CD4+ T cell, and a bulk CD4+ T cell; (v) a precursor T cell; and (vi) a hematopoietic stem cell.

15. A pharmaceutical composition comprising the cell of claim 13, and a pharmaceutically acceptable excipient.

16. A method of preparing a cell comprising a chimeric antigen receptor (CAR), comprising:
(i) introducing the polynucleotide of claim 1 into a lymphocyte; and
(ii) culturing the lymphocyte comprising the isolated nucleic acid in the presence of an agent selected from the group consisting of an anti-CD3 antibody, an anti-CD28 antibody, and a cytokine.

17. A method of treating, inhibiting, or ameliorating a tumor in a subject, wherein the tumor comprises a B7H3+ cell comprising administering the cell of claim 13 to the subject.

18. The method of claim 17, wherein the cell is autologous to the subject.

19. The method of claim 17, wherein the tumor comprises a cancer selected from the group consisting of melanoma, leukemia, breast, prostate, ovarian, pancreatic, colorectal, endometrial, oral squamous cell carcinoma, cervical, non-small lung, bladder, clear cell renal cell carcinoma, glioma, oligodendroglioma, anaplastic astrocytoma, glioblastoma multiforme (GBM), ependymoma, and intrinsic pontine glioma (DIPG).

20. The method of claim 17, wherein the subject is human.

21. The isolated polynucleotide of claim 1, wherein the IgG4 hinge-CH3 spacer has a length of 119 consecutive amino acid residues.

22. The isolated polynucleotide of claim 1, wherein the scFv comprises:
a heavy chain variable region ($V_H$) polypeptide encoded by a nucleic acid having at least 95% sequence identity with the nucleotide sequence of SEQ ID NO: 14, and
a light chain variable region ($V_L$) polypeptide encoded by a nucleic acid having at least 95% sequence identity with the nucleotide sequence of SEQ ID NO:16.

23. The isolated polynucleotide of claim 1, wherein the scFv comprises:
a heavy chain variable region ($V_H$) polypeptide comprising the amino acid sequence of SEQ ID NO:13 having 0-3 conservative amino acid substitutions, and a light chain variable region ($V_L$) polypeptide comprising the amino acid sequence of SEQ ID NO:15 having 0-3 conservative amino acid substitutions.

24. A chimeric antigen receptor (CAR) comprising:
a single-chain variable fragment (scFv) capable of specifically binding a human B7H3 Ig4 isoform;
a CD28 transmembrane domain;
an IgG4 hinge spacer between the scFv and the transmembrane domain, wherein the IgG4 hinge spacer comprises an IgG4 hinge-CH3 spacer having a length less than 229 consecutive amino acid residues; and
an intracellular signaling domain comprising a CD3 zeta domain and a 4-1BB co-stimulatory domain.

* * * * *